US010076620B2

(12) United States Patent
Schmidt et al.

(10) Patent No.: US 10,076,620 B2
(45) Date of Patent: Sep. 18, 2018

(54) ANESTHETIC CIRCUIT HAVING A HOLLOW FIBER MEMBRANE

(71) Applicant: DMF Medical Incorporated, Halifax (CA)

(72) Inventors: Klaus Michael Schmidt, Halifax (CA); David Cecil Roach, Halifax (CA); Florentin Michael Wilfart, Halifax (CA)

(73) Assignee: DMF MEDICAL INCORPORATED, Nova Scotia (CA)

(*) Notice: Subject to any disclaimer, the term of this patent is extended or adjusted under 35 U.S.C. 154(b) by 904 days.

(21) Appl. No.: 14/139,216

(22) Filed: Dec. 23, 2013

(65) Prior Publication Data

US 2014/0174438 A1 Jun. 26, 2014

Related U.S. Application Data

(60) Provisional application No. 61/745,553, filed on Dec. 22, 2012, provisional application No. 61/764,405, filed on Feb. 13, 2013.

(51) Int. Cl.
*A61M 16/00* (2006.01)
*A61M 16/10* (2006.01)
(Continued)

(52) U.S. Cl.
CPC ........ *A61M 16/0093* (2014.02); *A61M 16/01* (2013.01); *A61M 16/104* (2013.01);
(Continued)

(58) Field of Classification Search
CPC .............. A61M 16/0093; A61M 16/01; A61M 16/104; A61M 16/1065;
(Continued)

(56) References Cited

U.S. PATENT DOCUMENTS 2,966,235 A 12/1960 Kammermeyer
3,097,638 A 7/1963 Streimer
(Continued)

FOREIGN PATENT DOCUMENTS

CA 2615018 1/2008
CA 2658778 1/2008
(Continued)

OTHER PUBLICATIONS

Yury V. Kistenev; Alexey V. Borisov; Alexander V. Shapovalov and Olga Y. Nikiforova; "Analysis of the component composition of exhaled air using laser spectroscopy and canonical correlation analysis", Proc. SPIE 9680, 21st International Symposium Atmospheric and Ocean Optics: Atmospheric Physics, 96804C (Nov. 19, 2015); doi:10.1117/12.220578.*
(Continued)

*Primary Examiner* — (Jackie) Tan-Uyen T Ho
*Assistant Examiner* — Joseph D Boecker
(74) *Attorney, Agent, or Firm* — Bereskin & Parr LLP

(57) ABSTRACT

An anesthetic circuit is provided for treating a patient. The anesthetic circuit includes a membrane having a plurality of hollow fibers. Also provided is a fluid separation apparatus connectable to an anesthetic circuit. In a further embodiment, a method is provided for anesthetic treatment of a patient.

21 Claims, 52 Drawing Sheets

(51) Int. Cl.

| | | |
|---|---|---|
| *A61M 16/01* | (2006.01) | |
| *B01D 53/22* | (2006.01) | |
| *B01D 53/62* | (2006.01) | |
| *B01D 53/81* | (2006.01) | |
| *A61M 16/08* | (2006.01) | |
| *A61M 16/12* | (2006.01) | |
| *A61M 16/22* | (2006.01) | |

(52) U.S. Cl.
CPC ....... *A61M 16/1065* (2014.02); *B01D 53/229* (2013.01); *B01D 53/62* (2013.01); *B01D 53/81* (2013.01); *A61M 16/0045* (2013.01); *A61M 16/0891* (2014.02); *A61M 16/12* (2013.01); *A61M 16/22* (2013.01); *A61M 2207/00* (2013.01); *B01D 2053/224* (2013.01); *B01D 2251/30* (2013.01); *B01D 2251/60* (2013.01); *B01D 2251/80* (2013.01); *B01D 2252/20478* (2013.01); *B01D 2252/20494* (2013.01); *B01D 2257/504* (2013.01); *B01D 2259/4533* (2013.01); *Y02C 10/04* (2013.01); *Y02C 10/10* (2013.01)

(58) Field of Classification Search
CPC .. A61M 2202/0225; A61M 2202/0241; B01D 53/81; B01D 53/229; B01D 53/62; B01D 2252/20478; B01D 2251/80; B01D 2251/60; B01D 2053/224; B01D 2257/504; B01D 2252/20494
USPC .................................................... 128/203.12
See application file for complete search history.

(56) References Cited

U.S. PATENT DOCUMENTS

| | | | |
|---|---|---|---|
| 3,422,008 A * | 1/1969 | McLain ................. | B01D 53/22 210/321.74 |
| 3,489,144 A | 1/1970 | Dibelius et al. | |
| 3,536,611 A * | 10/1970 | Filippi .................... | B01D 63/02 210/321.89 |
| 3,592,191 A | 7/1971 | Jackson | |
| 3,923,057 A | 12/1975 | Chalon | |
| 4,312,339 A | 1/1982 | Thompson, Sr. | |
| 4,622,976 A | 11/1986 | Timpe et al. | |
| 4,685,940 A | 8/1987 | Soffer et al. | |
| 4,707,268 A * | 11/1987 | Shah ....................... | B01D 63/02 210/650 |
| 4,905,685 A | 2/1990 | Olsson et al. | |
| 4,940,617 A * | 7/1990 | Baurmeister .......... | B01D 63/02 428/113 |
| 4,975,247 A * | 12/1990 | Badolato .............. | A61M 1/1698 128/DIG. 3 |
| 5,016,628 A | 5/1991 | Lambert | |
| 5,032,245 A | 7/1991 | Gemelli et al. | |
| 5,044,361 A | 9/1991 | Werner et al. | |
| 5,044,363 A | 9/1991 | Burkhart | |
| 5,128,037 A * | 7/1992 | Pearl .................... | B01D 61/10 210/321.74 |
| 5,192,320 A * | 3/1993 | Anazawa ............ | B01D 67/0025 623/23.65 |
| 5,217,689 A * | 6/1993 | Raible .................. | A61M 1/1698 128/DIG. 3 |
| 5,231,980 A | 8/1993 | Fillipovic et al. | |
| 5,281,254 A | 1/1994 | Birbara et al. | |
| 5,355,872 A | 10/1994 | Riggs et al. | |
| 5,471,979 A | 12/1995 | Psaros et al. | |
| 5,515,845 A | 5/1996 | Filipovic et al. | |
| 5,520,169 A | 5/1996 | Georgieff et al. | |
| 5,778,876 A | 7/1998 | Gorin | |
| 5,779,897 A * | 7/1998 | Kalthod ................. | B01D 53/22 210/321.8 |
| 5,855,201 A * | 1/1999 | Fukui ...................... | B01D 53/22 128/200.11 |
| 5,925,831 A | 7/1999 | Storsved | |
| 6,134,914 A | 10/2000 | Eschwey et al. | |
| 6,152,133 A * | 11/2000 | Psaros ................. | A61M 16/009 128/203.12 |
| 6,168,649 B1 * | 1/2001 | Jensvold .............. | B01D 53/226 95/47 |
| 6,206,002 B1 | 3/2001 | Lambert | |
| 6,279,576 B1 | 8/2001 | Lambert | |
| 6,403,660 B1 * | 6/2002 | Espinoza ............. | A61K 31/455 424/449 |
| 6,405,539 B1 | 6/2002 | Stach et al. | |
| 6,471,747 B1 | 10/2002 | Venkatesh et al. | |
| 6,375,876 B1 | 12/2002 | Membrana | |
| 6,497,752 B1 | 12/2002 | Kessler et al. | |
| 6,635,103 B2 | 10/2003 | Sirkar et al. | |
| 6,709,483 B1 | 3/2004 | Hodgson, Jr. | |
| 6,729,329 B2 | 5/2004 | Berry | |
| 6,863,067 B2 | 3/2005 | Loncar | |
| 6,892,726 B1 | 5/2005 | Heinonen et al. | |
| 6,929,680 B2 | 8/2005 | Krushnevych et al. | |
| 6,958,085 B1 | 10/2005 | Parrish | |
| 7,048,778 B2 | 5/2006 | Gobina | |
| 7,077,136 B2 | 7/2006 | Ahlmen et al. | |
| 7,146,980 B2 | 12/2006 | Loncar | |
| 7,246,621 B2 | 7/2007 | McNeirney | |
| 7,290,544 B1 | 11/2007 | Sarela et al. | |
| 7,347,207 B2 | 3/2008 | Ahlmen et al. | |
| 7,429,343 B2 | 9/2008 | Kessler et al. | |
| 7,442,236 B2 | 10/2008 | Taveira et al. | |
| 7,520,280 B2 | 4/2009 | Gordon | |
| 7,596,965 B2 | 10/2009 | Berry et al. | |
| 7,628,034 B2 | 12/2009 | Berry et al. | |
| 7,644,594 B2 | 1/2010 | Berry et al. | |
| 7,669,438 B2 | 3/2010 | Berry et al. | |
| 7,814,908 B2 | 10/2010 | Psaros | |
| 7,832,398 B2 | 11/2010 | Laurila | |
| 7,993,681 B2 | 8/2011 | Roth | |
| 8,038,772 B2 | 10/2011 | Fuesting et al. | |
| 8,146,593 B2 | 4/2012 | Riecke | |
| 8,127,762 B2 | 5/2012 | Loncar et al. | |
| 8,205,610 B2 | 6/2012 | Ahlmen et al. | |
| 8,210,169 B2 | 7/2012 | Ahlmen et al. | |
| 8,371,298 B2 | 2/2013 | Hallback et al. | |
| 8,449,661 B2 | 5/2013 | Broborg | |
| 8,469,026 B2 | 6/2013 | Blomberg et al. | |
| 8,763,610 B2 | 7/2014 | Schmidt | |
| 2001/0035374 A1 | 11/2001 | Yamamoto et al. | |
| 2001/0047958 A1 * | 12/2001 | Estep .................... | B01D 29/15 210/433.1 |
| 2002/0104542 A1 | 8/2002 | Castor et al. | |
| 2003/0199804 A1 | 10/2003 | Ahlmen et al. | |
| 2004/0089297 A1 | 5/2004 | Videbrink | |
| 2004/0099267 A1 | 5/2004 | Ahlmen et al. | |
| 2004/0103894 A1 | 6/2004 | Loncar | |
| 2004/0103898 A1 * | 6/2004 | Loncar .................. | A61M 16/22 128/205.28 |
| 2004/0149281 A1 | 8/2004 | Ahlmen | |
| 2004/0216743 A1 | 11/2004 | Orr | |
| 2005/0145107 A1 | 7/2005 | Kessler et al. | |
| 2005/0155380 A1 | 7/2005 | Rock | |
| 2005/0166917 A1 | 8/2005 | Ahlmen et al. | |
| 2005/0235831 A1 | 10/2005 | Taveira et al. | |
| 2006/0090651 A1 * | 5/2006 | Liu .................... | B01D 46/0021 96/121 |
| 2006/0130649 A1 | 6/2006 | Jain et al. | |
| 2006/0144235 A1 * | 7/2006 | Clarke ................. | A61M 16/22 96/5 |
| 2007/0017516 A1 | 1/2007 | Schmidt | |
| 2007/0151561 A1 * | 7/2007 | Laurila ................. | A61M 16/22 128/203.13 |
| 2007/0264468 A1 | 11/2007 | Boyd et al. | |
| 2007/0286783 A1 | 12/2007 | Carrette et al. | |
| 2007/0292945 A1 | 12/2007 | Lin et al. | |
| 2008/0029091 A1 | 2/2008 | Mullner | |
| 2008/0060651 A1 * | 3/2008 | Riecke ................. | A61M 16/22 128/205.28 |
| 2008/0072913 A1 | 3/2008 | Baker et al. | |

(56) References Cited

U.S. PATENT DOCUMENTS

| | | | |
|---|---|---|---|
| 2008/0156188 A1* | 7/2008 | Hagg | B01D 53/228 95/51 |
| 2008/0236581 A1 | 10/2008 | Rantala et al. | |
| 2008/0289628 A1 | 10/2008 | Hallback et al. | |
| 2008/0317651 A1 | 10/2008 | Hooper et al. | |
| 2009/0078254 A1 | 3/2009 | Rock | |
| 2009/0126733 A1* | 5/2009 | Kulkarni | B01D 53/22 128/203.16 |
| 2009/0145297 A1 | 6/2009 | Ferguson et al. | |
| 2009/0145761 A1 | 6/2009 | van Hassel | |
| 2009/0165787 A1 | 7/2009 | Ahlmen et al. | |
| 2009/0250054 A1 | 10/2009 | Loncar et al. | |
| 2009/0277448 A1 | 10/2009 | Ahlmen et al. | |
| 2010/0031961 A1 | 2/2010 | Schmidt | |
| 2010/0258117 A1 | 10/2010 | Hargasser | |
| 2011/0017211 A1 | 1/2011 | Ahlmen et al. | |
| 2011/0041848 A1 | 2/2011 | Stone et al. | |
| 2011/0048417 A1 | 3/2011 | Ahlmen et al. | |
| 2011/0113755 A1* | 5/2011 | Kim | B01D 46/0005 60/275 |
| 2011/0159078 A1 | 6/2011 | Burton et al. | |
| 2011/0217220 A1* | 9/2011 | McLellan | B01D 53/62 423/230 |
| 2012/0031402 A1 | 2/2012 | Loncar et al. | |
| 2012/0190103 A1 | 7/2012 | Maurer | |
| 2013/0068222 A1* | 3/2013 | Schmidt | A61M 16/009 128/203.12 |

FOREIGN PATENT DOCUMENTS

| | | |
|---|---|---|
| CN | 104707490 A | 6/2015 |
| DE | 4411533 C1 | 4/1995 |
| DE | 19635002 A1 | 8/1996 |
| DE | 19645223 C1 | 11/1996 |
| DE | 19545598 A1 | 6/1997 |
| DE | 19646791 A1 | 5/1998 |
| DE | 10051910 A1 | 10/2002 |
| DE | 69717215 D1 | 1/2003 |
| DE | 10300141 A1 | 7/2004 |
| DE | 102005032977 B3 | 12/2006 |
| DE | 102006034601 B3 | 2/2008 |
| DE | 102006042348 A1 | 3/2008 |
| EP | 0187708 A2 | 7/1986 |
| EP | 0359755 B1 | 9/1992 |
| EP | 0284227 B1 | 7/1993 |
| EP | 803280 A2 | 10/1997 |
| EP | 0806215 A2 | 11/1997 |
| EP | 428052 B1 | 1/1998 |
| EP | 0841086 A1 | 5/1998 |
| EP | 0621071 B1 | 11/1999 |
| EP | 0901985 A2 | 11/1999 |
| EP | 1057521 A1 | 12/2000 |
| EP | 1086973 A2 | 3/2001 |
| EP | 1086973 A3 | 11/2001 |
| EP | 0806215 B1 | 6/2004 |
| EP | 1424092 A1 | 6/2004 |
| EP | 1803479 A1 | 7/2007 |
| GB | 2207666 B | 3/1992 |
| JP | 61222511 A | 10/1986 |
| JP | 63236502 A | 10/1988 |
| JP | 05501214 A | 3/1993 |
| JP | 09290020 A | 11/1997 |
| JP | 10151327 A | 6/1998 |
| JP | 2000-5314 A | 1/2000 |
| JP | 2000084369 A | 3/2000 |
| JP | 2001-252358 A | 9/2001 |
| JP | 2004174258 A | 6/2004 |
| JP | 2004243051 A | 9/2004 |
| JP | 2005-512615 A | 5/2005 |
| JP | 2006-87683 A | 4/2006 |
| JP | 2006-224076 A | 8/2006 |
| JP | 2009501031 | 1/2009 |
| JP | 2009544382 | 12/2009 |
| JP | 2011514833 A | 5/2011 |
| JP | 2011528416 A | 11/2011 |
| JP | 2012517307 A | 8/2012 |
| JP | 2014519928 A | 8/2014 |
| KR | 100654083 B1 | 11/2006 |
| WO | 9106327 A1 | 5/1991 |
| WO | 9112043 A | 8/1991 |
| WO | 9818718 A1 | 5/1998 |
| WO | 9910034 | 3/1999 |
| WO | 0033903 A1 | 6/2000 |
| WO | 0033904 A1 | 6/2000 |
| WO | 0033949 A1 | 6/2000 |
| WO | 0124858 A3 | 10/2001 |
| WO | 03061812 A2 | 7/2003 |
| WO | 03092778 A1 | 11/2003 |
| WO | 2004050154 | 6/2004 |
| WO | 2005092417 A1 | 10/2005 |
| WO | 2007006348 A1 | 1/2007 |
| WO | 2007006377 A1 | 1/2007 |
| WO | 2008012350 A1 | 1/2008 |
| WO | 2008142665 A1 | 11/2008 |
| WO | 2008148052 A1 | 12/2008 |
| WO | 2009062550 A1 | 5/2009 |
| WO | 2010008110 A1 | 1/2010 |
| WO | 2010081914 A1 | 7/2010 |
| WO | 2010130290 A1 | 10/2010 |
| WO | 2011021978 A1 | 2/2011 |
| WO | 2012174649 A1 | 12/2012 |
| WO | 2013100830 A1 | 7/2013 |
| WO | 2014094139 A1 | 6/2014 |

OTHER PUBLICATIONS

T. Langbein et al., Volaile anaesthetics and the atomsphere: atmospheric lifetimes and atmospheric effects on the halothane, enflurane, isoflurane, desflurane, and sevoflurane, British Journal of Anaesthesia, vol. 82, The Board of Management and Trustees of the British Journal of Anaestheia, Aug. 15, 1998, pp. 66-73, London, United Kingdom.

Thomas Marx et al., Xenon anaesthesia, Journal of the Royal Scoiety of Medicine, vol. 93, Sage Publications, Oct. 2000, pp. 513-517, Thousand Oaks, California.

Uwe Schirmer, et al., Xenon Washout During In-Vitro Extracorporeal Circulation Using Different Oxygenators, Journal of Clinical Monitoring and Computing, vol. 17, Kluwer Academic Publishers, May 14, 2002, pp. 211-215, Netherlands.

Warren K. Grodin et al., Soda Lime Adsorption of Isoflurane and Enflurane, Anesthesiology, vol. 62, American Society of Anesthesiologists, Jul. 23, 1984, pp. 60-64, Schaumburg, Illinois.

Yumiko Ishizawa, General Anesthetic Gases and the Global Environment, Anesthesia & Analgesia Journal, International Anesthesia Research Society, Jan. 2011, pp. 213-217, San Francisco, California.

Z.X. Fang et al., Factors Affecting Production of Compound A from the Interaction of Sevoflurane with Baralyme and Soda Lime, Department of Anesthesia, University of California, 1996, pp. 775-781, San Francisco, California.

Ronald D. Miller et al., Inhaled Anesthetic Pharmaccokinetics: Uptake, Distribution, Metabolism, and Toxicity, Miller's Anesthesia, Oct. 20, 2014, Elsevier Health Sciences, Netherlands.

A. Mansourizadeh et al., Hollow fiber gas-liquid membrane contactors for acid gas capture: A review, Journal of Hazardous Materials, Elsevier B.V., Jun. 16, 2009, pp. 38-53, Amsterdam, Netherlands.

A. Morisato at al., Synthesis and gas permeation properties of poly(4-methyl-2-pentyne), Journal of Membrane Science, vol. 121, Elsevier B.V., Jun. 19, 1996, pp. 243-250, Amsterdam, Netherlands.

A.F. Portual et al., Solubility ofcarbon dioxide in aqueous solutions of amino acid salts, Chemical Engineering Science, vol. 64, Elsevier B.V., Feb. 1, 2009, pp. 1993-2002, Amsterdam, Netherlands.

A.F. Portugal et al., Carbon dioxide absorption kinetics in potassium threonate, Chemical Engineering Science, vol. 63, Elsevier B.V., Apr. 16, 2008, Amsterdam, Netherlands.

A.F. Portugal et al., Carbon dioxide removal from anaesthetic gas circuits using hollow fiber membrane contactors with amino acid

(56) References Cited

OTHER PUBLICATIONS salt solutions, Journal of Membrane Science, vol. 339, Apr. 29, 2009, pp. 275-286, Elsevier B. V., Amsterdam, Netherlands.
A.F. Portugal et al., Characterization of potassium glycinate for carbon dioxide absorption purposes, Chemical Engineering Science, vol. 62, Elsevier B.V., Aug. 6, 2007, Amsterdam, Netherlands.
Ana Filipa Fernandes Vaz Portugal, Carbon Dioxide Removal from Anaesthetic Gas Circuits Using Absorbent Membrane Contactors, Chemical Engineering Department, Faculty of Engineering, University of Porto, Feb. 2009, pp. 1-219, Portugal.
Augusto Tempia et al., The Anesthetic Conserving Device Compared with Conventional Circle System Used Under Different Flow Conditions for Inhaled Anesthesia, Anesthesia & Analgesia, vol. 96, International Anesthesia Research Society, Nov. 19, 2002, pp. 1056-1061, San Francisco, California.
Benedikt Preckel et al., Molecular Mechanisms Transducing the Anesthetic, Analgesic, and Organ-protective Actions of Xenon, Anesthesiology, vol. 105, No. 1, American Society of Anesthesiologists, Jul. 2006, pp. 187-197, Schaumburg, Illinois.
Brandon W. Rowe et al., Influence of temperature on the upper bound: Theoretical considerations and comparison with experimental results, Journal of Membrane Science, vol. 360, Elsevier B.V., May 8, 2010, pp. 58-69, Amsterdam, Netherlands.
Forane (isoflurance, USP) datasheet,Baxter Healthcare Corporation, revised Jul. 2009.
Sevoflurane (USP) Datasheet, Baxter Healthcare Corporation, revised Jan. 12, 2008.
SODASORB® Manual of CO2 Absorption, W. R. Grace & Co., 1993.
SUPRANE—des flurane liquid datasheet, Baxter Healthcare Corporation, Revised Sep. 2013.
D.D. Cunningham et al., Sevoflurane degradation to compound A in anesthesia breathing systems, British Journal of Anesthesia, 1996, pp. 537-543, Oxford, United Kingdom.
Dongbin Zhao et al., Toxicity of Ionic Liquids, Clean Journal, vol. 35, Wiley-VCH Verlag GmbH & Co. KGaA, Dec. 13, 2006, pp. 42-48, Weinheim, Germany.
Eileen M. Saki et al., Inhalation Anesthesiology and Volatile Liquid Anesthetics: Focus on Isoflurane, Desflurane, and Sevoflurane, Pharmacotherapy, vol. 25, No. 12, 2005, pp. 1773-1788, Hoboken, New Jersey.
Eleanor D. Bates et al., CO2 Capture by a Task-Specific Ionic Liquid, Department of Chemistry, University of South Alabama, Nov. 21, 2001, pp. 1-2, Mobile, Alabama.
Gordana Obuskovic et al., Liquid membrane-based CO2 reduction in a breathing apparatus, Journal of Membrane Science, vol. 389, Elsevier B.V., Nov. 10, 2011, pp. 424-434, Amsterdam, Netherlands.
Gregory W. Konat et al., Toxicity of Compound A to C6 Rat Glioma Cells, Metabolic Brain Disease, vol. 18, No. 1, Plenum Publishing Corporation, May 17, 2003, pp. 11-15, New York City, New York.
J. P. H. Fee et al., Molecular sieves: an alternative method of carbon dioxide removal which does not generate compound A during simulated low-flow sevoflurane anaesthesia, Anaesthesia, vol. 50, The Association of Anaesthetists of Great Britain and Ireland, 1995, pp. 841-845, London, United Kingdom.
Jens Soukup et al., State of the art: Sedation concepts with volatile anesthetics in critically Ill patients, Journal of Critical Care, vol. 24, Elsevier B.V., 2009, pp. 535-544, Amsterdam, Netherlands.
Jerome Berton et al., AnaConDa Reflection Filter: Bench and PatientEvaluation of Safety and Volatile Anesthetic Conservation, Anesthesia & Analgesia Journal, International Anesthesia Research Society, Jan. 2007, pp. 130-134, San Francisco, California.
Jian-Gang Lu et al., Membrane contactor for CO2 absorption applying amino-acid salt solutions, Desalination, vol. 249, Elsevier B.V., Oct. 4, 2009, pp. 498-502, Amsterdam, Netherlands.
Jing-Liang Li et al., Review of CO2 absorption using chemical solvents in hollow fiber membrane contactors, Separation and Purification Technology, vol. 41, Elsevier B.V., Sep. 22, 2004, pp. 109-122, Amsterdam, Netherlands.
Juergen Caro et al., Zeolite Membranes—Status and Prospective, Advances in Nanoporous Materials, vol. 1, Elsevier B.V., 2009, pp. 1-96, Amsterdam, Netherlands.
"K. Kneifel et al., Hollow fiber membrane contactor for air humidity control:Modules and membranes, Journal of Membrane Science, vol. 276, Elsevier B.V., Jan. 6, 2006, pp. 241-251, Amsterdam, Netherlands."
Katja Simons et al., Gas-liquid membrane contactors for CO2 removal, Journal of Membrane Science, vol. 340, Elsevier B.V., May 30, 2009, Amsterdam, Netherlands.
Klaus-Viktor Peinemann et al., Membranes for Life Sciences, Membrane Technology, pp. 56-64, vol. 1, available online at www.wiley-vch.de.
L. Perhag et al., The Reflector: a new method for saving anaesthetic vapours, British Journal of Anesthesia, vol. 85, The Board of Management and Trustees of the British Journal of Anaestheia, Apr. 11, 2000, pp. 482-486, London, United Kingdom.
"L. W. Sturesson et al., Carbon dioxide rebreathing with the anaestheticconserving device, AnaConDa, British Journal of Anaesthesia, vol. 109, Apr. 13, 2012, pp. 279-283, Oxford, United Kingdom."
Lloyd M. Roberston, The upper bound revisited, Journal of Membrane Science, vol. 320, Elsevier B.V., Apr. 22, 2008, pp. 390-400, Amsterdam, Netherlands.
M. Derwall et al., Xenon: recent developments and future perspectives, Minerva Anestesiol, vol. 75, No. 1-2, Società Italiana di Anestesia, Apr. 3, 2008, pp. 37-45, Rome, Italy.
M. M. R. F. Struys et al., Production of compound A and carbon monoxide in circle systems: an in vitro comparison of two carbon dioxide absorbents, Anesthesiology, vol. 59, American Society of Anesthesiologists, 2004, pp. 584-589, Schaumburg, Illinois.
M. Yamakage et al., Performance of four carbon dioxide absorbents in experimental and clinical settings, Anaesthesia, vol. 64, The Association of Anaesthetists of Great Britain and Ireland, Sep. 26, 2008, pp. 287-292, London, United Kingdom.
Marcelo Zaldini Hernandes et al., Halogen Atoms in the Modern Medicinal Chemistry: Hints for the Drug Design, Current Drug Targets 2010, Bentham Science Publishers Ltd., 2010, pp. 1-12, Sharjah, United Arab Emirates.
Marshall B. Dunning III et al., Sevoflurane Breakdown Produces Flammable Concentrations of Hydrogen, Anesthesiology, vol. 106, American Society of Anesthesiologists, Jan. 2007, pp. 144-148, Schaumburg, Illinois.
Marta Maria Cabral Campo Dos Santos, Carbon Molecular Sieve Membranes for Gas Separation: Study, Preparation and Characterization, Chemical Engineering Department, Faculty of Engineering, University of Porto, 2009, pp. 1-238, Portugal.
Melissa Boesenberg, Anaesthetic gases: environmental impact and alternatives, Department of Anaesthesia, Groote Schuur Hospital, 2011, pp. 345-348, Cape Town, South Africa.
Michael J. Laster et al., Temperatures in Soda Lime During Degradation of Desflurane, Isoflurane, and Sevoflurane by Desiccated Soda Lime, Anesthesia & Analgesia Journal, International Anesthesia Research Society, 2005, pp. 753-757, San Francisco, California.
Montoya, J. Patrick, Using Hollow Fiber Membranes to Separate Gases from Liquid and Gaseous Streams, Membrane Gas Exchange, 2010, pp. 1-7, MedArray Inc.
P. S. Kumar et al., New absorption liquids for the removal of CO2 from dilute gas streams using membrane contactors, Chemical Engineering Science, vol. 57, Elsevier B.V., 2002, Amsterdam, Netherlands.
Pauline Stone et al., Anaesthesia for elderly patients, Anaesthesia and Intensive Care Medicine Journal, Elsevier B.V., 2007, pp. 361-364, Amsterdam, Netherlands.
Raphael Idem et al., Preface for the Special Issue on the Capture of Carbon Dioxide From Industrial Sources: Technological Developments and Future Opportunities, Industrial & Engineering Chemistry Research, vol. 45, University of Regina, 2006, p. 1, Regina, Canada.

(56) References Cited

OTHER PUBLICATIONS

Robert Musiol, Stability of Inhalational Anaesthestic Agents, Anaesthesiology Intensive Therapy, Jan. 18, 2009, avaliable at http://anestezjologia.net/en/articles/item/10019/stability_of_inhalational_anaesthestic_agents.

S. Lagorsse, Xenon recycling in an anaesthetic closed-system using carbon molecular sieve membranes, Journal of Membrane Science, vol. 301, Elsevier B.V., Jun. 2, 2007, pp. 29-38, Amsterdam, Netherlands.

Stijn Schauvliege et al., Influence of two different ventilation modes on the function of an anaesthetic conserving device in sevoflurane anaesthetized piglets, Veterinary Anaesthesia and Analgesia, vol. 36, Association of Veterinary Anaesthetists, 2009, p. 230-238, Hertfordshire, United Kingdom.

Susan M. Ryan et al., Global Warming Potential of Inhaled Anesthetics: Application to Clinical Use, Anesthesia & Analgesia, vol. 111, No. 1, International Anesthesia Research Society, Jul. 2010, pp. 92-98, San Francisco, California.

Bocklage, et al., Setting the Tidal Volume In Adults Receiving Mechanical Ventilation: Lessons Learned From Recent Investigations.

Miller's Anesthesia, Eighth Edition, vol. 1 Chapter 27, Inhaled Anesthetics: Pulmonary Pharmacology, p. 693.

MacIntyre, Neil R. and Ho, Li-Ing, Effects of Initial Flow Rate and Breath Termination Criteria on Pressure Support Ventilation, Chest, 1991; 99: 134-8.

Bonmarchand, et al., Increased Initial Flow Rate Reduces Inspiratory Work of Breathing During Pressure Support Ventilation in Patients with Exacerbation of Chronic Obstructive Pulmonary Disease, Intensive Care Med (1996) 22: 1147-1154.

Christoph Wiesenack, et al., In Vivo Uptake and Elimination of Isoflurane by Different Membrane Oxygenators during Cardiopulmonary Bypass, Anesthesiology, vol. 97, No. 1, Jul. 1, 2002, pp. 133-138, Philadelphia, US.

Supplementary European Search Report dated Aug. 3, 2016.

\* cited by examiner

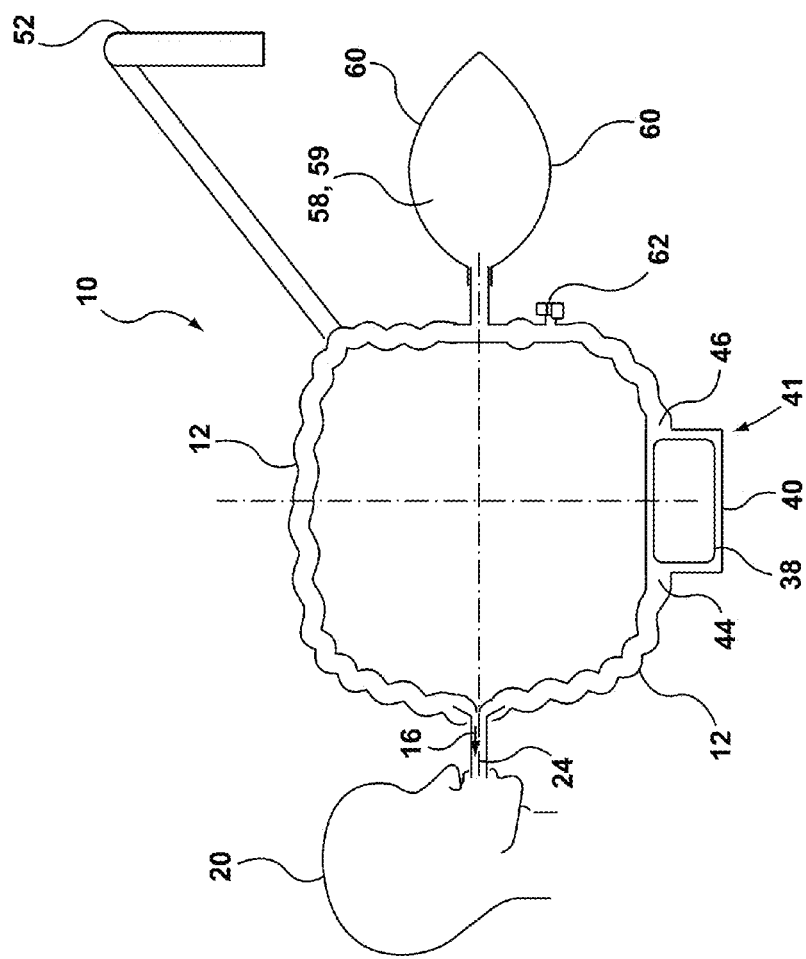

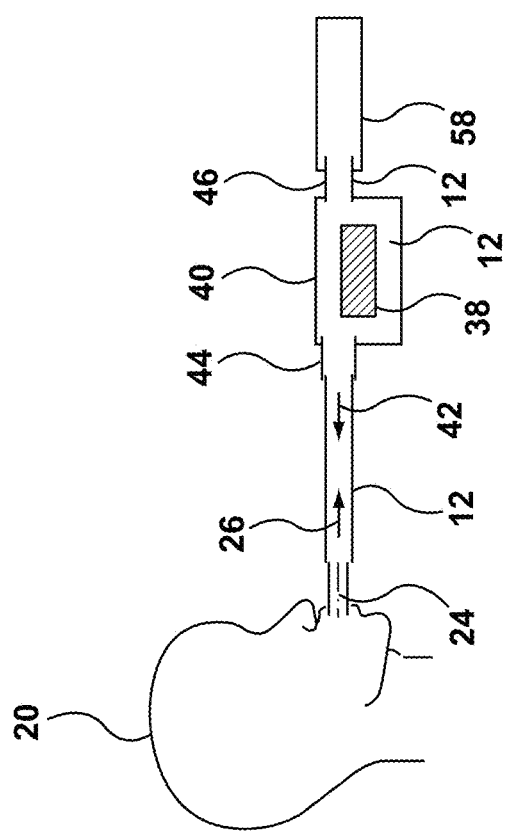

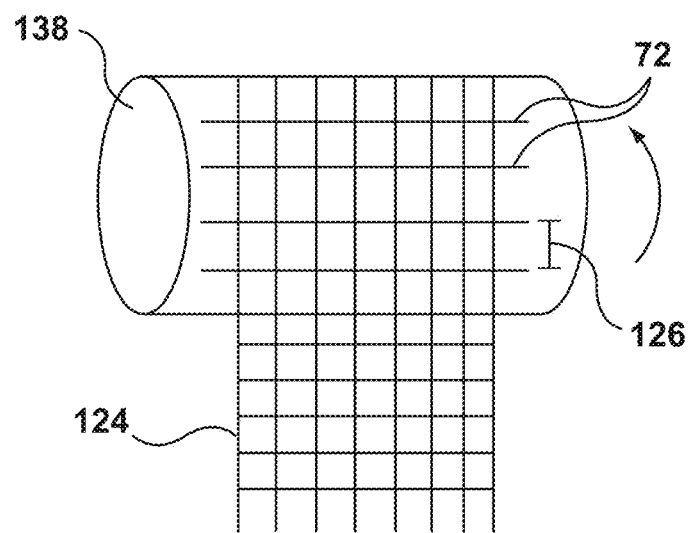
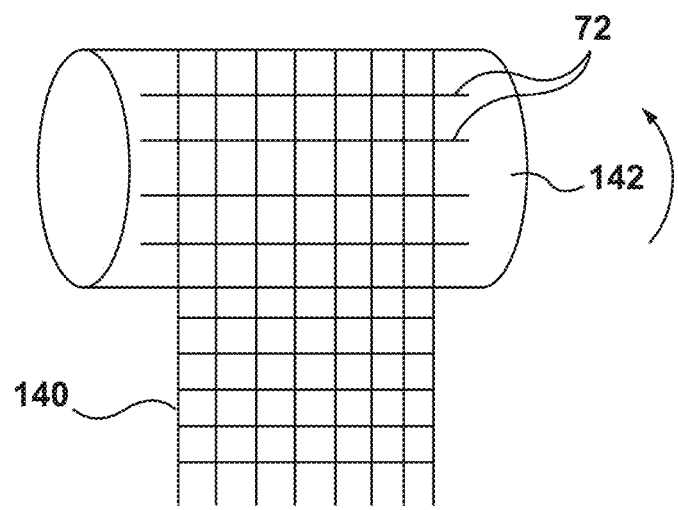
FIG. 23

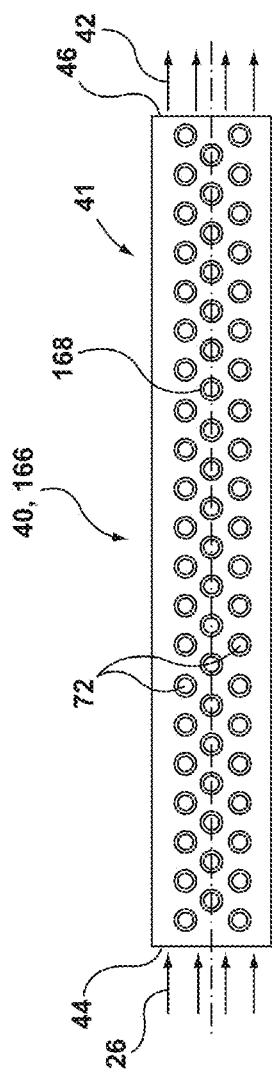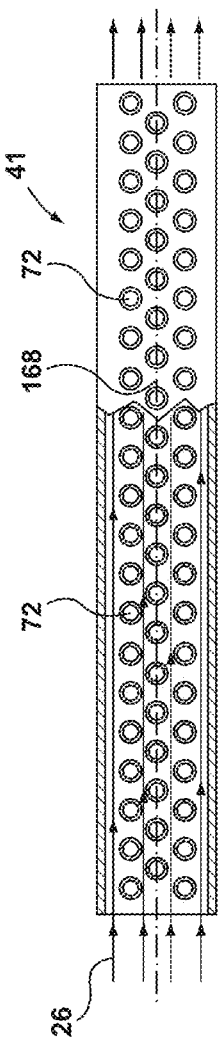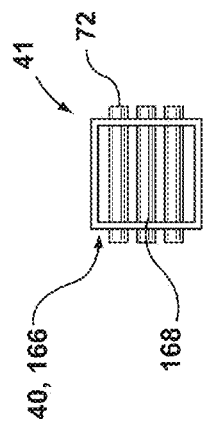

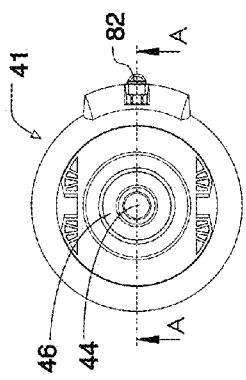
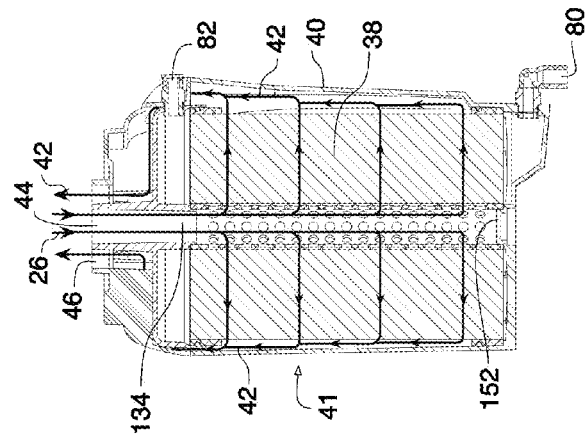
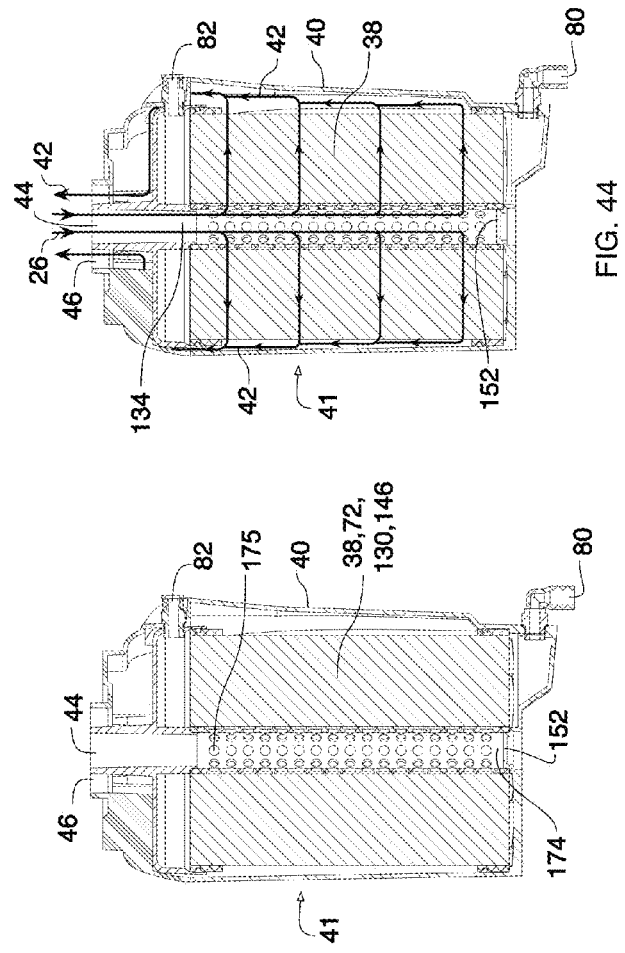

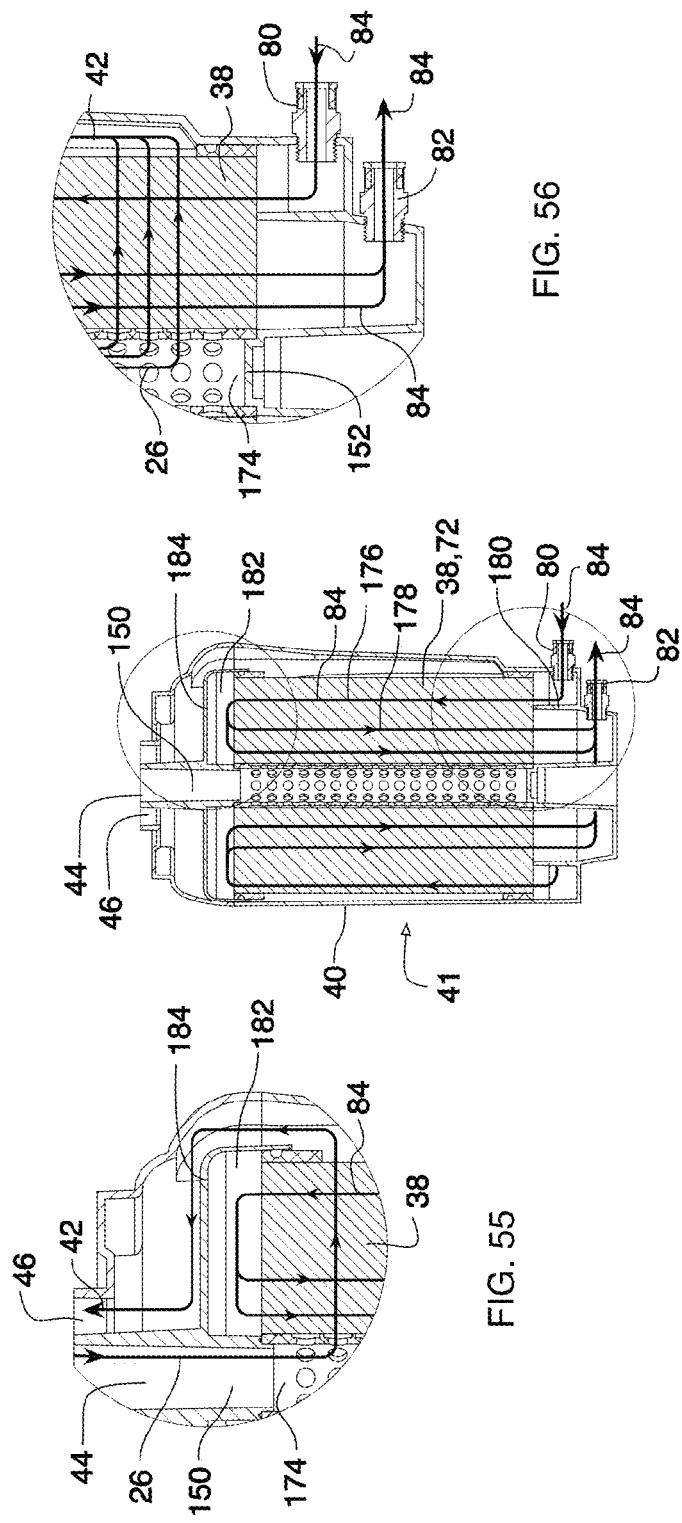

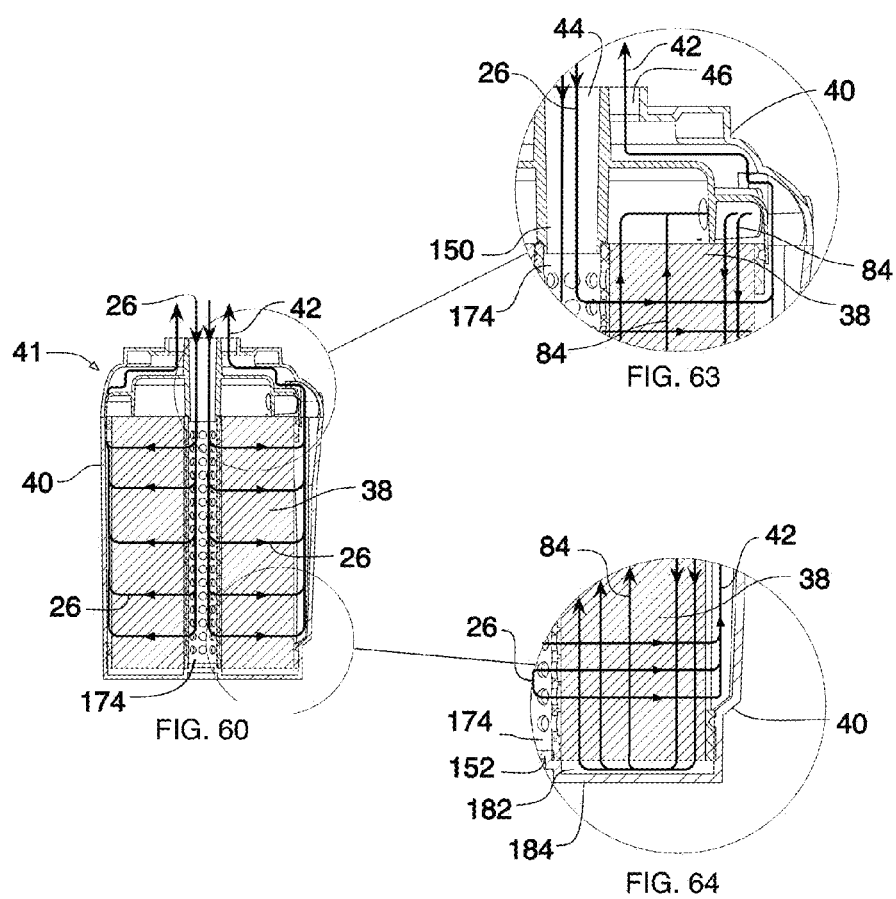

ANESTHETIC CIRCUIT HAVING A HOLLOW FIBER MEMBRANE

FIELD

This invention relates to an anesthetic circuit to anesthetize a patient. This invention also relates to a method of using an anesthetic circuit to anesthetize a patient and a fluid separation apparatus connectable to an anesthetic circuit.

INTRODUCTION

Anesthetic agents are commonly used to anesthetize a patient during a medical procedure. To keep the stress level low and relax the patient, the patient has to be asleep for many medical procedures. Anesthetic circuit systems wherein anesthetic agent is partially re-used after being delivered to the patient are known in the art. The benefit is that less anesthetic agent is used. This is financially beneficial due to the relatively high cost of most anesthetic agents. The use of less anesthetic agents may also be good for the environment since some anesthetic agents, such as the halogenated hydrocarbon sevoflurane, for example, are greenhouse fluids.

Carbon dioxide is formed in the cell and is released though the alveoli of the lungs during expiration at a level of around 5% of the expiratory fluid mixture. The concentration at the end of expiration is called the end tidal concentration of carbon dioxide ($etCO_2$). The inspiratory level of carbon dioxide is normally below 0.5%. Having excessive levels of carbon dioxide in the blood of the patient will decrease the pH value of the blood (acidosis) and will, if not treated properly, affect the patient's brain activity and may eventually lead to unconsciousness and death.

When the patient inhales the anesthetic agent in a fluid mixture, the anesthetic agent passes through the alveoli of the lungs into the patient's blood. The patient exhales a fluid mixture comprising, among other components, exhaled anesthetic, exhaled oxygen and exhaled carbon dioxide. Due to the operation of the human's lungs, the carbon dioxide content of the exhaled fluid mixture is higher than that of the inhaled fluid mixture. Furthermore, the oxygen content of the exhaled fluid mixture is lower than that of the inhaled fluid mixture in most cases. To be able to re-use the fluid mixture (containing the exhaled anesthetic fluid), the carbon dioxide of the exhaled fluid mixture must be lowered to levels suitable for re-inhalation.

Anesthetic circuits aimed at decreasing the amount of carbon dioxide fluid re-inhaled by the patient are known in the art. Some in the industry have focused on decreasing the carbon dioxide content in the exhaled mixture, along with trying to preserve exhaled oxygen and exhaled anesthetic agent within the anesthetic circuit for re-inhalation. Their desire to preserve exhaled oxygen fluid is premised on the notion that oxygen needs to be provided as part of the inhaled mixture in an appropriate level to keep the oxygen saturation in the patient's blood high enough to allow for proper metabolism. Many publications focus on separating or binding the $CO_2$ specifically and therefore separate it from the fluid mixture containing the anesthetic agent.

Some conventional anesthetic circuits use carbon dioxide absorbers to reduce exhaled carbon dioxide within the anesthetic circuit. In some cases, soda lime or baralyme, for example, are used. Sevoflurane and other anesthetic vapors can react with these carbon dioxide absorbers to produce harmful chemicals such as compound A. Compound A has been found to have negative effects such as nephro and cerebo toxic effects.

In other conventional systems, a membrane impregnated with a substance that is chemically reactive with carbon dioxide (and, in some cases, anesthetic agent) is used to reduce the amount of exhaled carbon dioxide from an anesthetic circuit. For example, membranes comprising amino acids or amine groups that are chemically reactive with carbon dioxide are known in the art. The reactive sites may degrade or become contaminated over time, which requires the membrane to be disposed of and replaced.

Specific examples of selective membranes known in the art that separate an anesthetic from at least one other fluid include: United States Patent No. 2007/0017516 to Schmidt, United States Patent Application No. 2010/0031961 to Schmidt, United States Patent No. 2009/0126733 to Kulkarni et al. and The Journal of Membrane Science Article "Xenon recycling in an anaesthetic closed-system using carbon molecular sieve membranes" (S. Lagorsse, F. D. Magalhães, A. Mendes; Journal of Membrane Science 301 (2007) 29-38).

There exists a need for an improved anesthetic circuit in which exhaled anesthetic agent can be effectively retained and re-circulated to the patient.

SUMMARY

The following summary is provided to introduce the reader to the more detailed discussion to follow. The summary is not intended to limit or define the claims.

According to one broad aspect of this disclosure, an anesthetic circuit for treating a patient is provided. The anesthetic circuit comprises:

a flow passage;

an anesthetic agent inlet in fluid communication with the flow passage for introducing an external anesthetic agent into the flow passage;

at least one fluid port in fluid communication with the flow passage for providing at least the external anesthetic agent to the patient, wherein the at least one fluid port receives an exhaled fluid mixture from the patient, the exhaled fluid mixture comprising an exhaled oxygen, an exhaled carbon dioxide and an exhaled anesthetic agent, the flow passage being in fluid communication with the at least one fluid port for receiving the exhaled fluid mixture from the at least one fluid port;

a membrane comprising a plurality of hollow fibers, the membrane being in fluid communication with the flow passage, configured to receive the exhaled fluid mixture from the at least one fluid port, and at least partially impervious to the exhaled anesthetic agent to at least partially retain the exhaled anesthetic agent in the flow passage after the exhaled fluid mixture contacts the membrane, wherein the membrane is pervious to the exhaled carbon dioxide such that the membrane has an exhaled carbon dioxide-to-exhaled anesthetic agent selectivity of greater than 1, the exhaled fluid mixture contacts the membrane wherein the membrane separates a portion of the exhaled carbon dioxide from the exhaled fluid mixture to leave a modified fluid mixture in the flow passage having a lower amount of the exhaled carbon dioxide than the exhaled fluid mixture, and the at least one fluid port is configured to receive the modified fluid mixture from the membrane and provide at least the modified fluid mixture to the patient; and a fluid inlet for introducing an external fluid into the flow passage to be added to the modified fluid mixture provided to the patient.

In some cases, the exhaled anesthetic agent is an exhaled molecular anesthetic agent. In some embodiments, the membrane comprises at least one polymeric material. In some cases, the membrane is pervious to the exhaled oxygen such that the membrane has an exhaled oxygen-to-exhaled molecular anesthetic agent selectivity of greater than 1.

In some embodiments, the membrane is pervious to the exhaled oxygen such that the membrane has an exhaled oxygen-to-exhaled anesthetic agent selectivity of at least 2.

In some cases, the membrane has an exhaled carbon dioxide-to-exhaled anesthetic agent selectivity of at least 2.

In some embodiments, the membrane is entirely made up of polymeric material.

In some cases, the membrane is configured such that a secondary oxygen located external to the flow passage passes through the membrane and into the flow passage.

In some embodiments, the anesthetic circuit further comprises an external oxygen source for enriching the external fluid with external oxygen. In other embodiments, an external oxygen source introduces external oxygen directly into the anesthetic circuit.

In some cases, the anesthetic circuit further comprises at least one flow generator for facilitating flow of the exhaled fluid mixture and the modified fluid mixture through the flow passage.

In some embodiments, the anesthetic circuit further comprises a turbulence-inducing component in the flow passage to create a turbulent flow of the exhaled fluid mixture at the membrane to increase contact between the exhaled fluid mixture and the membrane.

In some cases, the exhaled anesthetic agent is a volatile anesthetic agent and the membrane is at least partially impervious to the volatile anesthetic agent.

In some embodiments, the exhaled anesthetic agent is a polyhalogenated ether.

In some cases, the exhaled anesthetic agent includes at least one of sevoflurane, isoflurane or desflurane.

In some embodiments, the exhaled anesthetic agent has a molecular weight of greater than 168 g/mol.

In some cases, a carbon dioxide absorbing material is located on a side of the membrane that is external to the flow passage. In some cases, the membrane separates the carbon dioxide absorbing material from the exhaled anesthetic agent retained in the flow passage to impede the exhaled anesthetic agent from contacting the carbon dioxide absorbing material. In some cases, the carbon dioxide absorbing material comprises at least one of: soda lime, alkanolime, alkanolamine, amino compounds, alkali salts of amino acids, glycine, DL-alanine, beta-alanine, serine, threonine, isoleucine, DL-valine, piperazine-2-carboxilic acid, proline, arginine, gamma-aminobutyric acid, ornithine, potassium glycinate, potassium threonate, taurine, creatine and histidine.

In some embodiments, the anesthetic circuit of the exhaled fluid mixture comprises a metabolic product including acetaldehyde, acetone, ethane, ethylene, hydrogen, isoprene, methane, methylamine or pentane. In some cases, the membrane is pervious to the metabolic product and the exhaled fluid mixture contacts the membrane to leave a modified fluid mixture in the flow passage having a lower amount of the metabolic product than the exhaled fluid mixture.

In some cases, the membrane is a polyhalocarbon membrane. More specifically, in some cases, the membrane is a polymethylpentene membrane. In some cases, the membrane is a polysiloxane membrane. More specifically, in some cases, the membrane is a polydimethyl siloxane membrane.

In some embodiments, the membrane is a dense membrane.

In some cases, the membrane is an asymmetric membrane comprising the plurality of hollow fibers and the plurality of hollow fibers have at least one wall comprising a porous support layer and a dense layer.

In some embodiments, the membrane comprises a glassy polymer, a polymeric size selective membrane or a composite polymer membrane.

In some cases, the membrane is completely inert with respect to the exhaled carbon dioxide and is free of any amino acids.

In some embodiments, the at least one fluid port comprises an exit outlet in fluid communication with the flow passage for providing at least the external anesthetic agent to the patient and an entry inlet separate from the exit outlet for receiving the exhaled fluid mixture from the patient. The flow passage may be in fluid communication with the entry inlet for receiving the exhaled fluid mixture from the entry inlet. The exit outlet may be configured to receive the modified fluid mixture from the membrane and provide the modified fluid mixture to the patient.

In some cases, the at least one fluid port includes only one fluid port. The one fluid port may be in fluid communication with the flow passage for providing at least the external anesthetic agent to the patient. The one fluid port may receive the exhaled fluid mixture from the patient. The flow passage may be in fluid communication with the one fluid port for receiving the exhaled fluid mixture from the one fluid port. The one fluid port may be configured to receive the modified fluid mixture from the membrane and provide the modified fluid mixture to the patient.

In some cases, each hollow fiber has an outer wall having a first side that contacts the exhaled fluid mixture and permits at least a portion of the exhaled carbon dioxide to flow into the hollow fiber, and an opposing second side at which the modified fluid mixture is provided after at least a portion of the exhaled carbon dioxide flows into the hollow fiber.

In some embodiments, the hollow fibers permit a sweep fluid to pass therethough to facilitate the transport of at least a portion of the exhaled carbon dioxide into the hollow fibers, and the hollow fibers direct the sweep fluid and the exhaled carbon dioxide out of the flow passage.

In some cases, the membrane is located in a membrane housing. The exhaled fluid mixture may enter the membrane housing via a housing inlet. The membrane housing may direct the exhaled fluid mixture into contact with the membrane, to provide the modified fluid. The membrane housing may direct the modified fluid mixture out of the housing via the housing inlet. Alternatively, the membrane housing may direct the modified fluid mixture out of the housing via a housing outlet.

In some cases, the housing exit and the housing inlet are separate and concentric with one another.

In some embodiments, the plurality of hollow fibers are spaced from one another and are arranged substantially parallel to an entry direction of the exhaled fluid mixture when the exhaled fluid mixture initially contacts the plurality of hollow fibers.

In some cases, the plurality of hollow fibers are spaced from one another and are arranged substantially perpendicular to a flow direction of the exhaled fluid mixture when the exhaled fluid mixture initially contacts the plurality of hollow fibers.

In some embodiments, the membrane comprises the plurality of hollow fibers wound into a cylindrical roll defining a hollow inner core having an open end to receive the exhaled fluid mixture therein.

In some embodiments, the plurality of hollow fibers are formed in at least a first planar mat. In some cases, the plurality of hollow fibers in the first planar mat are spaced from and substantially parallel with one another.

In some cases, the first planar mat is rolled together in a cylindrical roll forming concentric layers of substantially parallel hollow fibers.

In some embodiments, the rolled first planar mat defines a hollow inner core having a first open end to receive the exhaled fluid mixture and a closed second end.

In some cases, the plurality of hollow fibers are formed in the first planar mat and second planer mat, the plurality of hollow fibers in the second planar mat are spaced from and substantially parallel with one another, the first planar mat is overlapped with the second planar mat, and the overlapped first and second planar mats are rolled together in a cylindrical roll forming concentric layers of the hollow fibers.

In some embodiments, the first planar mat is overlapped with the second planar mat so that the hollow fibers of the first planar mat are oriented at an angle to the hollow fibers of the second planar mat to provide concentric layers of cross wound hollow fibers.

In some cases, the rolled first planar mat and second planar mat define a hollow inner core having a first open end configured to receive the exhaled fluid mixture.

In some embodiments, the plurality of hollow fibers are formed in planar discs stacked upon one another, and the hollow fibers in each planar disc are spaced from one another and oriented substantially parallel to one another in a corresponding disc direction.

In some cases, the corresponding disc direction for a first disc is different than the corresponding disc direction for any other disc stacked directly adjacent to the first disc.

In some embodiments, the corresponding disc direction for all of the stacked discs is substantially the same.

In some cases, the plurality of hollow fibers of the membrane are located in an elongate channel having a longitudinal centerline.

In some embodiments, the plurality of hollow fibers are arranged substantially perpendicular to the longitudinal centerline of the elongate channel.

In some cases, the elongate channel has a substantially rectangular cross-section in a plane perpendicular to the longitudinal centerline.

In some embodiments, the elongate channel has a rounded cross-section in a plane perpendicular to the longitudinal centerline.

In some cases, the elongate channel has a cross-section in a plane perpendicular to the longitudinal centerline having a cross-sectional area of approximately 300 $mm^2$ to 20,000 $mm^2$.

In some embodiments, the longitudinal centerline of the elongate channel is curved.

In some embodiments, the plurality of hollow fibers of the membrane are located in a membrane housing, the hollow fibers are randomly packed (randomly oriented) in to the membrane housing.

In some cases, the exhaled fluid mixture enters the housing via a housing inlet, the membrane housing directs the exhaled fluid mixture into contact with the membrane to provide the modified fluid mixture, and the membrane directs the modified fluid mixture out of the membrane housing via a housing outlet.

In some cases, the plurality of hollow fibers of the membrane are located in a housing and at least one hollow fiber has a corresponding shape and orientation that is different than a corresponding shape and orientation of another hollow fiber.

In some cases, each hollow fiber has a corresponding shape and orientation that is different than a corresponding shape and orientation of all other hollow fibers in the housing.

According to another broad aspect of this disclosure, a fluid separation apparatus fluidly connectable to an anesthetic circuit is provided, the anesthetic circuit having a flow passage for transporting an exhaled fluid mixture containing at least exhaled anesthetic agent and exhaled carbon dioxide through the flow passage. The fluid separation apparatus comprises:

a membrane having a plurality of hollow fibers, wherein the membrane is at least partially impervious to the exhaled anesthetic agent to at least partially retain the exhaled anesthetic agent in the flow passage after the exhaled fluid mixture contacts the membrane, and the membrane is more pervious to the exhaled carbon dioxide than the exhaled anesthetic agent such that the membrane has an exhaled carbon dioxide-to-exhaled anesthetic agent selectivity of greater than 1; and a membrane housing containing the membrane therein, wherein the housing is configured to receive the exhaled fluid mixture via a housing inlet, the membrane housing directs the exhaled fluid mixture into contact with the membrane, to provide a modified fluid mixture having a lower amount of the exhaled carbon dioxide than the exhaled fluid mixture, the membrane housing directs the modified fluid mixture out of the membrane housing via a housing outlet, the at least one hollow fiber permits a sweep fluid to pass therethough to facilitate the transport of at least a portion of the exhaled carbon dioxide into the at least one hollow fiber, and the membrane housing has at least one sweep inlet to receive the sweep fluid therethrough and at least one sweep outlet to expel the sweep fluid from the membrane housing.

In some embodiments, the membrane housing is configured to direct the sweep gas received from the sweep inlet through a first portion of the plurality of hollow fibers in a first sweep direction and subsequently through a second portion of the plurality of hollow fibers in a second sweep direction substantially opposite to the first sweep direction before the sweep gas exists the housing via the sweep outlet. In some cases, the first portion of the plurality of hollow fibers is radially outward of the second portion of the plurality of hollow fibers.

In some embodiments, the sweep fluid comprises at least nitrogen gas, the membrane is at least partially impervious to the nitrogen gas and pervious to the exhaled carbon dioxide such that the membrane has an exhaled carbon dioxide-to-nitrogen gas selectivity of greater than 1.

In some cases, the membrane comprises the plurality of hollow fibers wound into a cylindrical roll defining a hollow inner core having an open end to receive the exhaled fluid mixture.

In some embodiments, the membrane is pervious to a metabolic product in the exhaled fluid mixture and the exhaled fluid mixture contacts the membrane to leave a modified fluid mixture in the flow passage having a lower amount of the metabolic product than in the exhaled fluid mixture. Metabolic products may include acetaldehyde, acetone, ethane, ethylene, hydrogen, isoprene, methane, methylamine or pentane.

In some cases, the membrane housing comprises an inner shaft inserted into the hollow inner core of the membrane, and the inner shaft has a plurality of apertures therein to direct the exhaled fluid mixture through the apertures and into the membrane. In some cases, the apertures located further away from the membrane housing inlet are generally smaller than the apertures located closer to the membrane housing inlet.

According to another broad aspect of this disclosure, a method is provided for anesthetic treatment of a patient. The method comprises:
introducing an external anesthetic agent towards and into the patient via a flow passage;
directing an exhaled fluid mixture comprising an exhaled oxygen, an exhaled carbon dioxide and an exhaled anesthetic agent away from and out of the patient into the flow passage;
advancing the exhaled fluid mixture through the flow passage towards and into contact with a membrane comprising a plurality of hollow fibers in fluid communication with the flow passage;
transferring more of the exhaled carbon dioxide than the exhaled anesthetic agent from the exhaled fluid mixture through the membrane and out of the flow passage after the exhaled fluid mixture contacts the membrane to leave a modified fluid mixture in the flow passage, wherein the modified fluid mixture has a lower concentration of the exhaled carbon dioxide than the exhaled fluid mixture; and
advancing the modified fluid mixture through the flow passage toward the patient to provide at least the modified fluid mixture to the patient.

In some cases, the method for anesthetic treatment of a patient further comprises:
transferring exhaled oxygen through the membrane after the exhaled fluid mixture contacts the membrane to leave a modified fluid mixture in the flow passage, wherein the membrane has an exhaled oxygen-to-exhaled anesthetic agent selectivity of greater than 1, and wherein
the external anesthetic agent comprises a molecular anesthetic agent,
the exhaled anesthetic agent is an exhaled molecular anesthetic agent, and
the plurality of hollow fibers are made at least partially of polymeric material.
advancing the modified fluid mixture through the flow passage toward the patient to provide at least the modified fluid mixture to the patient.

According to yet another broad aspect of this disclosure, a membrane is provided for selectively separating fluids from an exhaled fluid mixture in an anesthetic circuit, the exhaled fluid mixture containing at least exhaled anesthetic agent and exhaled carbon dioxide. The membrane comprises:
a plurality of hollow fibers, wherein
the membrane is at least partially impervious to the exhaled anesthetic agent to at least partially retain the exhaled anesthetic agent in the flow passage after the exhaled fluid mixture contacts the membrane, and
the membrane is more pervious to the exhaled carbon dioxide than the exhaled anesthetic agent such that the membrane has an exhaled carbon dioxide-to-exhaled anesthetic agent selectivity of greater than 1.

In some embodiments, the membrane comprises the plurality of hollow fibers wound into a cylindrical roll defining a hollow inner core having an open end to receive the exhaled fluid mixture therein.

In some embodiments, the membrane comprises the plurality of hollow fibers formed in planar discs stacked upon one another. In some cases, the hollow fibers in each planar disc are spaced from one another and oriented substantially parallel to one another in a corresponding disc direction.

According to yet another broad aspect of this disclosure, the use of a membrane, as described herein, is provided to selectively separate fluids from an exhaled fluid mixture in an anesthetic circuit, the exhaled fluid mixture containing at least exhaled anesthetic agent and exhaled carbon dioxide.

According to yet another broad aspect of this disclosure, the use of a fluid separation apparatus, as described herein, is provided to selectively separate fluids from an exhaled fluid mixture in an anesthetic circuit, the exhaled fluid mixture containing at least exhaled anesthetic agent and exhaled carbon dioxide.

DRAWINGS

Reference is made in the description of various embodiments to the accompanying drawings, in which:

FIG. 1 is a side view of an exemplary anesthetic circuit in accordance with an embodiment of the invention;

FIG. 1*a* is a side view of the exemplary anesthetic circuit of FIG. 1, showing an alternative position for the membrane housing;

FIG. 2 is a side view of the anesthetic circuit of FIG. 1 further comprising an external oxygen source;

FIG. 3*a* is a side view of an anesthetic circuit in accordance with an alternative embodiment having a compressible member;

FIG. 3*b* is a side view of an anesthetic circuit in accordance with yet another embodiment having a compressible member;

FIG. 3*c* is a side view of an anesthetic circuit in accordance with an alternative embodiment having a bellow;

FIG. 3*d* is a side view of an anesthetic circuit in accordance with an alternative embodiment having an exemplary flow generator;

FIG. 3*e* is a side view of the anesthetic circuit of FIG. 3*b*, showing an alternative position of the membrane housing;

FIG. 3*f* is a side view of an anesthetic circuit in accordance with an alternative embodiment including an exemplary flow generator;

FIG. 3*g* is a side view of the anesthetic circuit of FIG. 3*f* showing an alternative position of the membrane housing;

Figure 12:
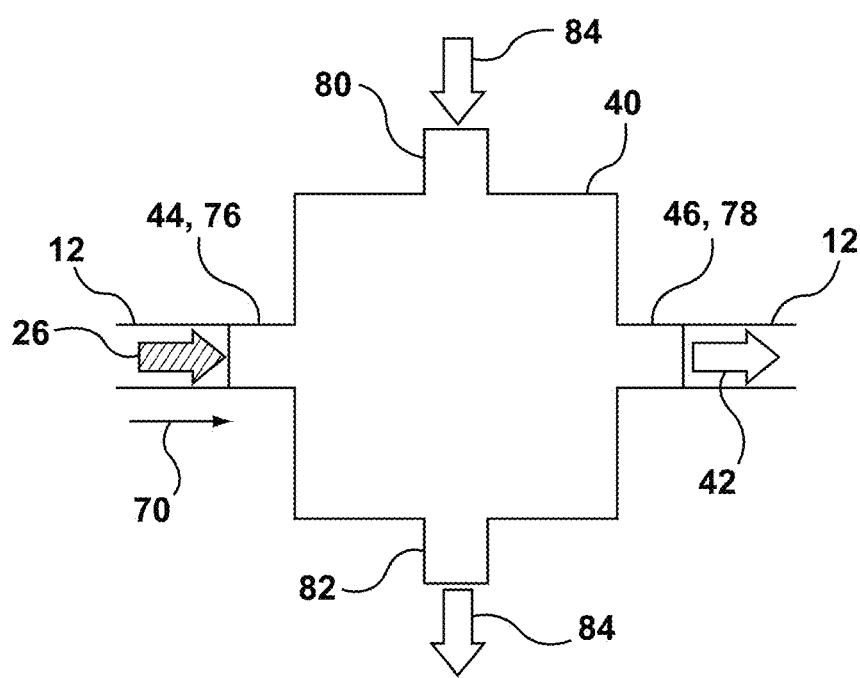
Figure 13:
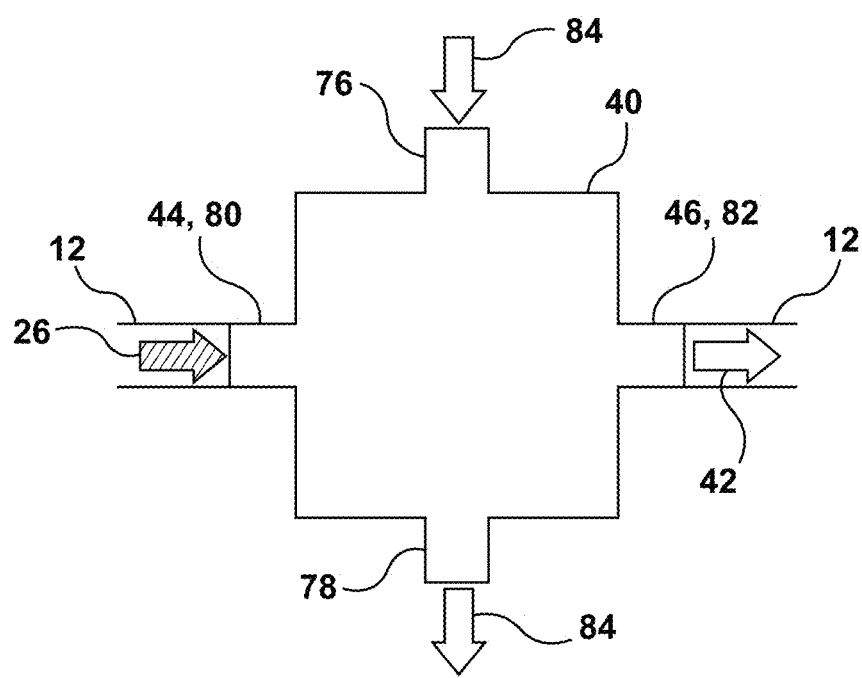
Figure 14:
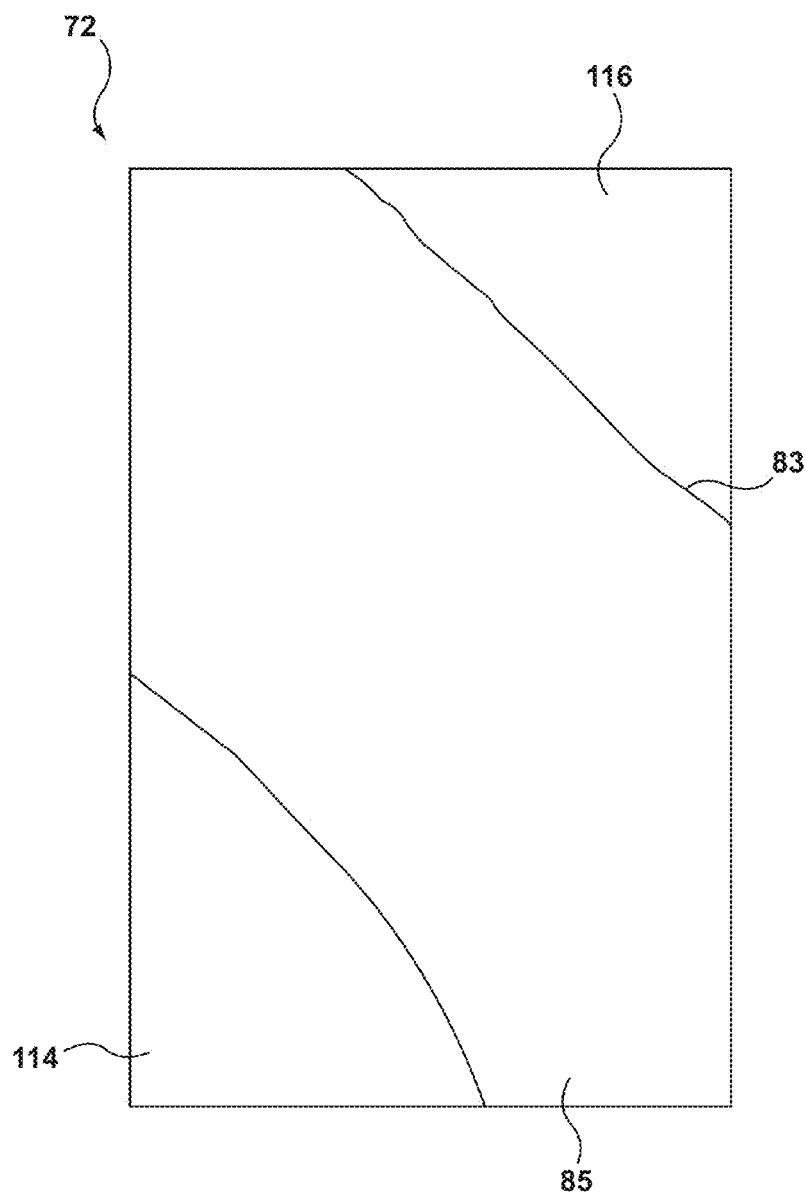
Figure 15:
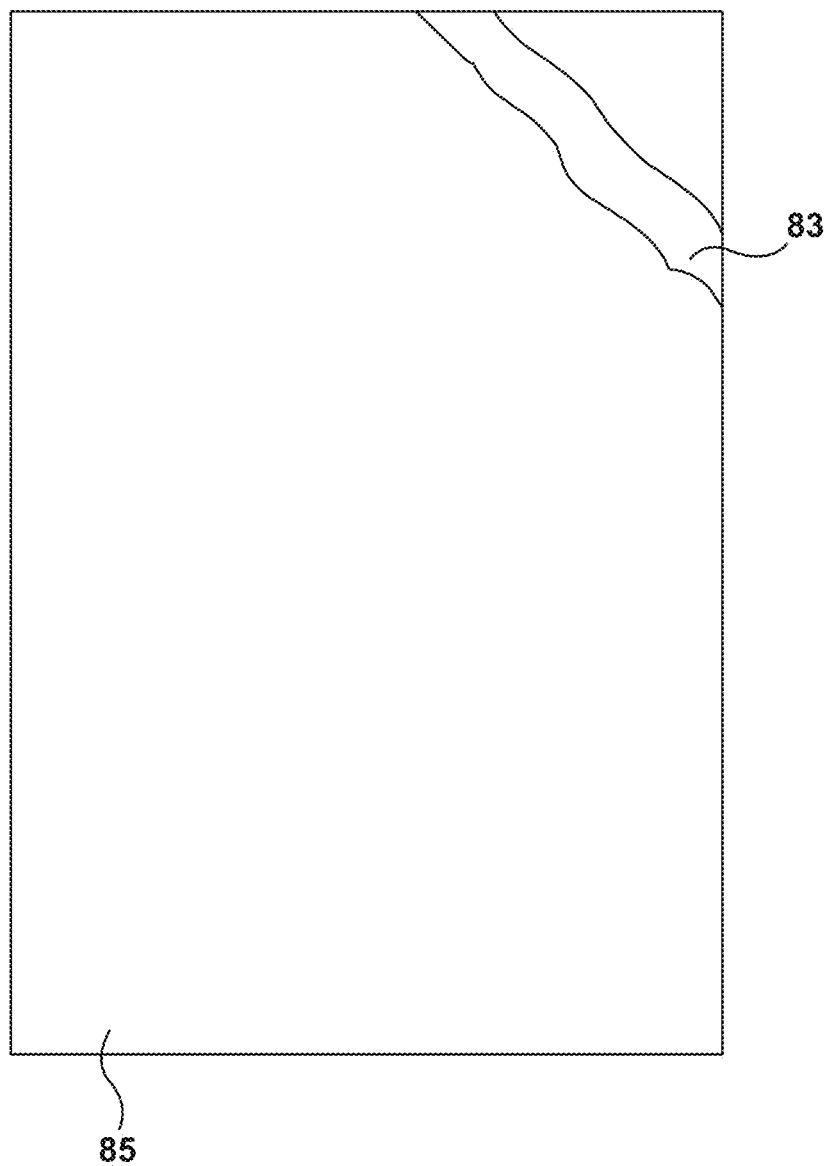
Figure 16:
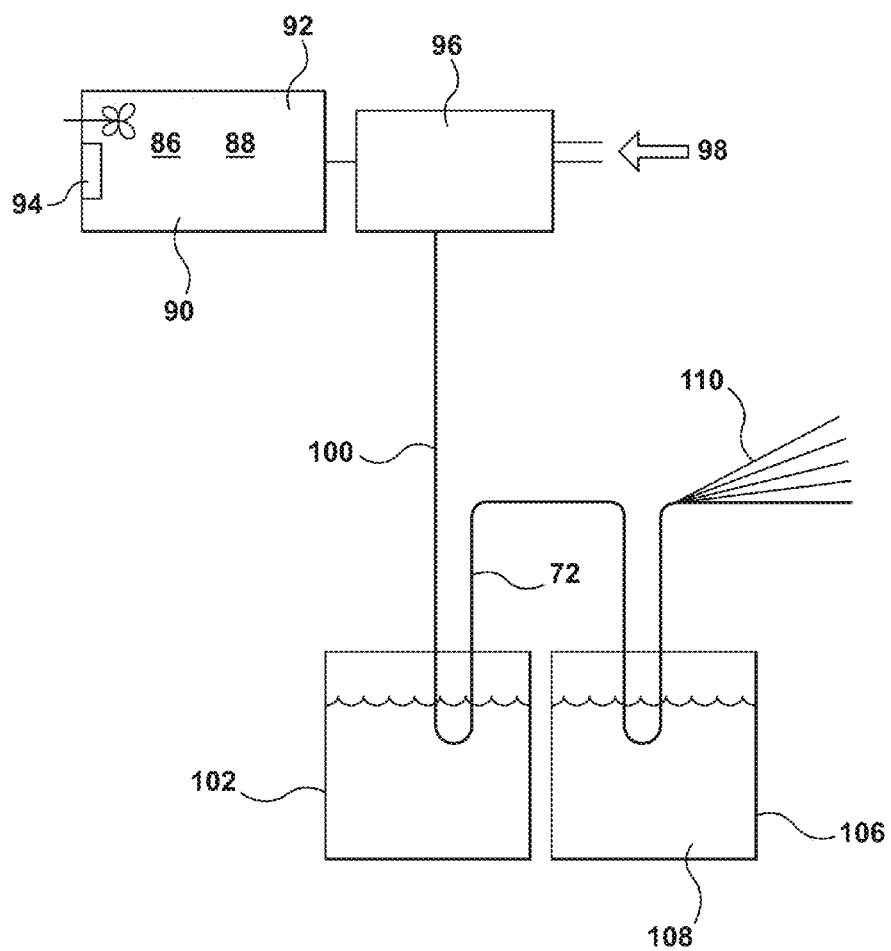
Figure 17:
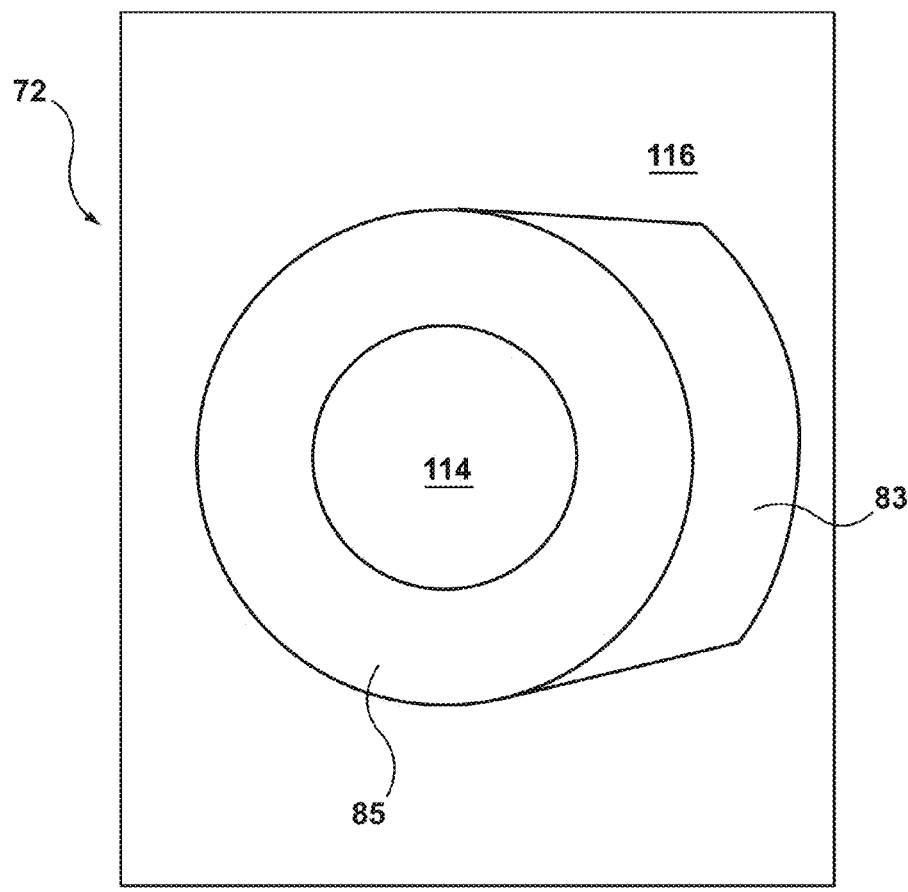
Figure 18:
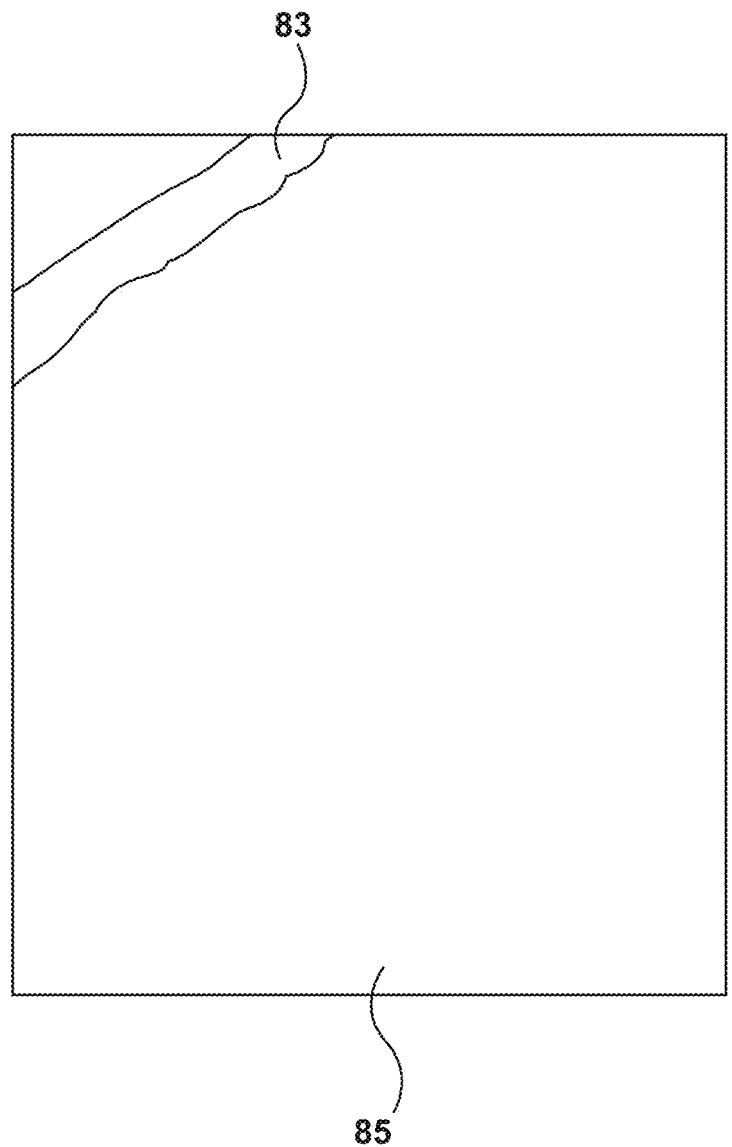
Figure 19:
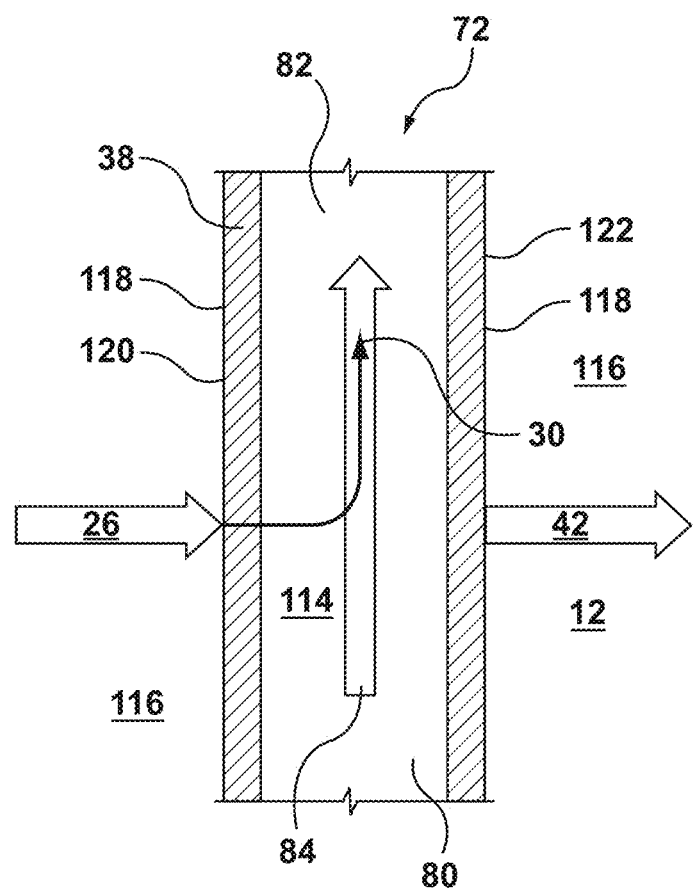
Figure 20:
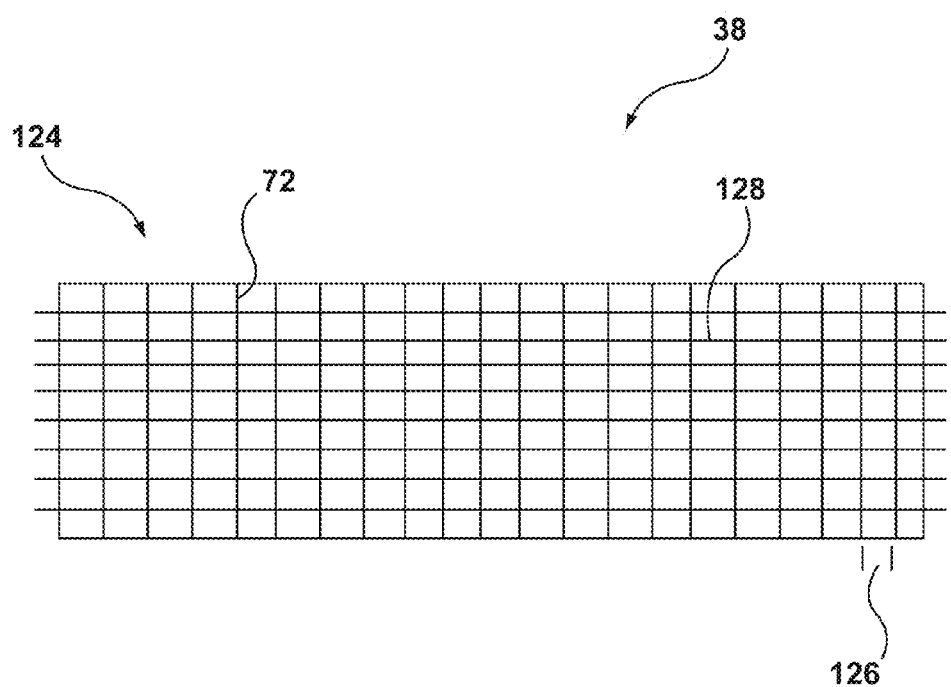
Figure 21:
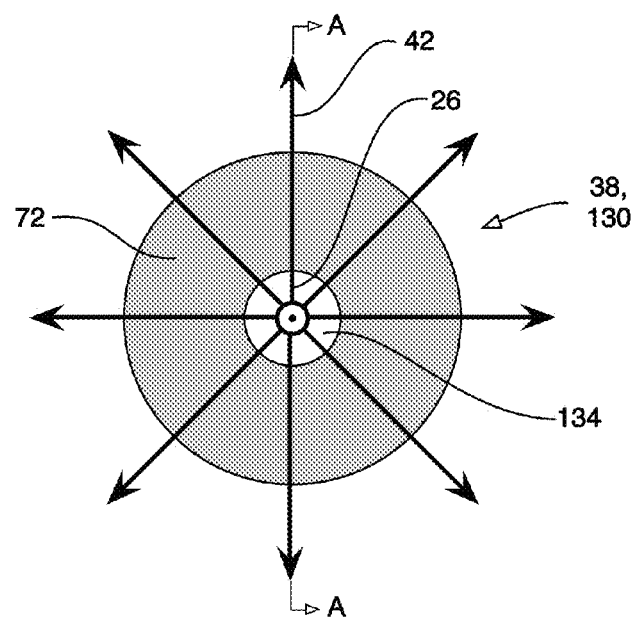
Figure 21:
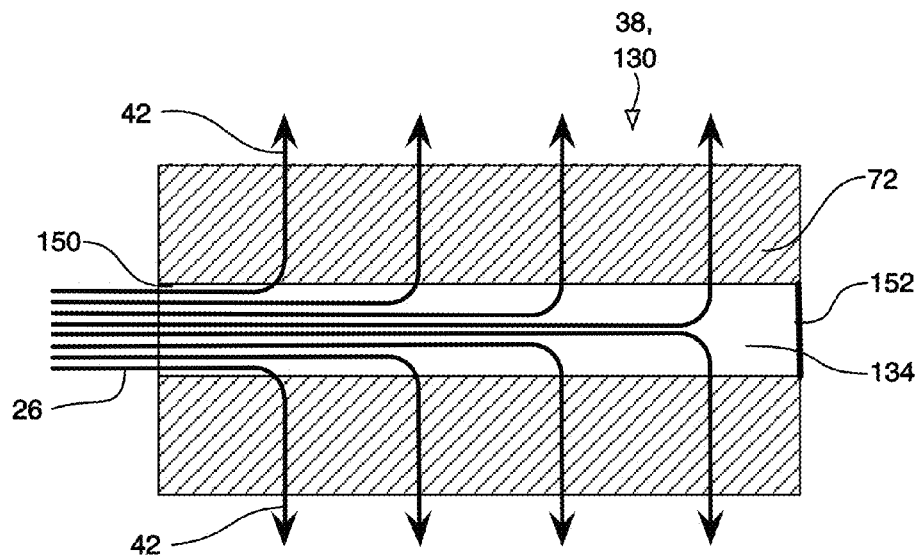
Figure 21C:
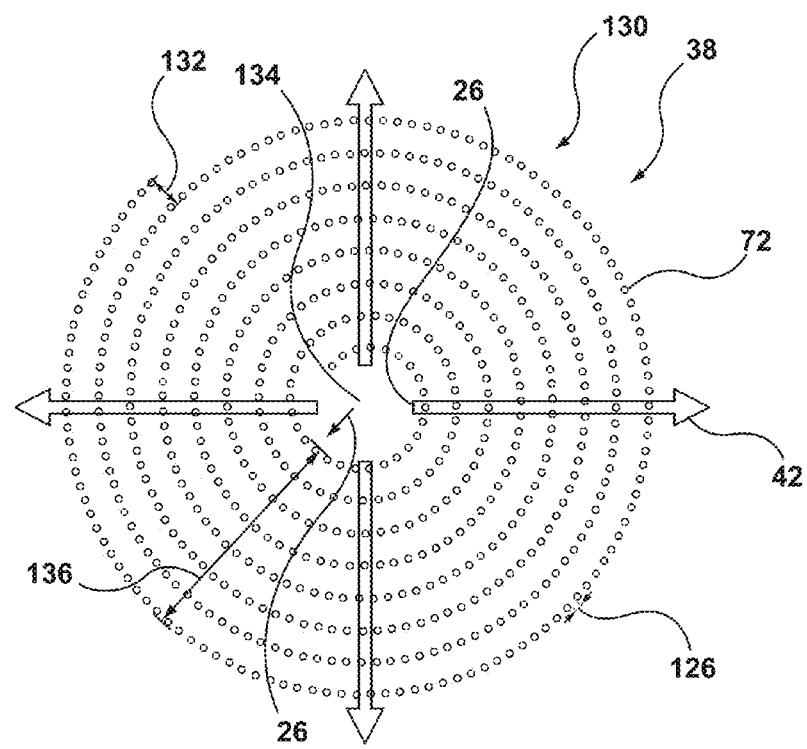
Figure 22:
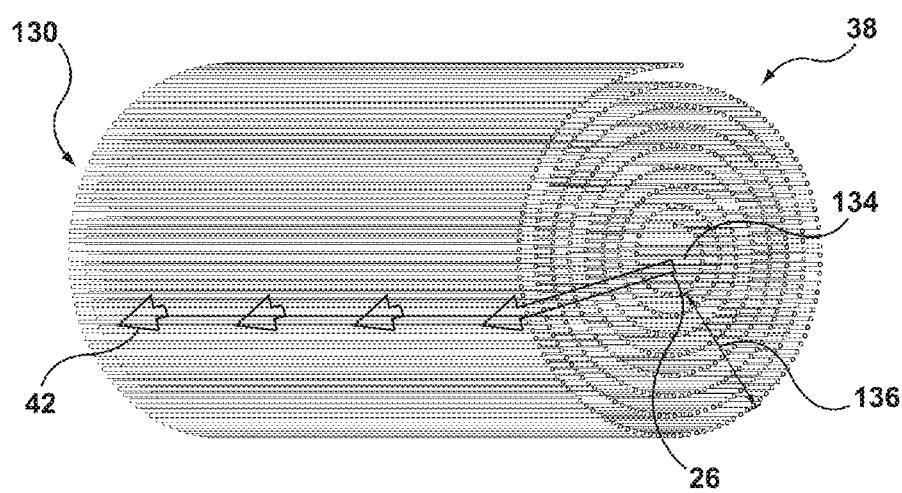
Figure 24:
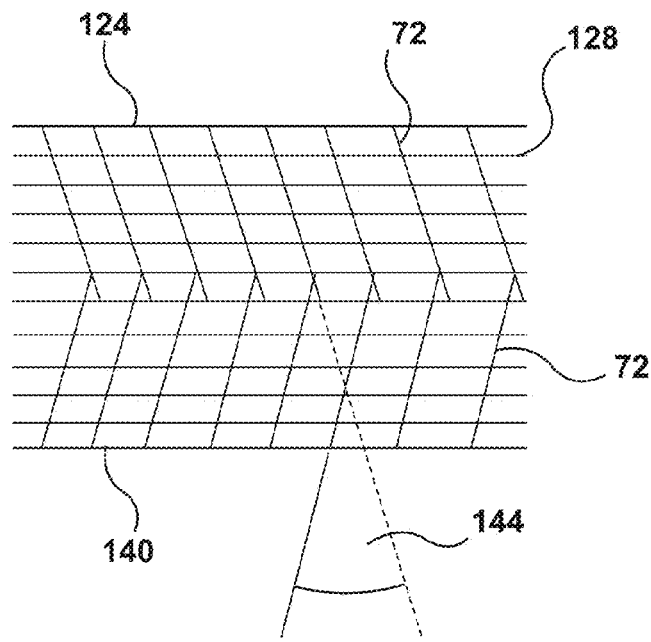
Figure 25:
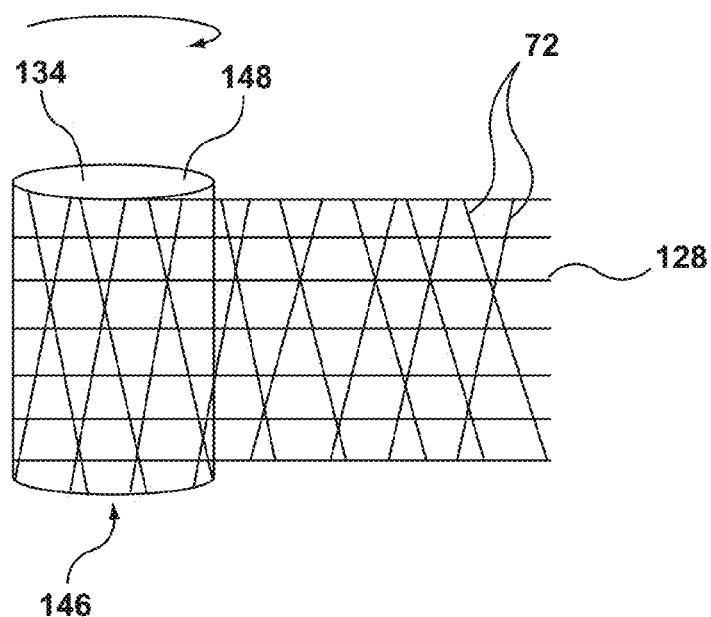
Figures 26, 27:
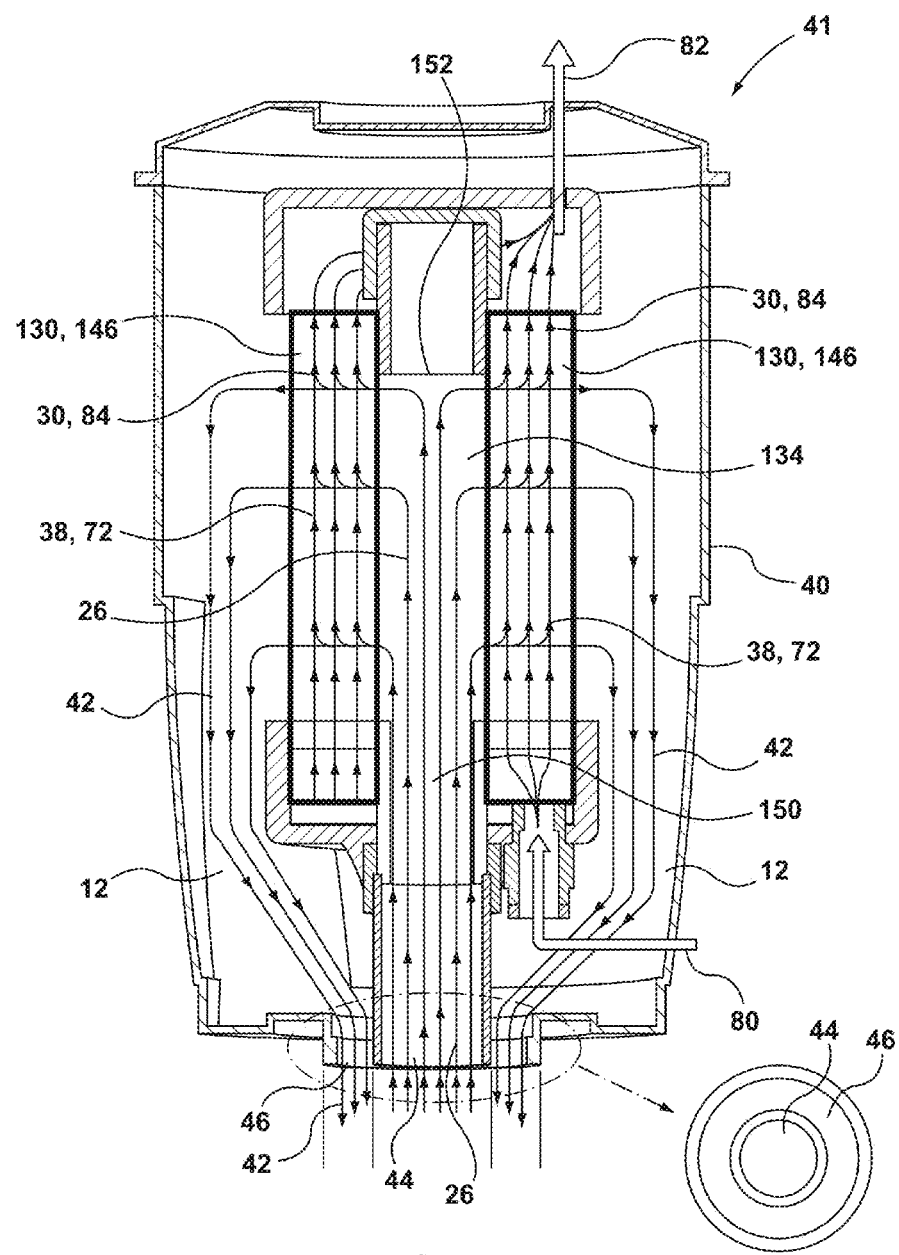
Figure 28:
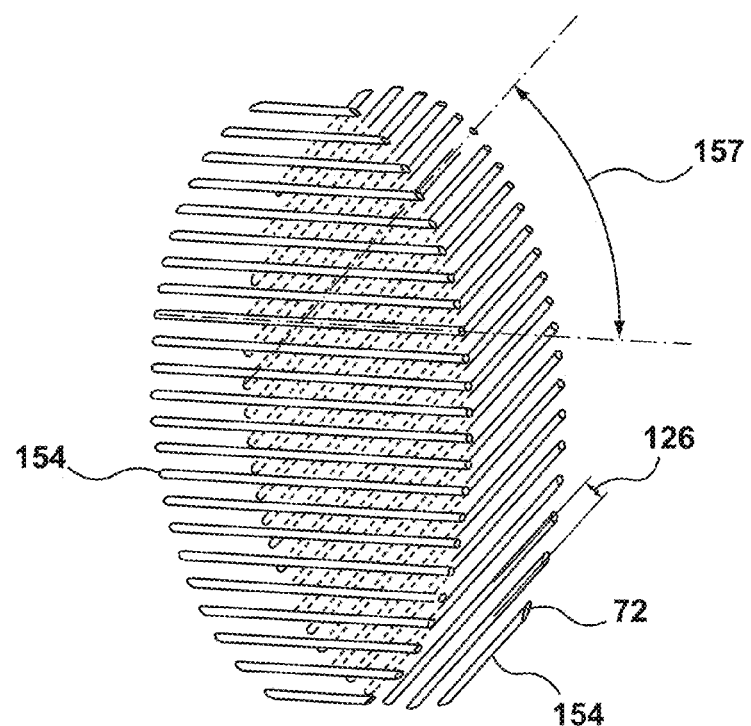
Figure 29:
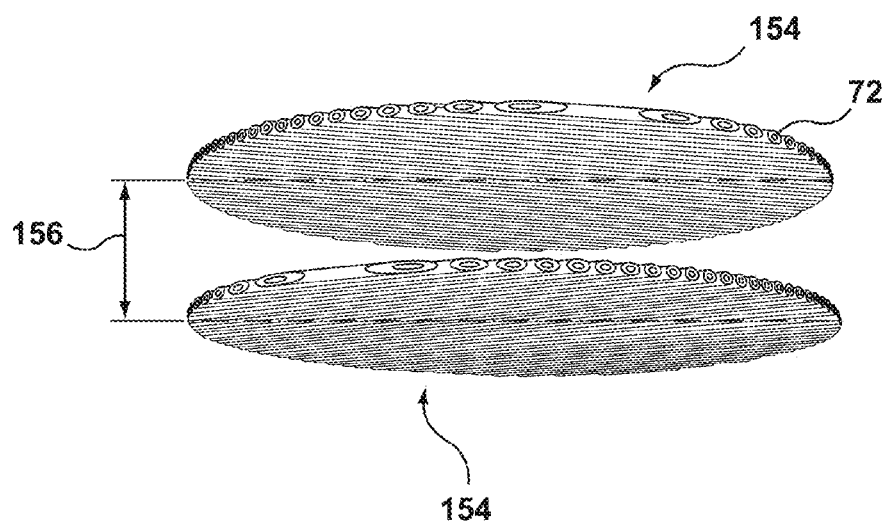
Figure 30:
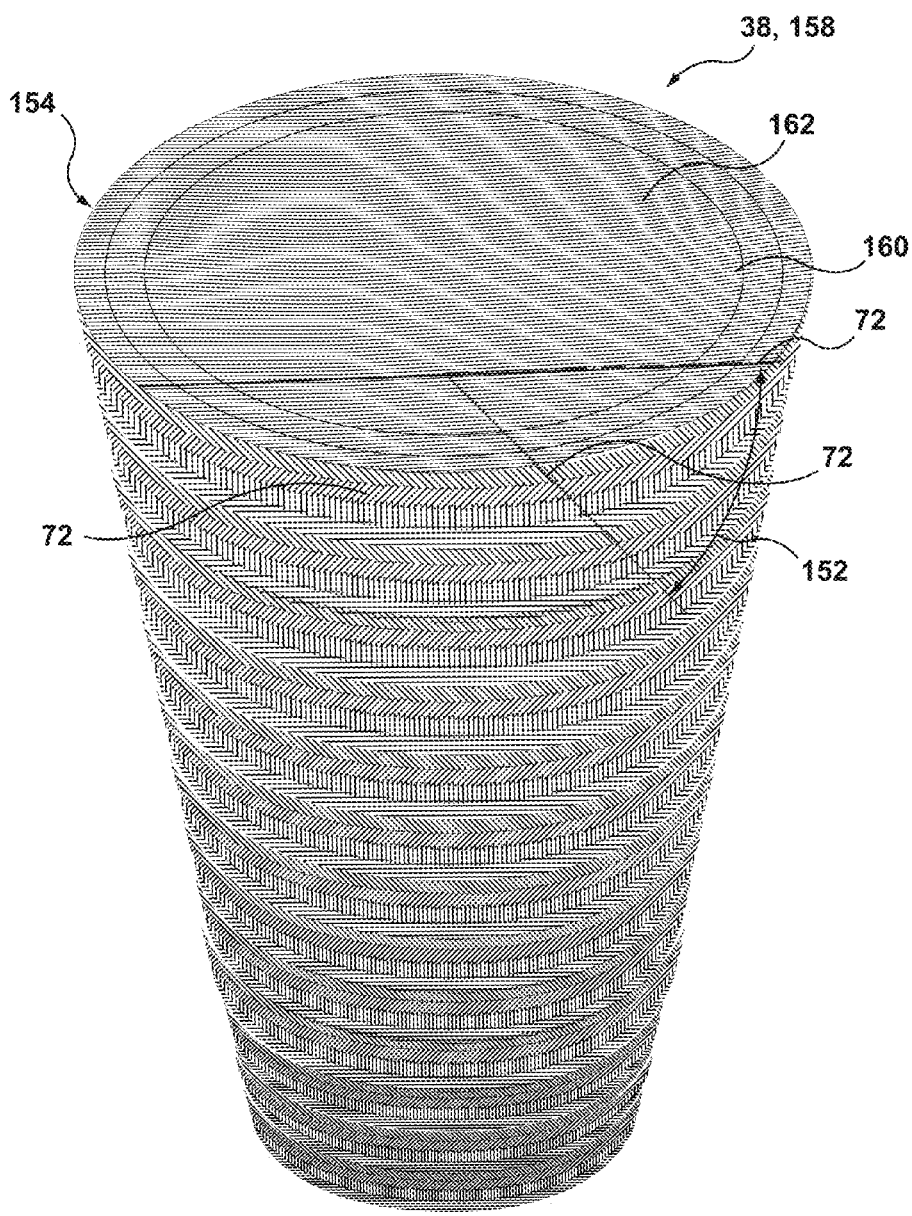
Figure 31:
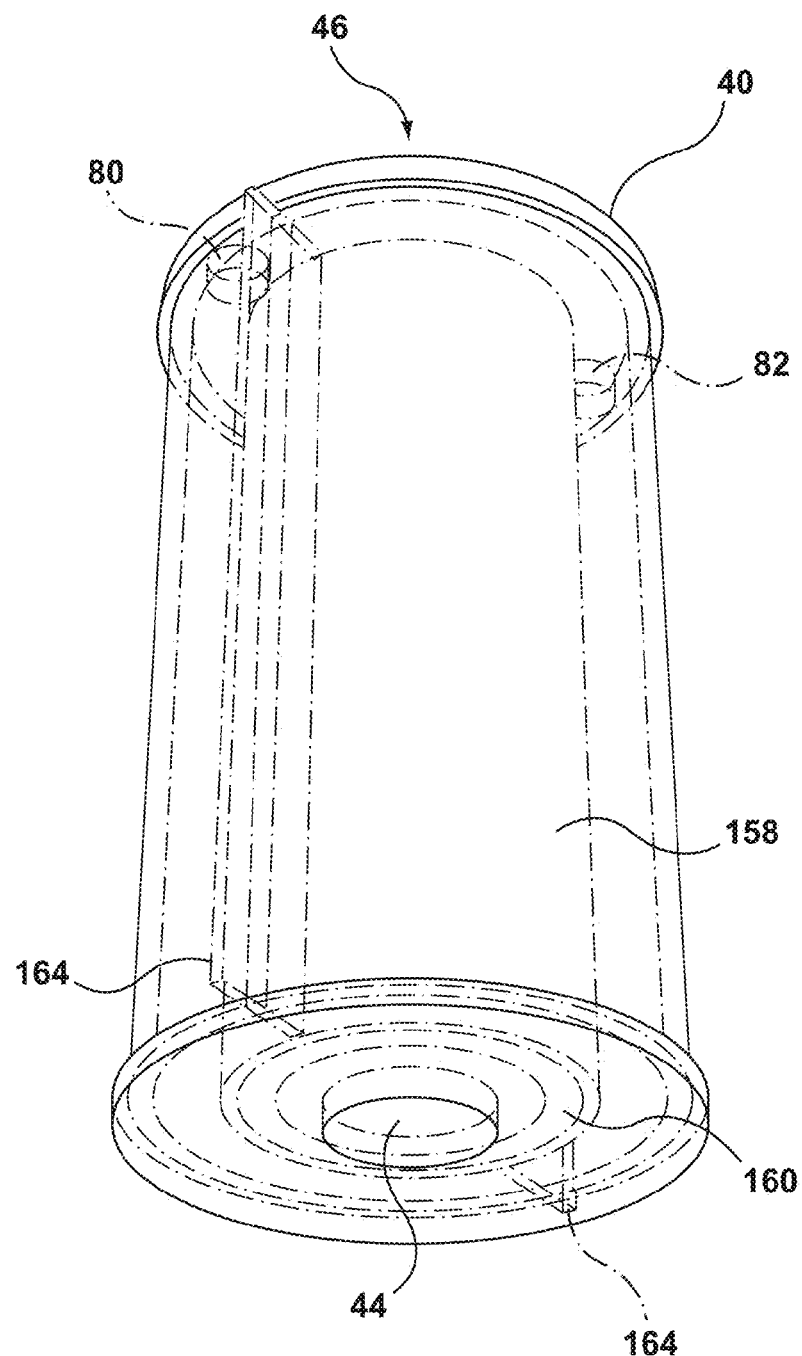
Figure 32:
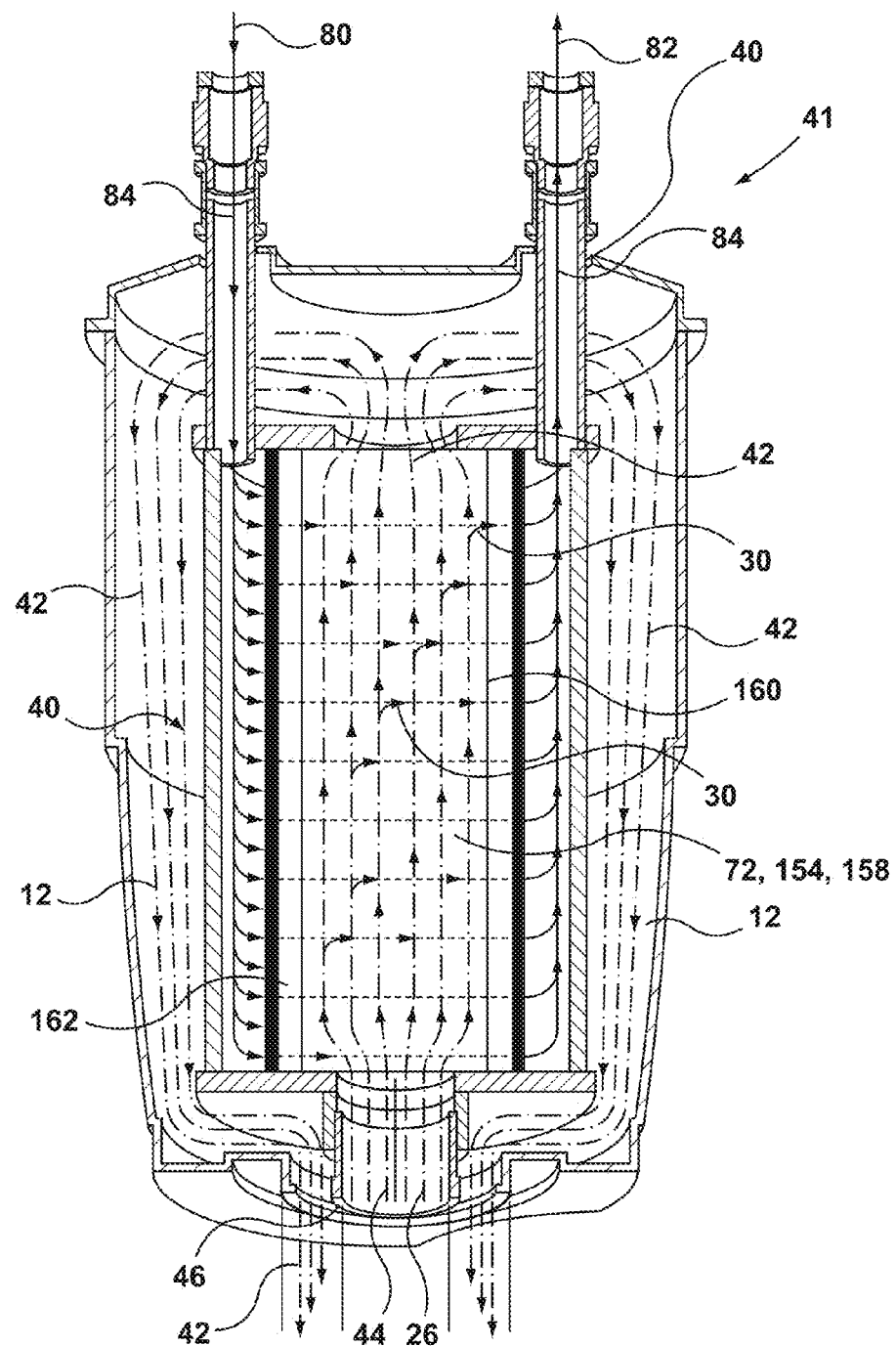
Figure 33:
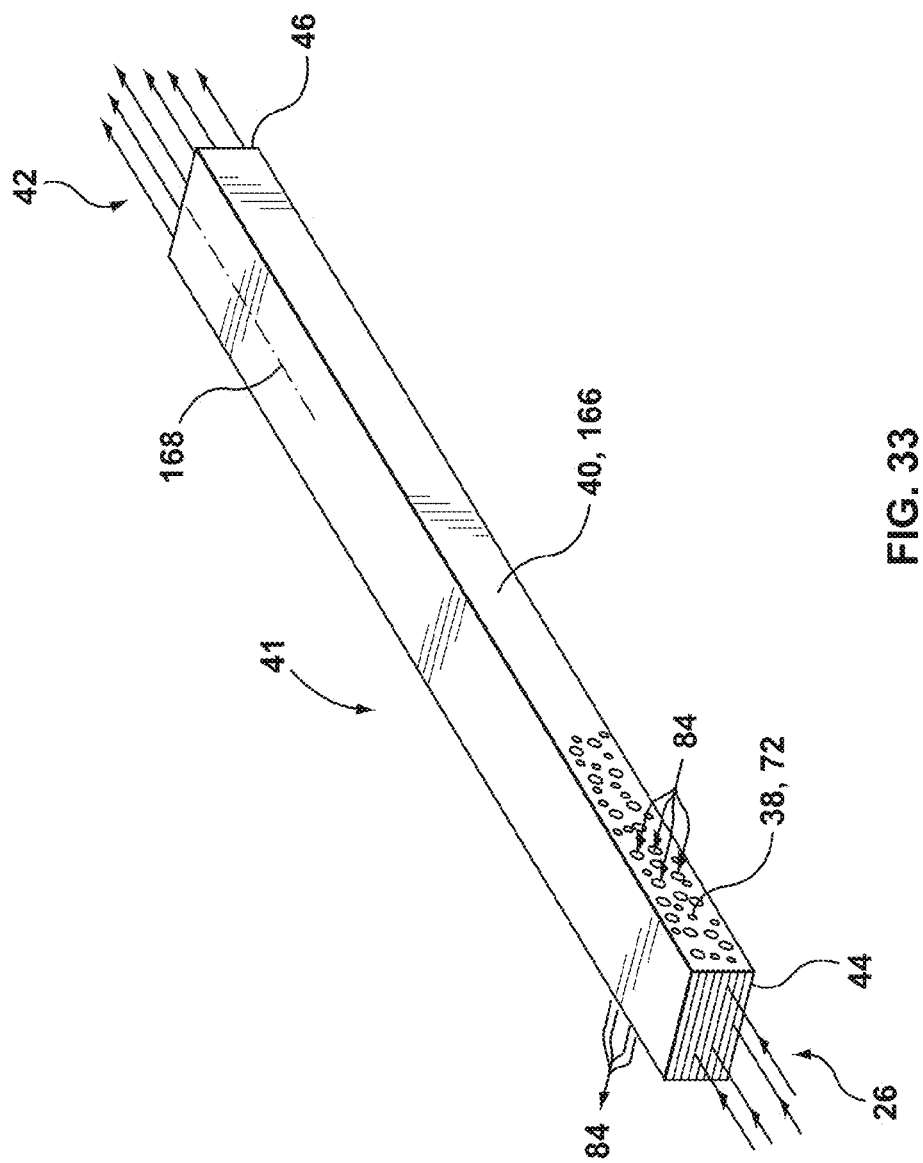

FIG. 12 provides a side view of an example oxygenator;

FIG. 13 provides a side view of the oxygenator of FIG. 12, rotated by 90° relative to the flow passage;

FIG. 14 provides a partial plan view of a hollow fiber of an exemplary OXYPLUS™ membrane;

FIG. 15 provides a partial plan view of the dense layer and porous support layer of an exemplary OXYPLUS™ membrane;

FIG. 16 provides an exemplary schematic representation of the ACCUREL™ production process;

FIG. 17 provides a plan view of an exemplary hollow fiber of an ULTRAPHOBIC™ membrane;

FIG. 18 provides a partial plan view of a dense layer and a porous support layer of an ULTRAPHOBIC™ membrane;

FIG. 19 is a cut-away side view of an exemplary hollow fiber of a membrane;

FIG. 20 is a plan view of an exemplary membrane comprising hollow fibers in a planar mat;

FIG. 21a is a cut-away top view of an exemplary cylindrical membrane comprising hollow fibers surrounding a hollow inner core;

FIG. 21b is a cut-away side view of the cylindrical membrane of FIG. 21a;

FIG. 21c is a cross-sectional view of the membrane of FIG. 20 rolled into a cylindrical membrane having parallel hollow fibers;

FIG. 22 is a perspective view of the rolled cylindrical membrane of FIG. 21c;

FIG. 23 is a perspective view of a first planar mat and a second planar mat rolled as a step to form a rolled cylindrical membrane having cross wound fibers;

FIG. 24 is a planar view of the first planar mat and second planar mat of FIG. 23 pulled into a trapezoidal shape and overlapped with one another as a step to form a rolled cylindrical membrane having cross wound fibers;

FIG. 25 is a perspective view of the first planar mat and the second planar mat of FIG. 24 combined to form a rolled cylindrical membrane having cross wound fibers;

FIG. 26 is a cut-away side view of an exemplary fluid separation apparatus comprising a membrane housing containing the rolled cylindrical membrane of FIG. 21, 22, or 25;

FIG. 27 is a planar detail view of the housing inlet and housing outlet of FIG. 26;

FIG. 28 is a top perspective view of planar membrane discs comprising hollow fibers;

FIG. 29 is a bottom perspective view of the planar discs of FIG. 28;

FIG. 30 is a perspective view of the planar discs of FIGS. 28 and 29 stacked to form an exemplary stacked cylinder membrane;

FIG. 31 is a perspective view of an exemplary membrane housing for containing the stacked cylinder membrane of FIG. 30;

FIG. 32 is a cut-away side view of an exemplary fluid separation apparatus comprising a membrane housing for containing the stacked cylinder membrane of FIG. 30;

FIG. 33 is a perspective view of an alternative embodiment of a fluid separation apparatus comprising a membrane housing containing an exemplary membrane;

FIG. 34a is a side view of the fluid separation apparatus of FIG. 33;

FIG. 34b is a partially cut-away side view of the fluid separation apparatus of FIG. 33.

Figure 1:
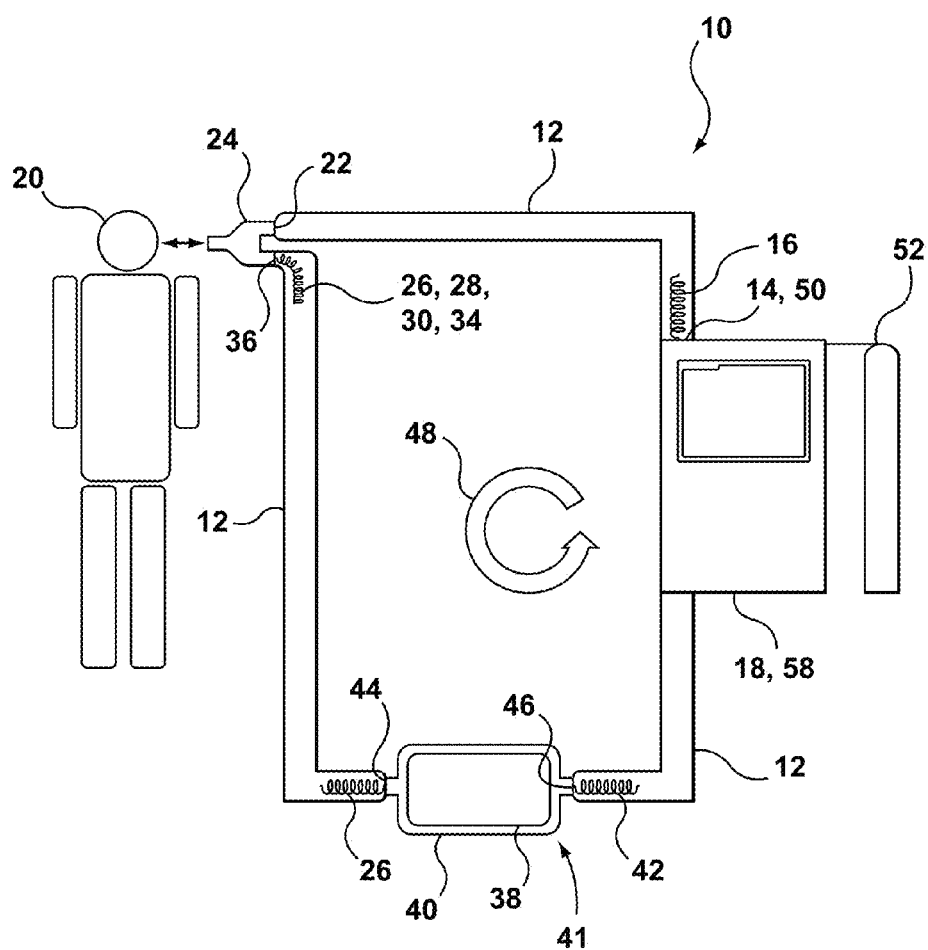
Figure 36:
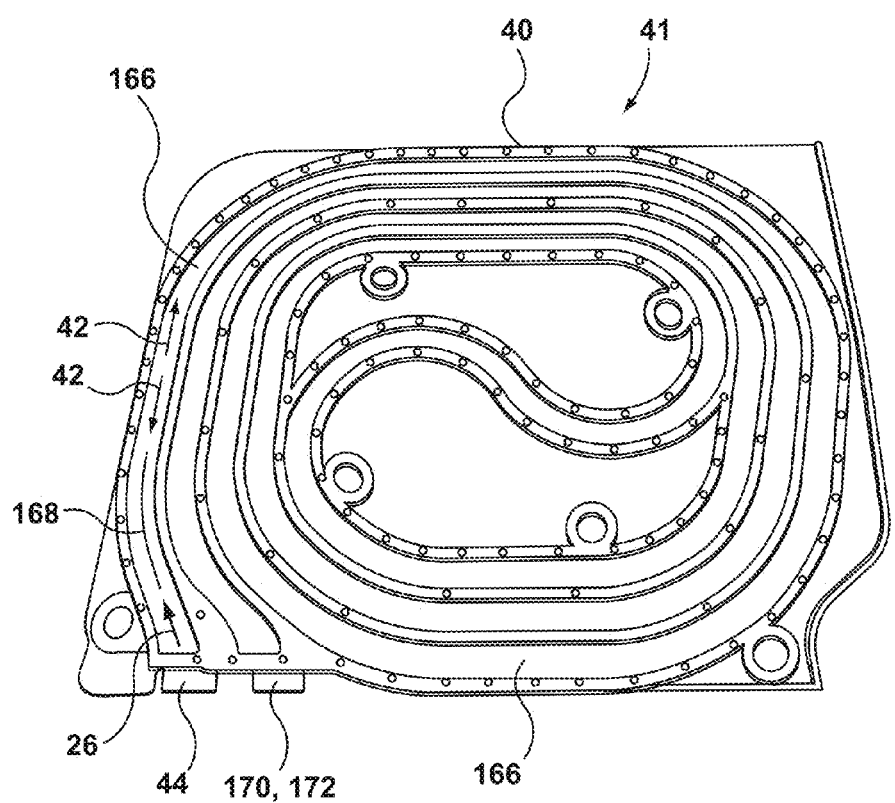
Figure 37:
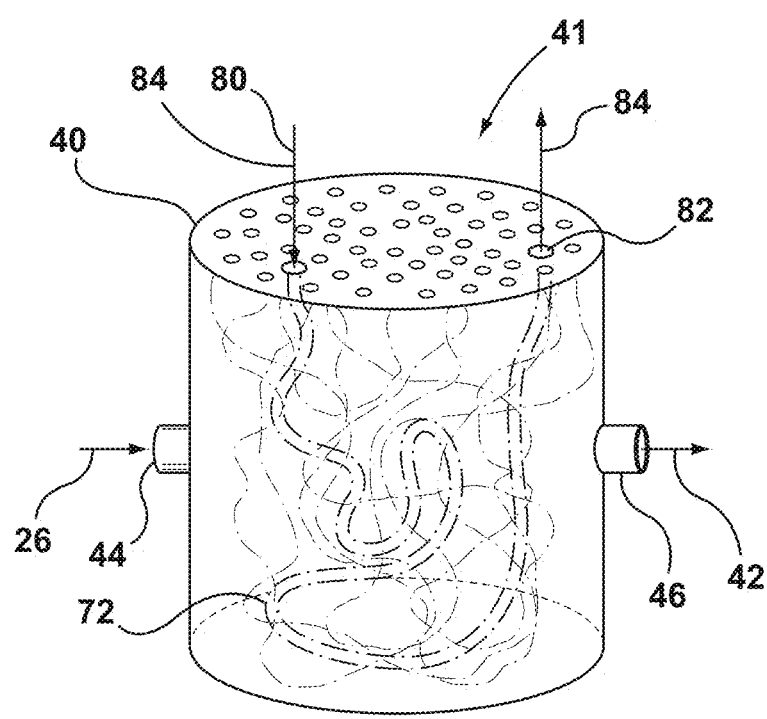
Figure 38:
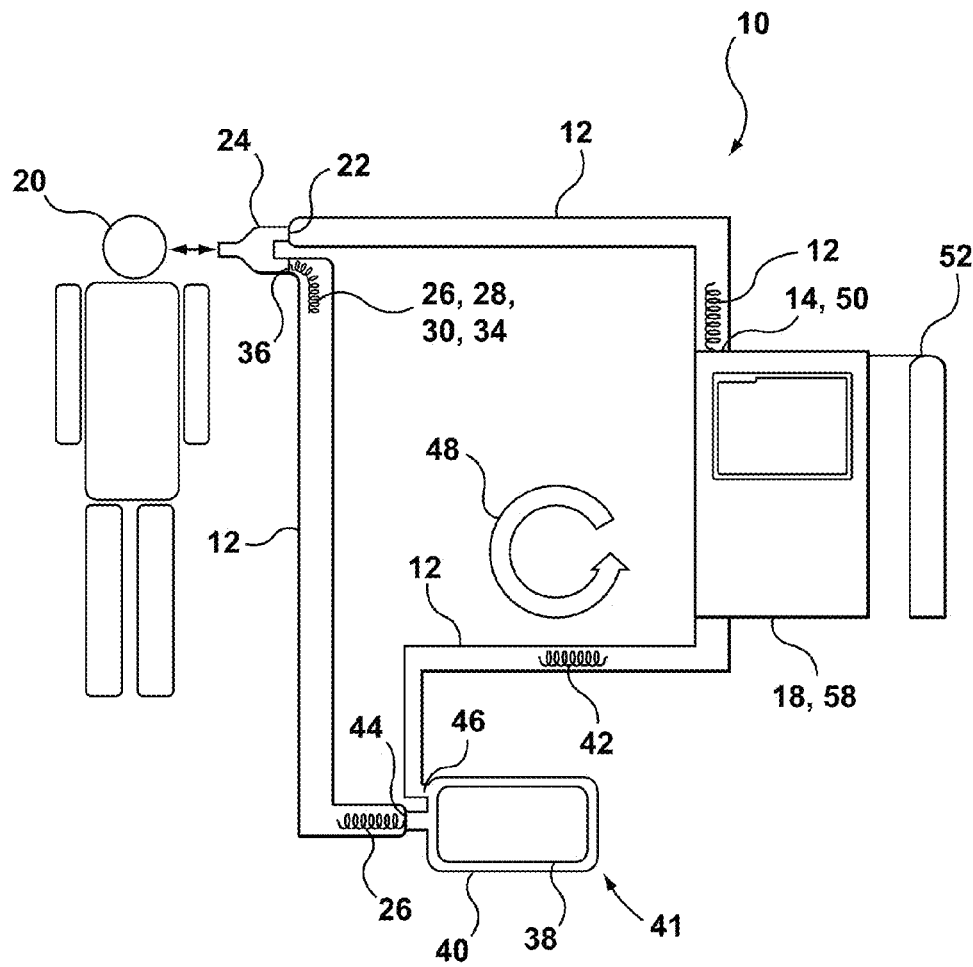
Figure 40:
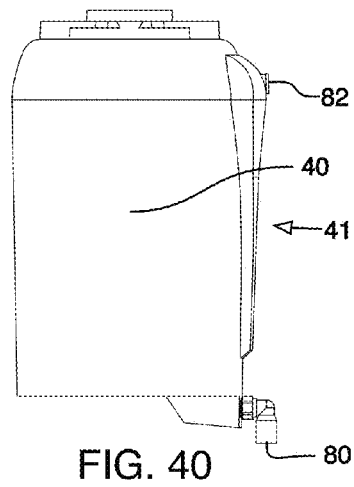
Figure 39:
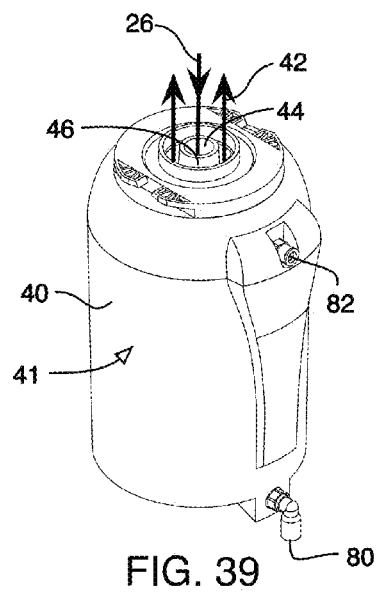
Figure 41:
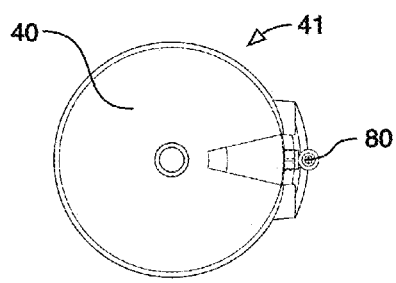
Figures 45, 47, 48:
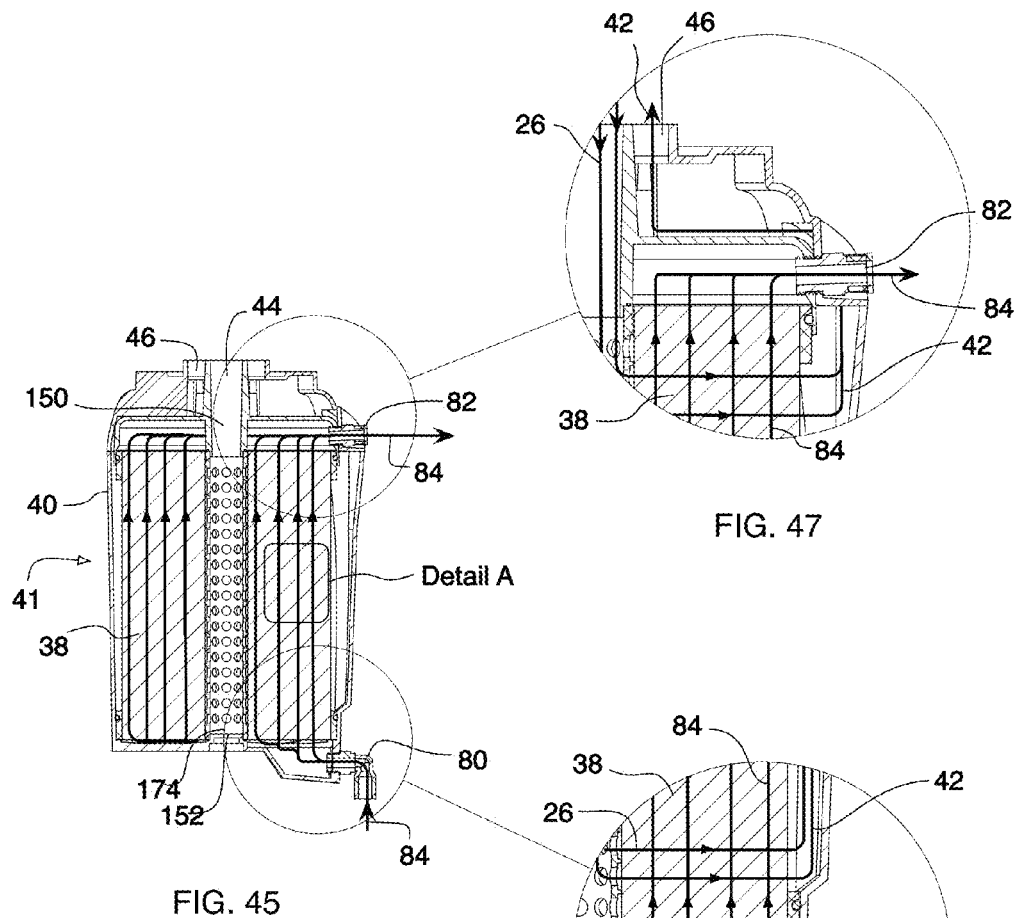
Figure 46:
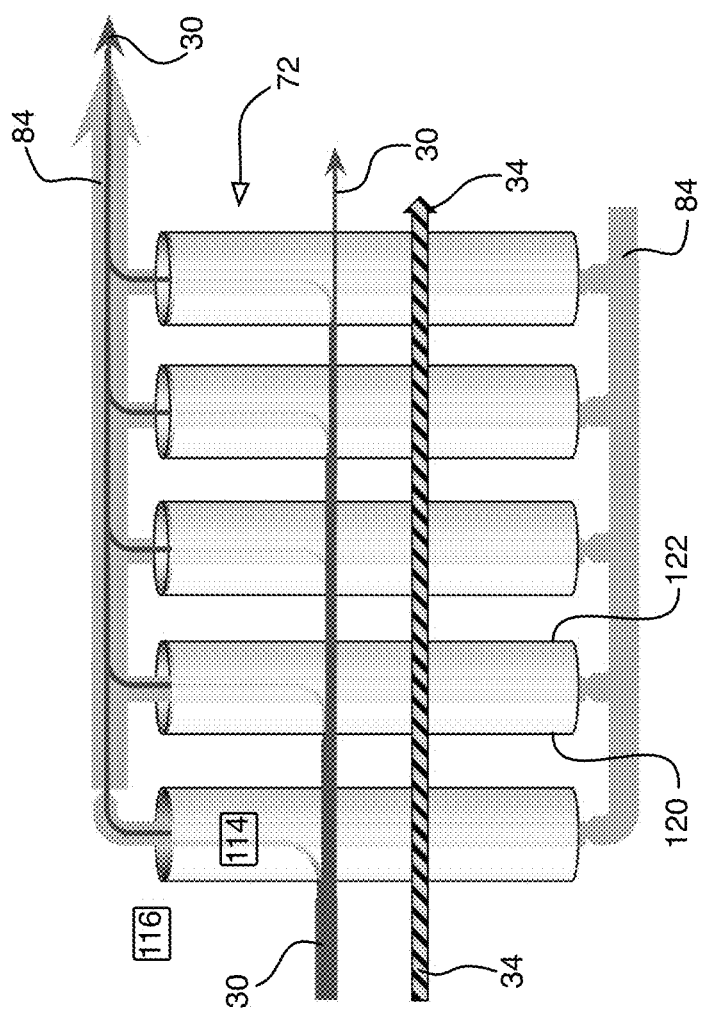
Figure 49:
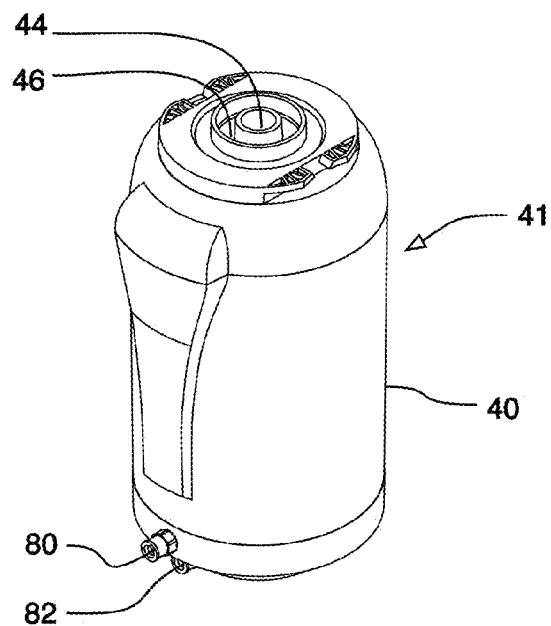
Figure 50:
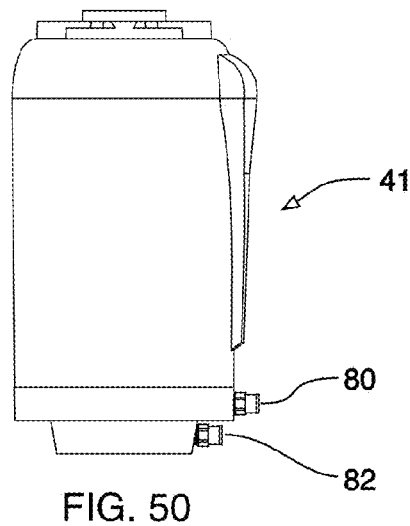
Figure 51:
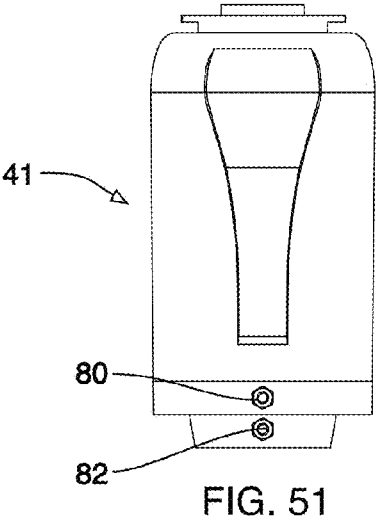
Figure 52:
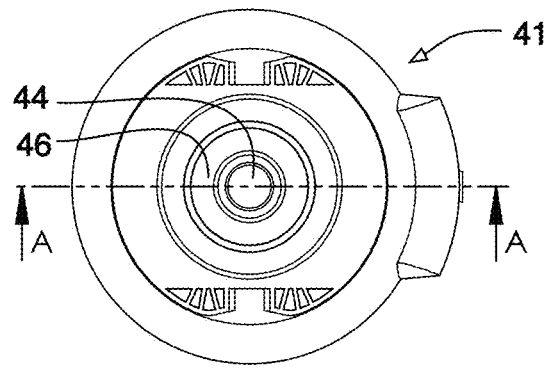
Figure 53:
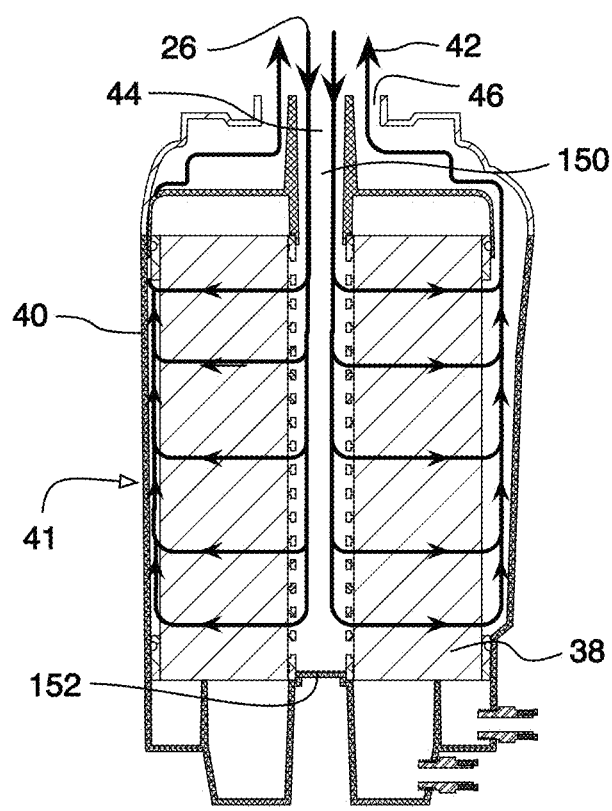
Figure 59:
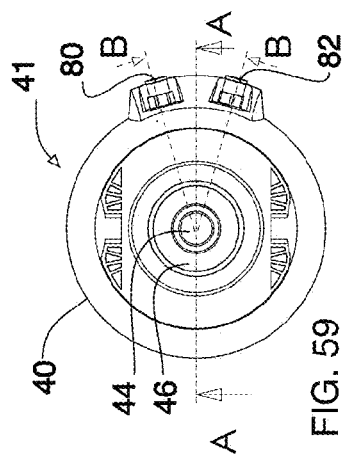
Figure 58:
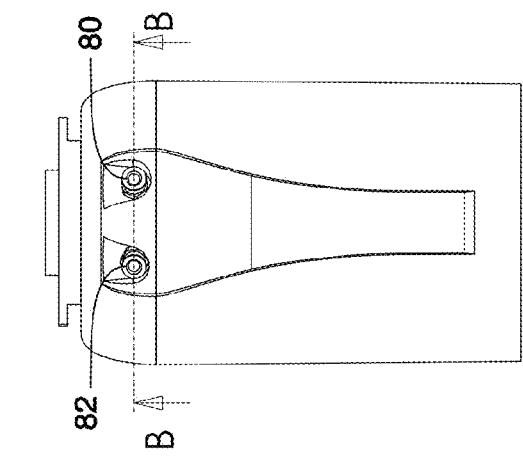
Figure 57:
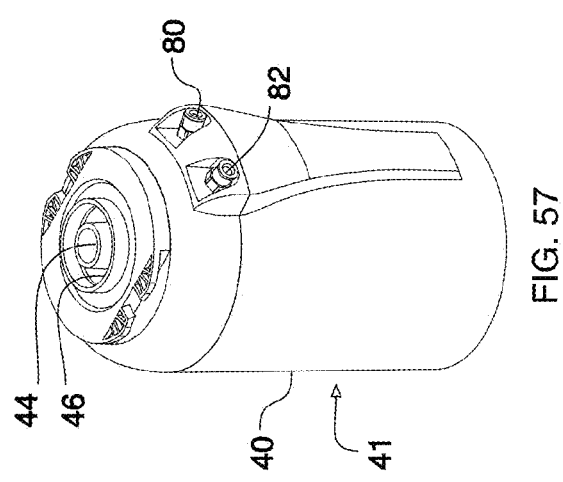
Figure 62:
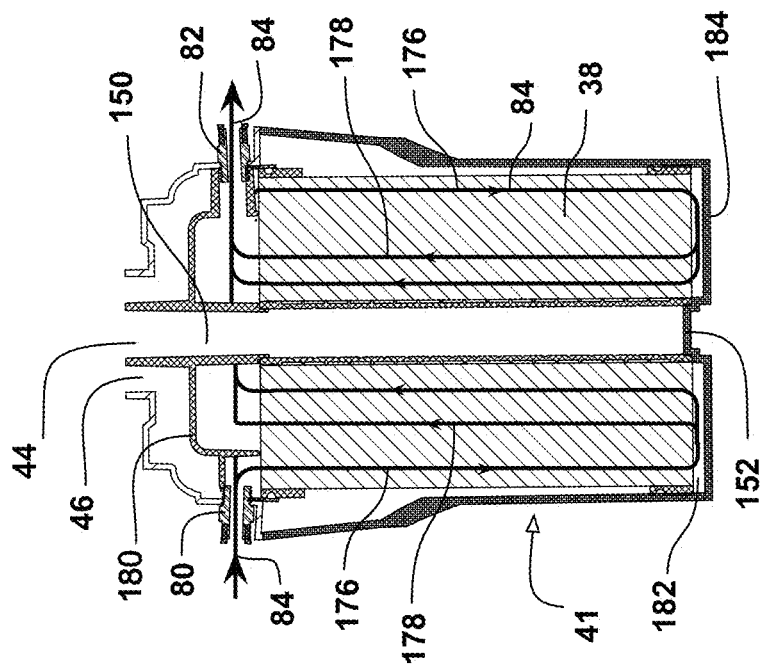
Figure 61:
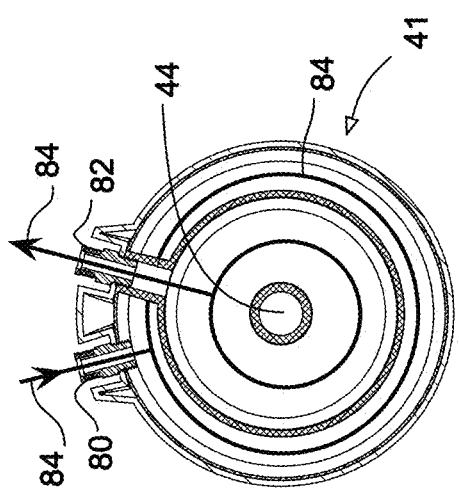
Figure 65:
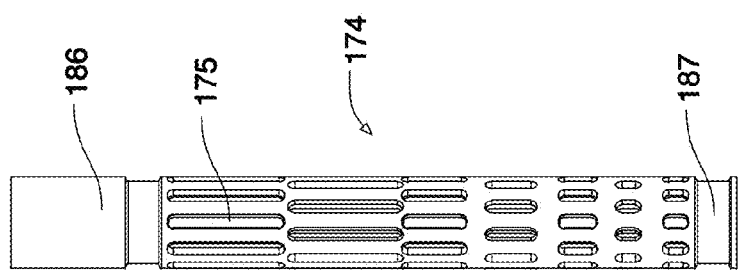

FIG. 35 is a front view of the fluid separation apparatus of FIG. 33;

FIG. 36 is a plan view of an alternative embodiment of a fluid separation apparatus comprising a membrane housing containing an exemplary membrane wherein the membrane housing is curved;

FIG. 37 is a perspective view of yet a further embodiment of a fluid separation apparatus comprising a membrane housing containing an exemplary membrane;

FIG. 38 is a side view of the anesthetic circuit of FIG. 1, modified to have the housing inlet and housing outlet on the same side of the membrane housing;

FIG. 39 is a perspective view of an exemplary fluid separation apparatus comprising a membrane housing containing an exemplary membrane;

FIG. 40 is a side view of the fluid separation apparatus of FIG. 39;

FIG. 41 is a bottom plan view of the fluid selection apparatus of FIGS. 39 and 40;

FIG. 42 is a top plan view of the fluid selection apparatus of FIGS. 39 to 41;

FIG. 43 is a cut-away side view of the fluid separation apparatus of FIGS. 39 to 42;

FIG. 44 is another cut-away side view of the fluid separation apparatus of FIGS. 39 to 42;

FIG. 45 is another cut-away side view of the fluid separation apparatus of FIGS. 39 to 42;

FIG. 46 is a detailed view of a portion of the membrane from the fluid separation apparatus of FIG. 45;

FIG. 47 is a detailed view of a portion of FIG. 45;

FIG. 48 is a detailed view of another portion of FIG. 45;

FIG. 49 is a perspective view of another exemplary fluid separation apparatus comprising a membrane housing containing an exemplary membrane;

FIG. 50 is a plan side view of the fluid separation apparatus of FIG. 49;

FIG. 51 is another plan side view of the fluid separation apparatus of FIG. 49;

FIG. 52 is a top view of the fluid separation apparatus of FIGS. 49 to 51;

FIG. 53 is a cut-away side view of the fluid separation apparatus of FIGS. 49 to 52;

FIG. 54 is another cut-away side view of the fluid separation apparatus of FIGS. 49 to 52;

FIG. 55 is a detailed view of a portion of FIG. 54;

FIG. 56 is a detailed view of another portion of FIG. 54;

FIG. 57 is a perspective view of another exemplary fluid separation apparatus comprising a membrane housing containing an exemplary membrane;

FIG. 58 is a front view of the fluid separation apparatus of FIG. 57;

FIG. 59 is a top view of the fluid separation apparatus of FIGS. 57 and 58;

FIG. 60 is a cut-away side view of the fluid separation apparatus of FIGS. 57 to 59;

FIG. 61 is a top cut-away view of the fluid separation apparatus of FIGS. 57 to 59;

FIG. 62 is another cut-away side view of the fluid separation apparatus of FIG. 57;

FIG. 63 is a detailed view of a portion of FIG. 60;

FIG. 64 is a detailed view of another portion of FIG. 60;

FIG. 65 is a side view of an exemplary inner shaft for a membrane housing; and

Figure 66:
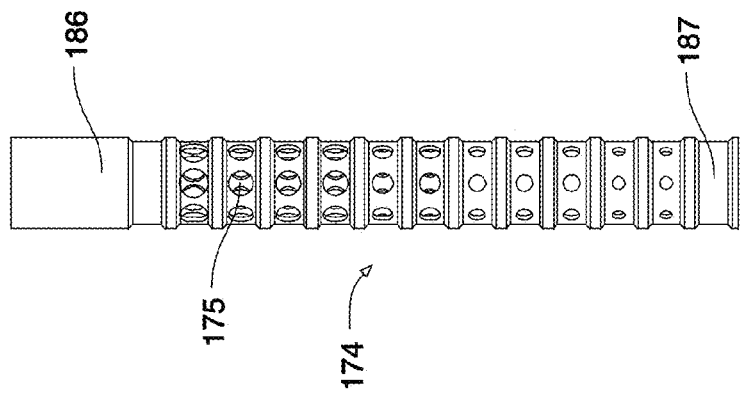

FIG. 66 is a side view of another exemplary inner shaft for a membrane housing.

DESCRIPTION OF VARIOUS EMBODIMENTS

FIG. 1 illustrates an exemplary anesthetic circuit 10 for treating a patient. As illustrated in FIG. 1, anesthetic circuit 10 comprises a flow passage 12. Flow passage 12 provides a passageway for transferring fluid to and from patient 20. It should be noted that fluid, as discussed herein, includes a gas or combination of gases, or a liquid or combination of liquids. Liquids may be present in vapor form, for example. The term fluid may also encompass a mixture of fluids and liquids (which, in some cases, may be in vapor form). In some cases, flow passage 12 provides a hollow conduit. Flow passage 12 may be flexible tubing, for example. Flow passage 12 may be made of a polymeric material, such as plastic. In some cases, anesthetic circuit 10 may be a ventilation system or, in some cases, operable in conjunction with a ventilation system.

An anesthetic inlet 14 is in fluid communication with flow passage 12. Anesthetic inlet 14 introduces at least an external anesthetic agent 16 into flow passage 12. FIG. 1 illustrates anesthetic inlet 14 of flow passage 12 in fluid communication with an anesthetic machine 18, as is conventionally used to deliver external anesthetic agent 16 to patient 20. External anesthetic agent 16 may be stored within and delivered to flow passage 12 by anesthetic machine 18. Anesthetic machine 18 may monitor the flow rates of the fluids travelling through flow passage 12. Anesthetic machine 18 may also be used to monitor the physical characteristics and vital signs of patient 20. Patient 20 is illustrated in FIG. 1 as being a human being; however, patient 20 may be any human, animal, cell or organism. Anesthetic circuit 10 may be used to treat any living cells or organisms, such as for example humans and animals. Anesthetic circuit 10 may be used to treat domestic pets, such as dogs and cats, for example.

Anesthetic circuit 10 comprises at least one fluid port 24. The at least one fluid port 24 is in fluid communication with flow passage 12 for providing at least external anesthetic agent 16 to patient 20. External anesthetic agent 16 will initially anesthetize patient 20, when the anesthetic process commences by delivery of external anesthetic agent 16 to the airway of patient 20, via the at least one fluid port 24. In some cases, the at least one fluid port 24 comprises exit outlet 22 and entry inlet 36. Exit outlet 22 may be configured to be directly received by the airway of patient 20, for delivery of fluid from flow passage 12 to patient 20. Alternatively, the at least one fluid port 24 comprises a Y-piece and exit outlet 22 may engage the Y-piece that is received by the airway of patient 20. Patient 20 breathes in the external anesthetic agent 16 through his/her airway, thereby delivering the anesthetic agent to the patient's lungs.

An exchange occurs in the alveoli of the lungs of patient 20 such that patient 20 breathes out transformed exhaled fluid mixture 26. Exhaled fluid mixture 26 comprises exhaled oxygen 28, exhaled carbon dioxide 30 and exhaled anesthetic agent 34.

Exhaled anesthetic agent 34 may be a molecular anesthetic agent, which may or may not be mixed with other fluids in addition to exhaled oxygen 28 and exhaled carbon dioxide 30. Those skilled in the art will appreciate that molecular anesthetic agents have more than one different atomic element bonded together to form a molecule. For example, sevoflurane is a molecular anesthetic agent that has the chemical form (1,1,1,3,3,3-hexafluoro-2-(fluoromethoxy)propane). In turn, sevoflurane comprises different elements fluorine, carbon and oxygen bonded together. By contrast, noble gases consist of only one atomic element that is not bonded to other atomic elements. For example, Xenon anesthetic is made up of only xenon atoms, and argon is made up of only argon atoms. Exhaled anesthetic agent 34 may originate from external anesthetic agent 16 and may comprise a molecular anesthetic agent. In some cases, exhaled anesthetic agent 34 is a molecular anesthetic agent that was solved in the patient's body (i.e. after cardiac surgery). In some cases, exhaled anesthetic agent 34 comprises a molecular anesthetic agent that was partially solved in the patient's body, and partially contained in external anesthetic agent 16 that was introduced to the patient's airway. In some embodiments, exhaled molecular anesthetic agent 34 is the only exhaled anesthetic agent. In some embodiments, exhaled anesthetic agent 34 comprises molecular anesthetic agent mixed with other non-molecular anesthetic agents.

Optionally, exhaled anesthetic agent 34 comprises a polyhalogenated ether. Exhaled anesthetic agent 34 may be hydrophobic (i.e. in gaseous form it dissolves in oil better than water, and in liquid form it is freely miscible with water). Non-limiting examples of exhaled anesthetic agent 34 include: sevoflurane, desflurane or isoflurane. Exhaled anesthetic agent 34 may be entirely comprised of one of sevoflurane, desflurane or isoflurane, or a mixture thereof.

Exhaled anesthetic agent 34 may be a volatile anesthetic. Volatile anesthetics are liquid at room temperature (optionally 20° C. at 1 atm), but readily evaporate under reduced pressure. Optionally, exhaled anesthetic agent 34 has a vapor pressure at 20° C. of between approximately 155 mmHg and 670 mmHg. Optionally, exhaled anesthetic agent 34 has a vapor pressure at 20° C. of between approximately 250 mmHg and 500 mmHg.

Optionally, exhaled anesthetic agent 34 has a boiling point at 760 mm in the range of approximately 20° C. to 60° C.

Optionally, exhaled anesthetic agent 34 is a molecular anesthetic agent that has a molecular weight of at least 150 g/mol. Optionally, exhaled anesthetic agent is a molecular anesthetic agent that has a molecular weight of at least 168 g/mol. Notably, by contrast, Xenon (which is an atomic anesthetic) has a lesser molecular weight of approximately 131.3 g/mol.

Anesthetic circuit 10 has at least one fluid port 24. The at least one fluid port 24 receives exhaled fluid mixture 26 from patient 20. The exhaled fluid mixture 26 comprises exhaled oxygen 28, exhaled carbon dioxide 30 and exhaled anesthetic agent 34. Flow passage 12 is in fluid communication with the at least one fluid port 24 for receiving exhaled fluid mixture 26 from the at least one fluid port 24.

The at least one fluid port 24 may comprise an entry inlet 36 for receiving exhaled fluid mixture 26 from patient 20. Flow passage 12 may be in fluid communication with entry inlet 36 for receiving exhaled fluid mixture 26 from entry inlet 36. Entry inlet 36 may be configured to be directly received by the airway of patient 20, for delivery of fluid from patient 20 to flow passage 12. Entry inlet 36 may be a one-way valve. The at least one fluid port 24 may comprise a Y-piece and entry inlet 36 may engage that Y-piece that is received by the airway of patient 20. Entry inlet 36 may be separate and distinct from exit outlet 22, as exemplified in FIG. 1. In these cases, exit outlet 22 is configured to receive modified fluid mixture 42 from membrane 38 and provide modified fluid mixture 42 to patient 20. In some embodiments, anesthetic inlet 14 is separate and distinct from entry inlet 36 and exit outlet 22. Exit outlet 22 may be a one-way valve. In some embodiments, at least one of entry inlet 36 and exit outlet 22 may function as anesthetic inlet 14. Anesthetic inlet 14 may be an injector for liquid anesthetic agents.

As exemplified in FIG. 1, anesthetic circuit 10 comprises a membrane 38 that may comprise at least one polymeric material and is in fluid communication with flow passage 12.

As exemplified in FIG. 1, membrane 38 may be contained within a membrane housing 40. Alternatively, membrane 38 may fit into an aperture in a wall of flow passage 12, in the absence of membrane housing 40. When membrane 38 fits into an aperture in a wall of flow passage 12, membrane 38 may be fixedly attached to the remainder of a wall of flow passage 12, or formed integrally therewith. In some cases, membrane 38 spans internally between the walls of flow passage 12.

As exemplified in FIG. 1, membrane 38 is configured to receive exhaled fluid mixture 26 from the at least one fluid port 24. In some cases, the at least one fluid port 24 comprises an entry inlet 36 that is separate from exit outlet 22. In some cases, membrane 38 is located downstream from entry inlet 36. In this embodiment, when the exhaled fluid mixture 26 travels through flow passage 12 and after it contacts the membrane 38, a portion of exhaled fluid mixture 26 passes through membrane 38 and out of flow passage 12, to leave a modified fluid mixture 42 in flow passage 12.

As exemplified in FIG. 1, when membrane 38 is contained in membrane housing 40, exhaled fluid mixture 26 may be received into membrane housing 40 through housing inlet 44. In some embodiments, anesthetic circuit 10 comprises a fluid separation apparatus 41, comprising membrane 38 and membrane housing 40. Fluid separation apparatus 41 may be releasably connectable to flow path 12. In some cases, fluid separation apparatus 41 is in the form of a cartridge that is releasably connectable to flow path 12. In some cases, fluid separation apparatus 41 may be removed from the anesthetic circuit and replaced with another fluid separation apparatus 41, if the fluid separation becomes damaged, for example. Housing inlet 44 may engage flow passage 12 by way for a fluidly sealed friction fit or a clamp coupling, for example. After exhaled fluid mixture 26 contacts the membrane 38 within membrane housing 40, a modified fluid mixture 42 is created within membrane housing 40. Modified fluid mixture 42 may exit the membrane housing 40 via housing outlet 46. Housing outlet 46 may engage flow passage 12 by way for a fluidly sealed friction fit or a clamp coupling, for example. Once the modified fluid mixture 42 exits the membrane housing 40, it may carry on through flow passage 12.

Membrane 38 may comprise at least one polymeric material. In some embodiments, membrane 38 is entirely made up of polymeric material. In some embodiments, membrane 38 is entirely made up of only one polymeric material. In some embodiments, membrane 38 comprises a polysiloxane and is thereby a polysiloxane membrane, More specifically, membrane 38 may comprise polydimethyl siloxane and thereby be a polydimethyl membrane. In some embodiments, membrane 38 comprises a halocarbon polymer and is thereby a polyhalocarbon membrane. More specifically, membrane 38 may comprise polymethylpentene and thereby be a polymethylpentene membrane.

The at least one fluid port 24 is configured to receive the modified fluid mixture from membrane 38 and provide at least modified fluid mixture 42 to patient 20. When an entry inlet 36 and separate exit outlet 22 are present, exit outlet 22 is configured to receive modified fluid mixture 42 from membrane 38. In some cases, exit outlet 22 is located downstream from membrane 38. Exit outlet 22 provides at least the modified fluid mixture 42 to patient 20. Entry inlet 36 may be located upstream from membrane 38.

As shown in FIG. 1, anesthetic circuit 10 comprises a fluid inlet 50 for introducing external fluid from external fluid source 52 to be added to modified fluid mixture 42 in flow passage 12. Fluid inlet 50 may be an independent inlet in fluid communication with flow passage 12. Alternatively, anesthetic inlet 14 may also serve as fluid inlet 50, as illustrated in FIG. 1. Fluid inlet 50 may allow additional fresh fluid (ex. oxygen or air) to be added to flow passage 12 and provided to patient 20 if needed, if the oxygen level within flow passage 12 falls below an acceptable level to support patient 20. Oxygen replenishment may be required if, for example, patient 20 increases his/her metabolic rate. Oxygen replenishment may also be required if significant amounts of oxygen exit the flow passage 12 via membrane 38. It should be noted that it is generally cheaper (per unit volume) to add air or oxygen to flow passage 12 than to add external anesthetic agent 16 to flow passage 12. External air source 52 may be a tank containing compressed, pressurized fluid (for example, air) therein.

In the manner outlined above, fluids may at least partially recirculate through flow passage 12. An example fluid flow direction 48 is illustrated in FIG. 1.

In an alternative embodiment to that illustrated in FIG. 1, membrane 38 may be located in a portion of flow passage 12 that is external to the portion of flow passage 12 that moves fluid in a circular loop corresponding to fluid flow direction 48. In some cases, membrane 38 may be located in a branch passage of flow passage 12 located between fluid source 52 and the portion of flow passage 12 that moves fluid in a circular loop corresponding to fluid flow direction 48. In some embodiments, membrane 38 may be located in anesthetic machine 18.

Figure 1A:
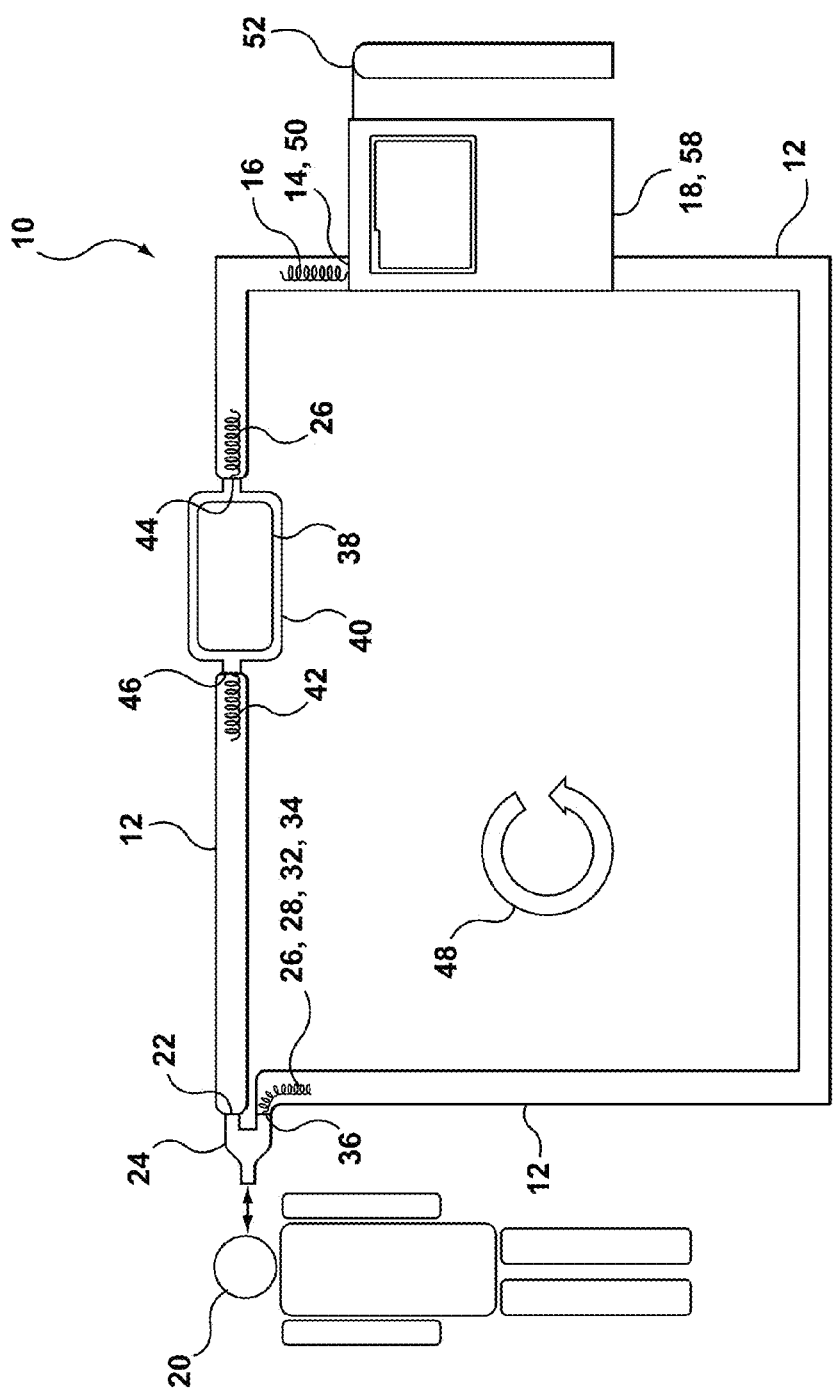

FIG. 1a illustrates membrane 38 at an alternative location to the location of membrane 38 in FIG. 1.

Figure 2:
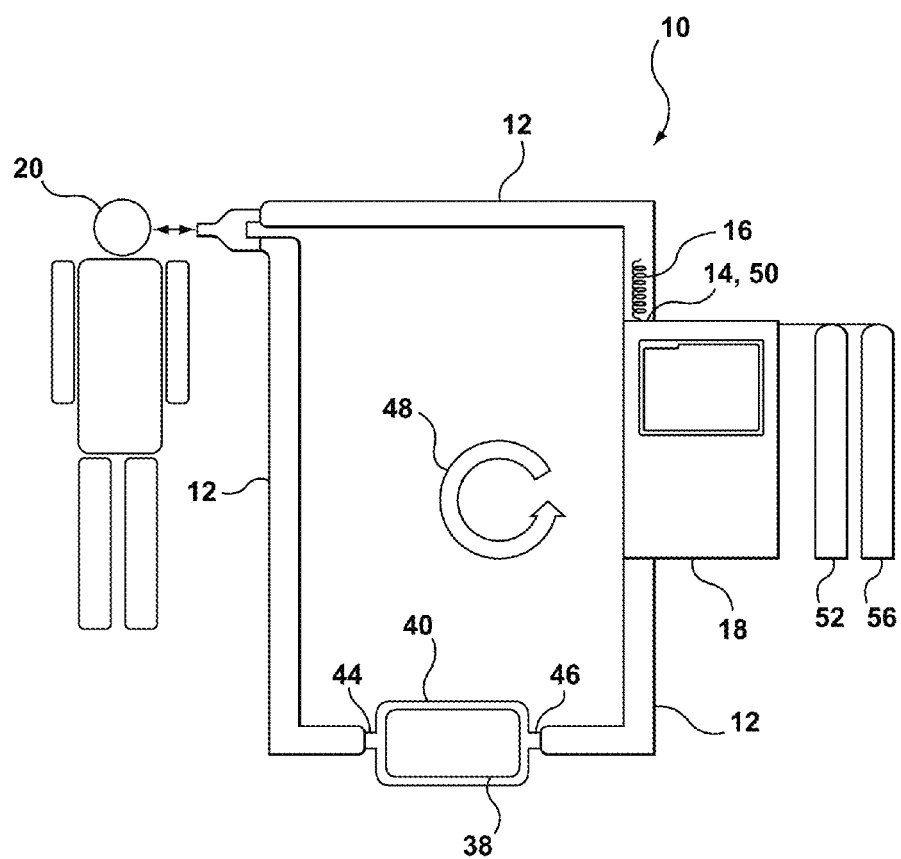

As shown in FIG. 2, in some cases, anesthetic circuit 10 comprises an external oxygen source 56 for enriching the external fluid with external oxygen. External oxygen source 56 may be a tank containing compressed, pressurized oxygen fluid therein. The external oxygen may be delivered through fluid inlet 50.

Returning to FIG. 1, anesthetic circuit 10 may comprise at least one flow generator 58 for facilitating flow of exhaled fluid mixture 26 and modified fluid mixture 42 through flow passage 12. In the embodiment shown in FIG. 1, anesthetic machine 18 may serve as flow generator 58, as is commonly known in the art. In some cases, a plurality of flow generators 58 may be provided. As an example, a first flow generator may drive the flow of the exhaled fluid mixture 26 and a second flow generator may drive the flow of modified fluid mixture 42. Examples of flow generator 58 include a motor, fan, pump or vacuum capable of advancing fluids through flow passage 12.

In an alternative embodiment illustrated in FIG. 3a, flow generator 58 comprises compressible member 59. As illustrated in FIG. 3a, compressible member 59 comprises opposing walls 60. When opposing walls 60 are moved towards one another, a positive driving pressure is created in flow passage 12. Opposing walls 60 may be flexible. Opposing walls 60 may be manually compressible by a human hand.

In some cases, as illustrated in FIG. 3a, flow passage 12 comprises at least one release valve 62 for releasing fluid within flow passage 12, if necessary.

In some cases, as exemplified in FIG. 3a, the at least one fluid port 24 includes only one fluid port. As exemplified, the one fluid port 24 is in fluid communication with flow passage 12 for providing at least external anesthetic agent 16 to patient 20. The one fluid port 24 receives the exhaled fluid mixture from patient 20, and flow passage 12 is in fluid communication with the one fluid port 24 to receive exhaled fluid mixture 26 from the one fluid port 24. The one fluid port 24 is configured to receive modified fluid mixture 42 from membrane 38 and provide modified fluid mixture 42 to patient 20.

Figure 3B:
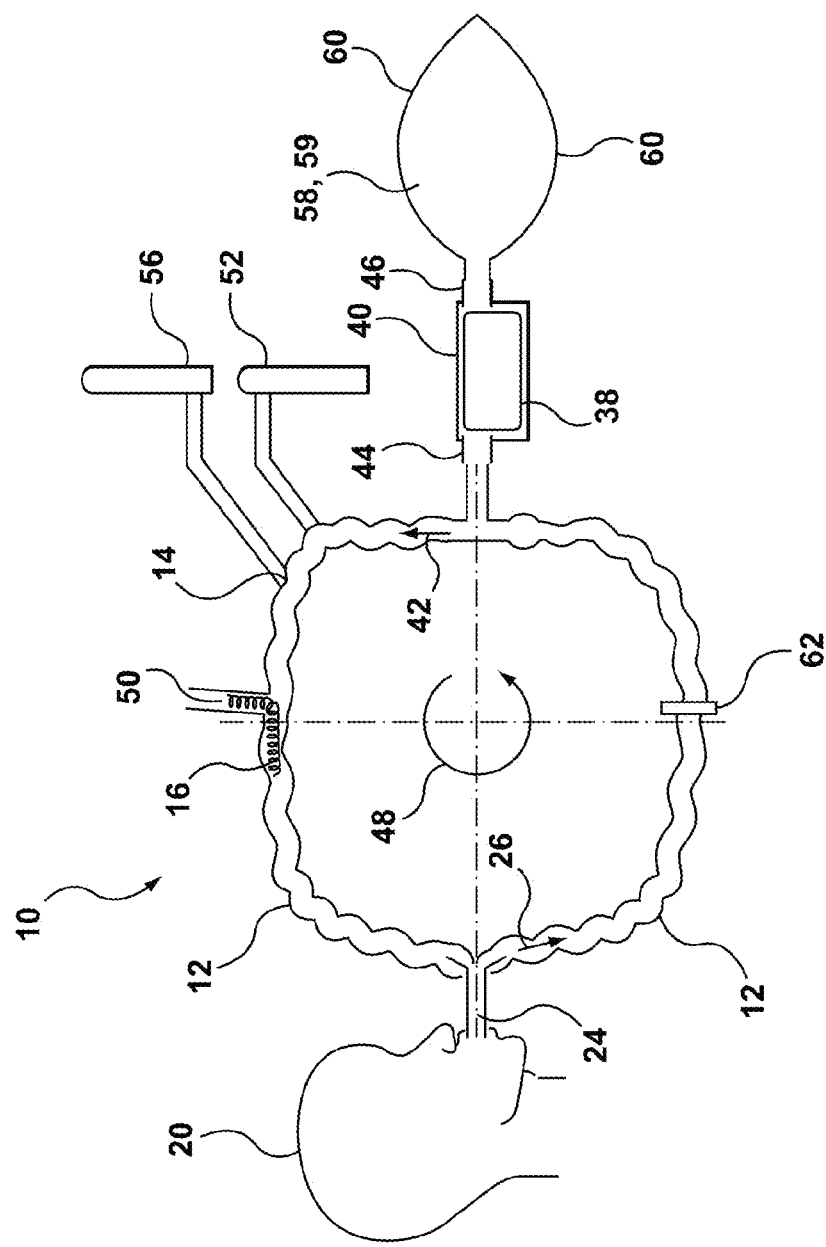

As exemplified in FIG. 3b, membrane housing 40 having a membrane therein 38 may also be located between the remainder of flow passage 12 and flow generator 58. As exemplified in FIG. 3b, flow generator 58 may comprise a compressible chamber 59 having opposing walls 60.

As exemplified in FIG. 3b, membrane 38 is located in membrane housing 40. Exhaled fluid mixture 26 enters membrane housing 40 via housing inlet 44. Membrane housing 40 may direct exhaled fluid mixture 26 into contact with membrane 38, to provide modified fluid mixture 42. Modified fluid mixture 42 may pass out of membrane housing 40 for a first time via membrane outlet 46. Flow generator 58 may direct modified fluid mixture 42 back into membrane housing 40 into contact with membrane 38 for a second time, then membrane housing 40 may direct modified fluid mixture 42 out of membrane housing 40 via housing inlet 44.

Figure 3C:
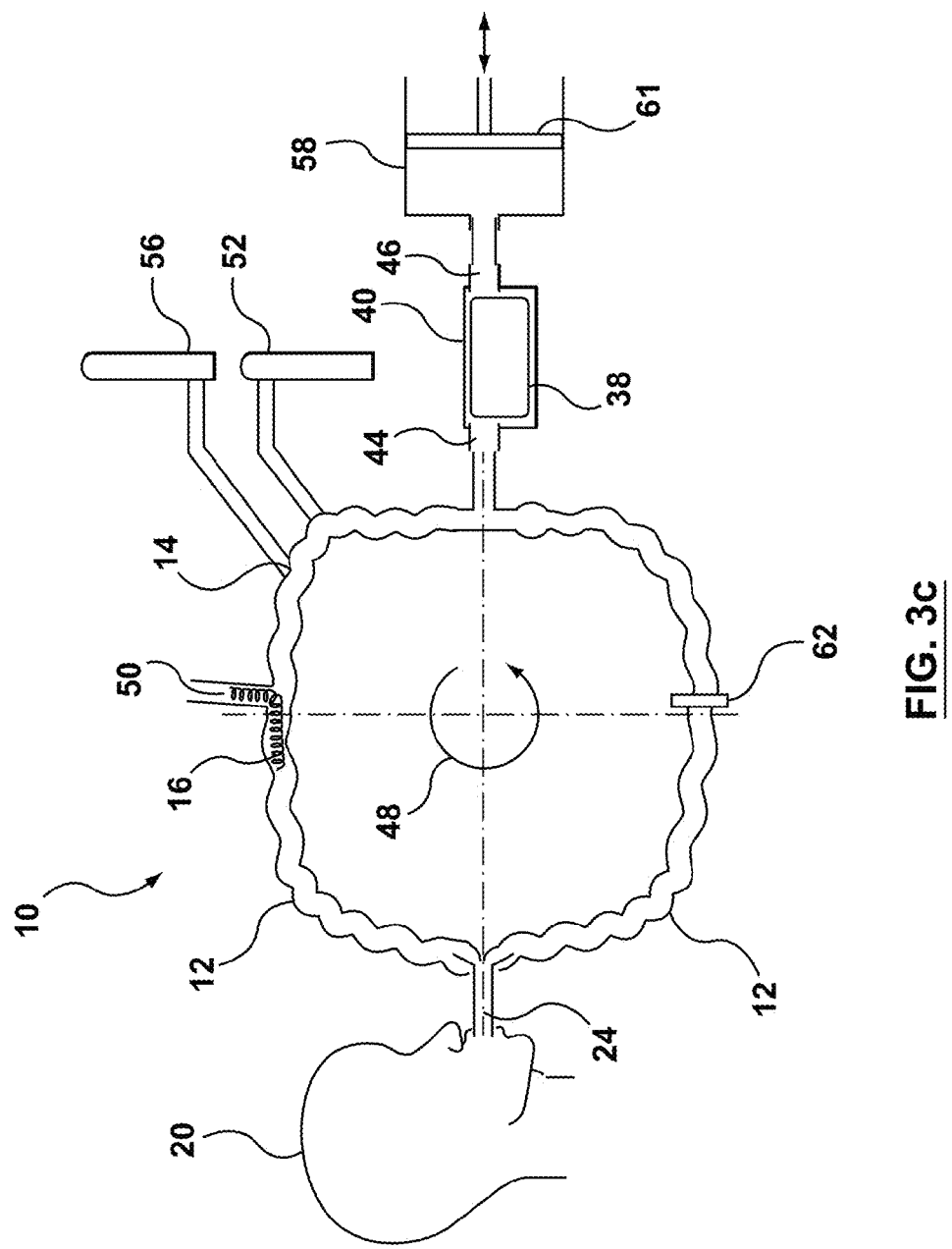

In an alternative embodiment shown in FIG. 3c, flow generator 58 comprises a bellow comprising a plunger 61 for generating fluid flow.

Figure 3D:
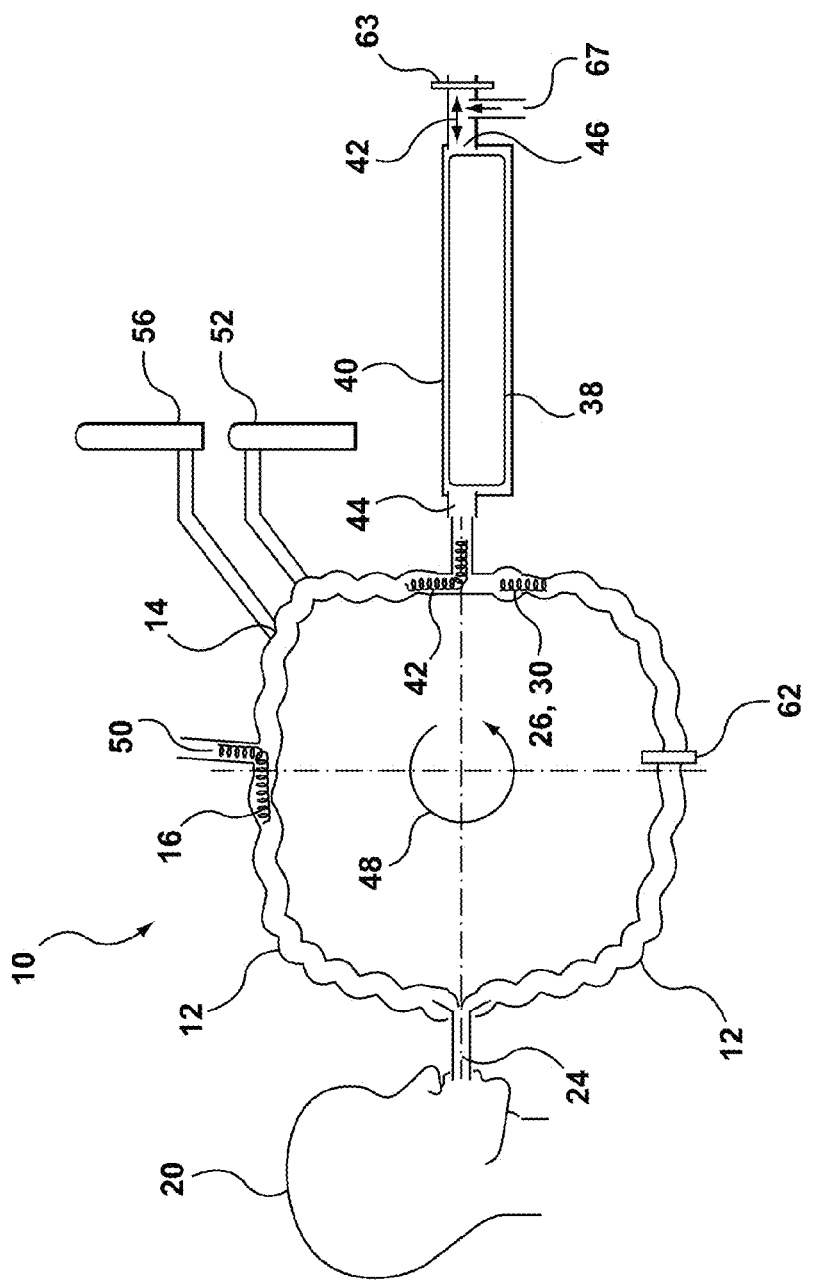

In the embodiment illustrated in FIG. 3d, anesthetic circuit 10 comprises a membrane housing 40. Membrane housing 40 has a membrane housing inlet 44. In operation, exhaled fluid mixture 26 enters housing 40 at inlet 44 and contacts membrane 38. During this fluid flow, control valve 63 is in an open position. Once the fluid passes membrane 38 when exhalation is completed, control valve 63 closes and fluid is delivered into injection port 67 to force the modified fluid mixture 42 to change direction and flow back towards membrane housing inlet 44 (which now allows modified fluid mixture 42 to exit membrane housing 40). When modified fluid mixture 42 moves towards membrane housing inlet 44, it passes by membrane 38 for a second time, thereby further reducing the exhaled carbon dioxide 30 concentration in modified fluid mixture 42. The forward and reverse fluid flow increases the contact time between the fluid mixture and membrane 38, thereby increasing the efficiency of the exhaled carbon dioxide extraction (per inhalation/exhalation cycle).

Figure 3E:
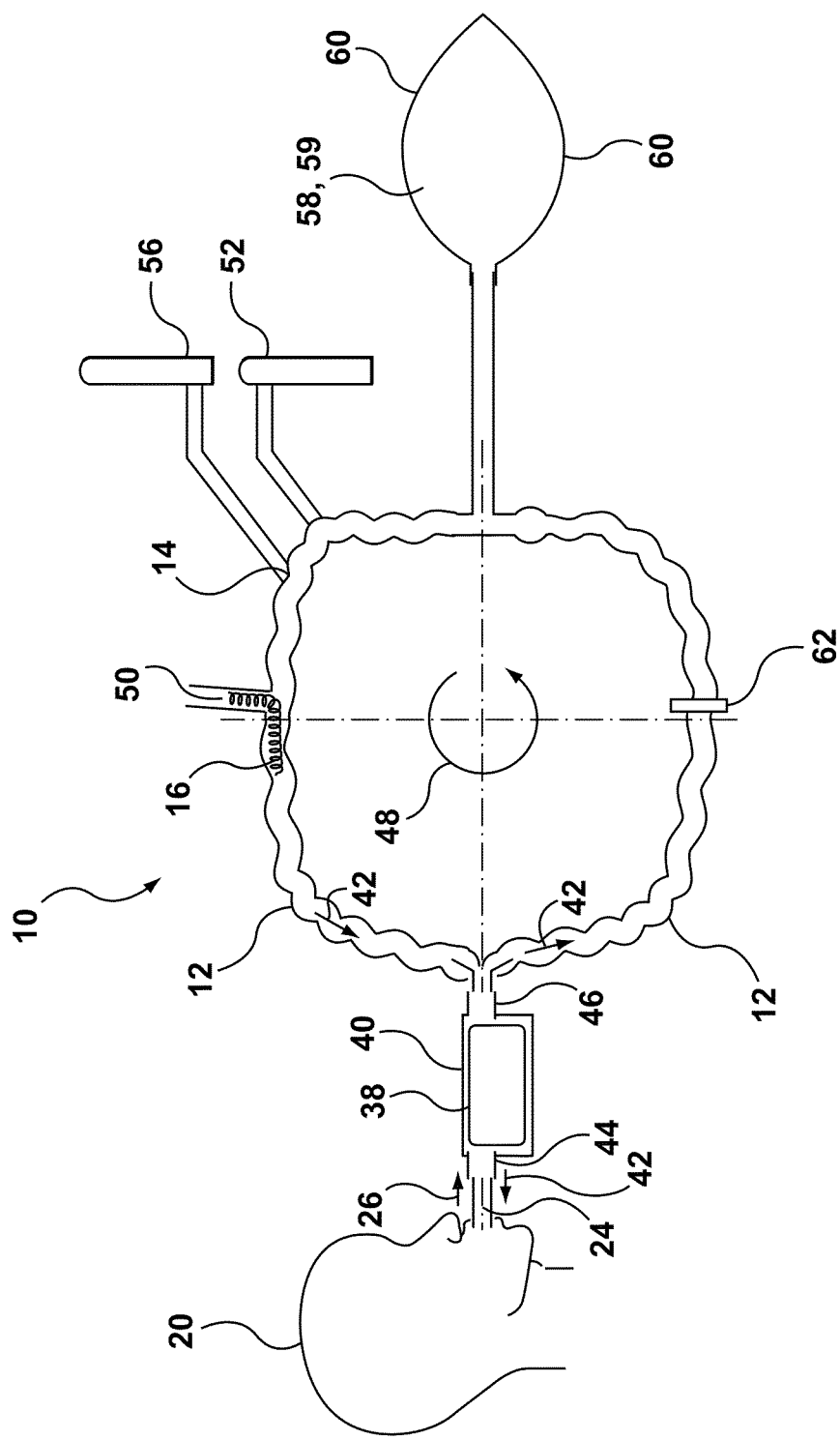

In the embodiment shown in FIG. 3e, membrane 38 and membrane housing 40 are located in the vicinity of patient 20's mouth. In this case, the at least one fluid port 24 includes only one fluid port 24. The fluid port provides at least external anesthetic agent 16 to patient 20. The fluid port also receives exhaled fluid mixture 26 from patient 20 and directs it toward membrane 38. Bellow 60 (or a similar pressure generation device) causes exhaled fluid mixture 26 to pass through membrane 38 twice (in opposite directions), then return to fluid port 24 as modified fluid mixture 42, at which point fluid port 24 receives modified fluid mixture 42 and provides at least modified fluid mixture 42 to patient 20.

Figure 3F:
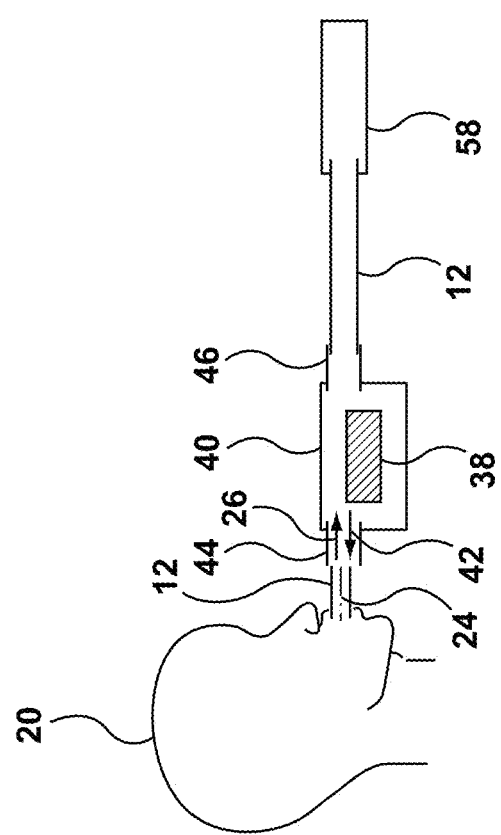

Similarly, in the embodiments shown in FIGS. 3f and 3g, the at least one fluid port 24 comprises only one fluid port 24 and facilitates double fluid flow through membrane 38.

Although flow passage 12 is illustrated as a discrete passage that is separate from membrane housing 40 in the figures (see FIGS. 3f and 3g, for example), it will be appreciated that, in some embodiments, flow passage 12 is not a discrete element and is not separate from membrane housing 40. For example, the inside of membrane housing 40 may define the entirety of flow passage 12 and membrane housing 40 (or a small port extending therefrom) may directly engage patient 20's mouth, in the absence of separate flow passage tubing.

In the embodiments shown in FIGS. 3b-3g, exhaled fluid mixture 26 passes through membrane 38 a first time to become modified fluid mixture 42. Modified fluid mixture 42 passes by membrane 38 for a second time, thereby further reducing the exhaled carbon dioxide 30 concentration in modified fluid mixture 42. The forward and reverse fluid flow increases the contact time between the fluid mixture and membrane 38, thereby increasing the efficiency of the exhaled carbon dioxide extraction (per inhalation/exhalation cycle).

Figure 4:
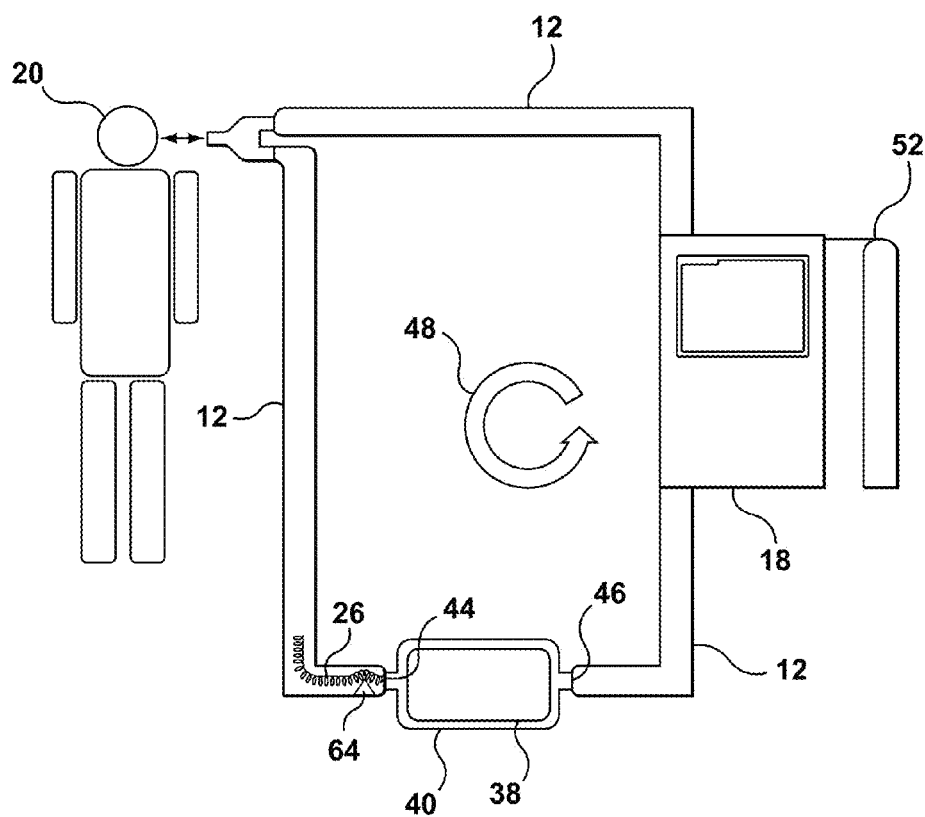
FIG. 4 is a side view of the anesthetic circuit of FIG. 1 further comprising a turbulence-inducing member.

As shown in FIG. 4, anesthetic circuit 10 may also comprise a turbulence-inducing component 64. The turbulence-inducing component 64 creates a turbulent flow of exhaled fluid mixture 26 at membrane 38 to increase contact between exhaled fluid mixture 26 and membrane 38. Turbulence-inducing component 64 may be any object placed within flow passage 12, as illustrated in FIG. 4, such that the fluids travelling therethrough are forced to flow around the object. Alternatively, turbulence-inducing component 64 may comprise a change in geometry within at least one wall of flow passage 12. Optionally, the change in geometry is abrupt, so as to generate fluid flow eddies within flow passage 12. The turbulence-inducing component 64 is optionally located upstream and adjacent to the membrane 38. When membrane 38 is contained in membrane housing 40, turbulence-inducing component 64 may be located upstream and adjacent to the housing inlet 44, as illustrated in FIG. 4. Turbulence-inducing component 64 may also be located within membrane housing 40.

As exemplified in FIGS. 3a-3e, flow passage 12 may have a non-uniform cross-section throughout its length so as to promote turbulent fluid flow through flow passage 12.

Figure 5:
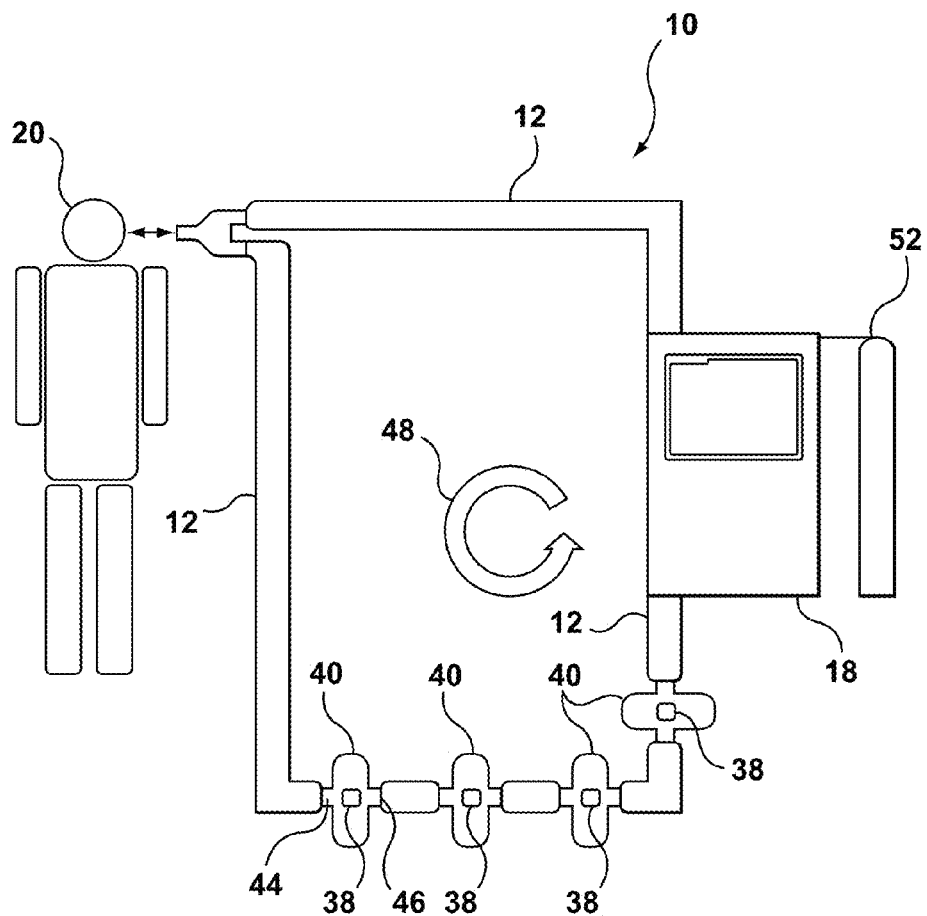
FIG. 5 is a side view of the anesthetic circuit of FIG. 1 further comprising a plurality of membrane housings and membranes.

As exemplified in FIG. 5, anesthetic circuit 10 may comprise a plurality of membranes 38. Each membrane 38 may be contained within its own membrane housing 40, as exemplified in FIG. 5.

Figure 6:
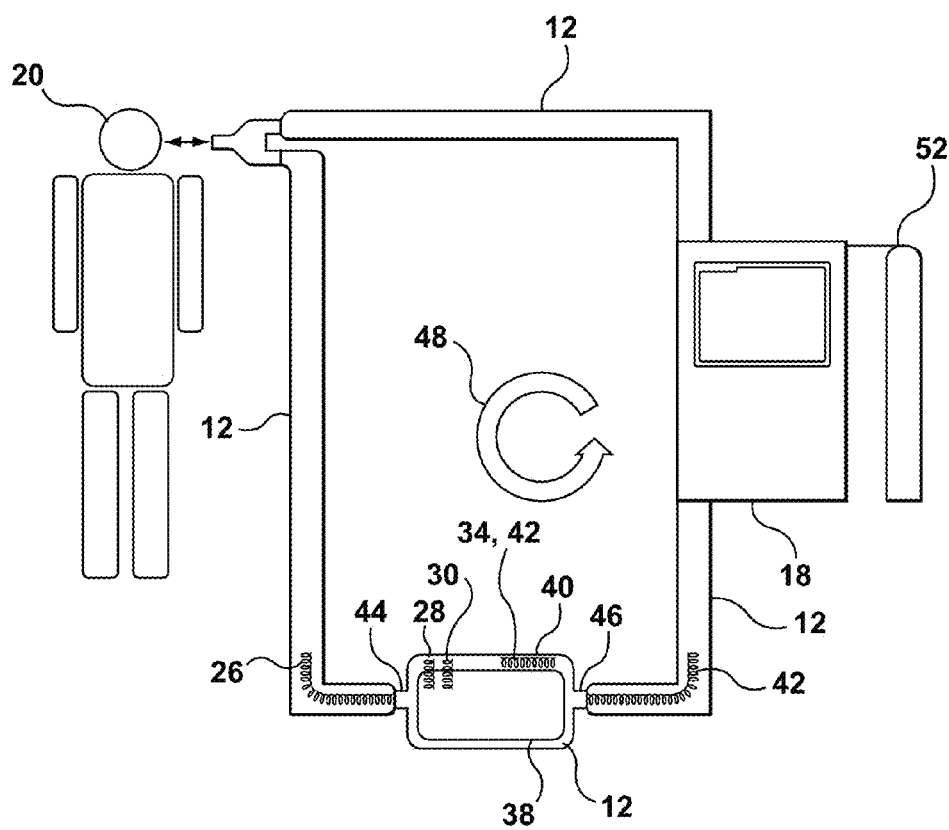
FIG. 6 is a side of view of the anesthetic circuit exemplifying fluid flows within the anesthetic circuit of FIG. 1.

As exemplified in FIG. 6, membrane 38 is at least partially impervious to the exhaled anesthetic agent 34 to at least partially retain exhaled anesthetic agent 34 in flow passage 12 after the exhaled fluid mixture 26 contacts the membrane 38. In some cases, membrane 38 is substantially impervious to the exhaled anesthetic agent 34 to substantially retain exhaled anesthetic agent 34 in flow passage 12 after the exhaled fluid mixture 26 contacts the membrane 38. Optionally, membrane 38 is substantially impervious to exhaled anesthetic agent 34. In some cases, membrane 38 is configured to permeate less than 5% of the anesthetic agent. In these cases, exhaled anesthetic agent 34 may be an exhaled molecular anesthetic agent. Optionally, membrane 38 is substantially impervious to atomic anesthetic agents (i.e. noble gases, including xenon, for example).

Most commonly, the separation factor of a membrane is defined as the ratio of the permeability of matter A and permeability of matter B. The permeability is equal to Flux divided by Partial Pressure Difference. The permeability of a membrane to a specific fluid is therefore a property of the membrane, and not directly linked to the operating conditions. A membrane's selectivity of fluid A to fluid B, for example, is therefore defined as Permeability A divided by Permeability B.

Membrane 38 may be pervious to exhaled oxygen 28 such that membrane 38 has an exhaled oxygen-to-exhaled anesthetic agent selectivity of greater than 1. In other words, more exhaled oxygen 28 may leave flow passage 12 through membrane 38 than exhaled anesthetic agent 34. Membrane 38 may be pervious to exhaled oxygen 28 such that membrane 38 has an exhaled oxygen-to-exhaled anesthetic agent selectivity of at least two 2. In other words, at least twice as much exhaled oxygen 28 may leave flow passage 12 through membrane 38 than exhaled anesthetic agent 34. Optionally, membrane 38 may be pervious to exhaled oxygen 28 such that is has an exhaled oxygen-to-exhaled anesthetic agent selectivity of at least 3, 4, 5, 10, 50, 100 or 250. In these cases, exhaled anesthetic agent 34 may be an exhaled molecular anesthetic agent. Optionally, membrane 38 is substantially pervious to exhaled oxygen.

Membrane 38 is pervious to exhaled carbon dioxide such that membrane 38 has an exhaled carbon dioxide-to-exhaled anesthetic agent selectivity of greater than 1. In other words, more exhaled carbon dioxide 30 leaves flow passage 12 through membrane 38 than exhaled anesthetic agent 34. The membrane is more pervious to exhaled carbon dioxide 30 than exhaled anesthetic agent 34 such that the membrane has an exhaled carbon dioxide-to-exhaled anesthetic agent selectivity of greater than 1. Membrane 38 may be substantially pervious to exhaled carbon dioxide such that membrane 38 has an exhaled carbon dioxide-to-exhaled anesthetic agent selectivity of at least 2. In other words, at least twice as much exhaled carbon dioxide 30 may leave flow passage 12 through membrane 38 than exhaled anesthetic agent 34. Optionally, membrane 38 may be pervious to exhaled carbon dioxide 30 such that is has an exhaled carbon dioxide-to-exhaled anesthetic agent selectivity of at least 3, 4, 5, 10, 50, 100 or 250. In these cases, exhaled anesthetic agent 34 may be an exhaled molecular anesthetic agent. Optionally, membrane 38 is substantially pervious to exhaled carbon dioxide.

Exhaled fluid mixture 26 contacts membrane 38 to leave modified fluid mixture 42 in flow passage 12. Membrane 38 separates a portion of the exhaled carbon dioxide 30 from the exhaled fluid mixture 26. The modified fluid mixture 42 has a lower amount of exhaled carbon dioxide 30 than does exhaled fluid mixture 26. In other words, the amount of exhaled carbon dioxide 30 in modified fluid mixture 42 is less than the amount of exhaled carbon dioxide 30 in exhaled fluid mixture 26. In some cases, modified fluid mixture 42 has a lower amount of exhaled oxygen 28 than exhaled fluid mixture 26. FIG. 6 shows exhaled oxygen 28 and exhaled carbon dioxide 30 passing through membrane 38 and out of flow passage 12 after exhaled fluid mixture 26 contacts membrane 38.

Many conventional membranes used in anesthetic circuits focus on retaining exhaled oxygen 28 in flow passage 12. It is advantageous, in certain cases, to let some of exhaled oxygen 28 to pass through membrane 38. FIG. 6 shows exhaled oxygen 28 passing out of flow passage 12 through membrane 38. In some embodiments, a substantial amount of exhaled oxygen 28 is permitted to leave the system. External oxygen can be relatively inexpensively replenished into flow passage 12 to account for the exhaled oxygen 28 lost through membrane 38. The cost of external oxygen is substantially less than the cost of external anesthetic agent 16. It is advantageous to at least partially (optionally, substantially) retain exhaled anesthetic agent 34, which may be an exhaled molecular anesthetic agent, while allowing some (optionally, a substantial amount of) exhaled oxygen 28 to pass through membrane 38 and out of anesthetic circuit 10. Membranes that have these properties provide some advantages over conventional membranes that have a relatively high (carbon dioxide)/(oxygen) selectivity. In some cases, membranes that allow more exhaled oxygen 28 than anesthetic agent 34 (which may be a molecular anesthetic agent) to pass therethrough are advantageous for use in anesthetic circuit 10. Some membranes having this property are free of substances that are chemically reactive with exhaled carbon dioxide 30 (and possibly exhaled molecular anesthetic agent 34) that produce harmful by-products. Furthermore, the need to replace membranes when a chemically reactive material is used up can be avoided by the use of some membranes that allow exhaled oxygen 28 (optionally in substantial amounts) to pass therethrough.

It is advantageous to retain at least some (optionally a substantial amount) of relatively expensive exhaled anesthetic agent 34 (which may be an exhaled molecular anesthetic agent) for re-inhalation by patient 20, while reducing (optionally substantially) the amount of exhaled carbon dioxide 30 in anesthetic circuit 10. Since exhaled carbon dioxide 30 is permitted to pass through membrane 38 and out of flow passage 12, this prevents the patient from re-inhaling excessive amounts of exhaled carbon dioxide 30, which could have detrimental health effects.

Exhaled anesthetic agent 34 may be a volatile anesthetic agent. In this case, membrane 38 is at least partially (optionally, substantially) impervious to the volatile anesthetic agent. Exhaled anesthetic agent 34 may include a mixture of sevoflurane, isoflurane and/or desflurane. Membrane 38 may be at least partially (optionally, substantially) impervious to sevoflurane, isoflurane and/or desflurane.

Figure 7:
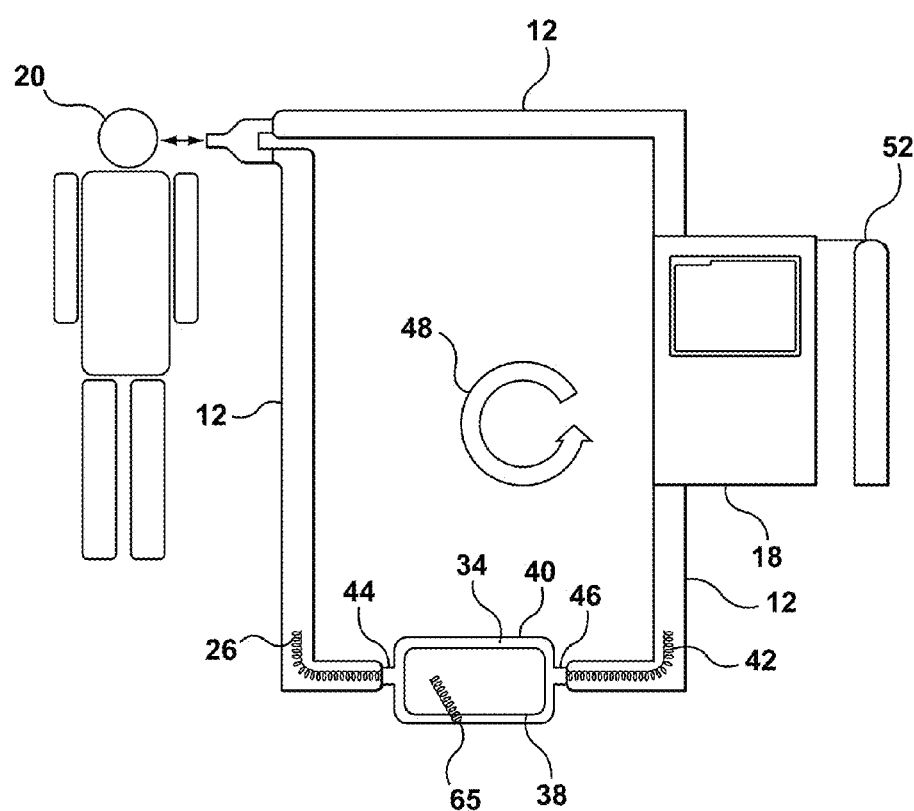
FIG. 7 is a side of view of the anesthetic circuit of FIG. 1 illustrating fluid flows including a secondary oxygen.

In some cases, as exemplified in FIG. 7, membrane 38 is configured such that secondary oxygen 65 located external to flow passage 12 passes through membrane 38 and into flow passage 12. Secondary oxygen 65 may be a natural component that is part of atmospheric air adjacent membrane 38, on a side of the membrane that is external to flow passage 12. Secondary oxygen 65 may also be introduced from an external source, such as a compressed tank of air or substantially pure oxygen, for example.

In the context of the present application, the negligible amount of any anesthetic substances typically present in air are not considered to be anesthetic agents. External anesthetic agent 16 (see FIG. 1) and exhaled anesthetic agent 34, for the purposes of the present application, pertain to substances that are present in sufficient quantities to have (or at least appreciably contribute to) the anesthetic or desired protective effect on patient 20. Therefore, reference to an anesthetic agent refers to chemicals that are added to the naturally occurring constituents of air. In some embodiments, external anesthetic agent 16 comprises a mixture of different anesthetic agents and exhaled anesthetic agent 34 comprises a mixture of different anesthetic agents.

By retaining some (or, optionally, a substantial amount) of exhaled anesthetic agent 34 (which may be an exhaled molecular anesthetic agent) within flow passage 12, exhaled anesthetic agent 34 can be re-circulated and re-inhaled by patient 20. Therefore, less costly external anesthetic agent 16 (see FIG. 1) needs to be added to the flow passage 12 to keep the patient under the influence of the anesthetic. The amount of environmentally harmful exhaled anesthetic agent 16 that is exhausted into the external atmosphere may be minimized.

In some cases, membrane 38 is inert with respect to exhaled anesthetic agent 34.

In some cases, membrane 38 is completely inert. In other words, membrane 38 is not chemically reactive with any other substances.

Membrane 38 may be free of any amino acids. In this case, no amino acids are impregnated into membrane 38 or deposited onto a surface of membrane 38.

When a membrane is impregnated with an amino acid or has amino acids deposited thereon, the amino acids react with the exhaled carbon dioxide 30. During this reaction, the amino acids may be consumed. Once the amino acids are consumed, the membrane 38 has to be replaced (or more amino acids added thereto). It is advantageous to have a membrane 38 that is inert and does not have to be replaced or replenished due to chemical degradation.

In some embodiments, exhaled fluid mixture 26 comprises a metabolic product including acetaldehyde, acetone, ethane, ethylene, hydrogen, isoprene, methane, methylamine or pentane. Membrane 38 may be pervious to the metabolic product to permeate the metabolic product through membrane 38, and out of flow passage 12. Optionally, membrane 38 has a metabolic product-to-exhaled anesthetic agent 34 (which may be a molecular anesthetic agent) selectivity of greater than 1. In this case, exhaled fluid mixture 26 contacts membrane 38 to leave modified fluid mixture 42 in the flow passage having a lower amount of the metabolic product than exhaled fluid mixture 26. Membrane 38 may have a metabolic product-to-exhaled anesthetic agent (which may be an exhaled molecular anesthetic agent) selectivity of at least 2. Optionally, membrane 38 has a metabolic product-to-exhaled anesthetic agent (which may be an exhaled molecular anesthetic agent) selectivity of at least 3, 4, 5, 10, 50, 100 or 250.

Example membranes for membrane 38 (shown generally in FIGS. 1-7) will now be discussed in detail.

In some embodiments of this disclosure, a membrane comprises at least one hollow fiber. In some embodiments, a membrane comprises a plurality of hollow fibers. The membrane may consist entirely of a plurality of hollow fibers. The hollow fibers may comprise polymeric material. The hollow fibers may consist entirely of polymeric material.

In an embodiment of this disclosure, a membrane comprises a plurality of hollow fibers spaced from one another and adaptable to be substantially parallel to an entry direction of an exhaled fluid mixture when the exhaled fluid mixture initially contacts the plurality of hollow fibers.

Figure 8:
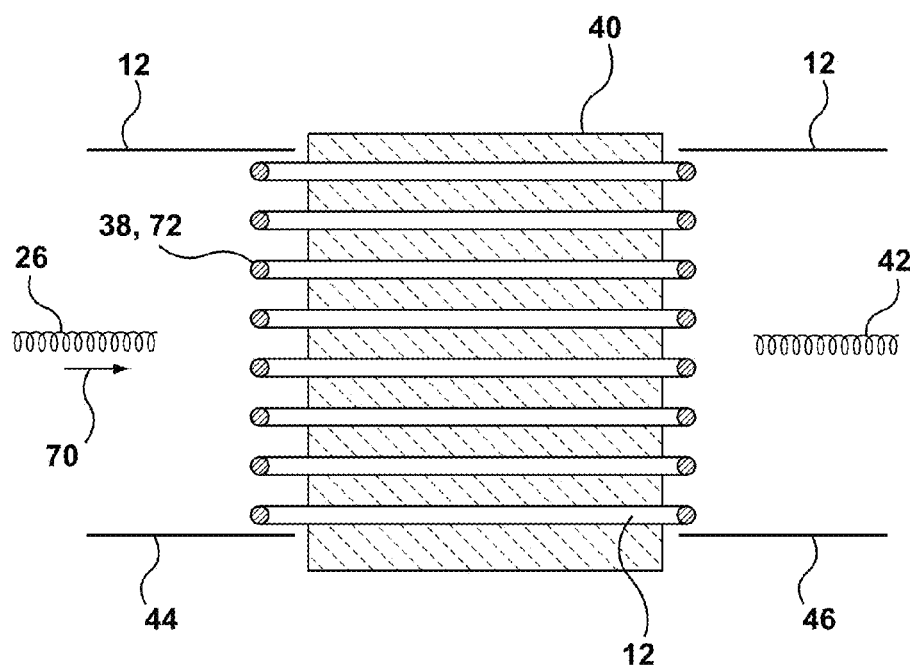
FIG. 8 is a side view of an exemplary membrane.

Membrane 38, as shown in FIG. 8, may be used in an anesthetic circuit, such as anesthetic circuit 10 shown in FIG. 1, for example. As exemplified in FIG. 8, exhaled fluid mixture 26 has entry direction 70. Although the flow direction of different portions of the exhaled fluid mixture 26 may be varied and the flow may be turbulent at this point, the exhaled fluid mixture 26 has an average direction indicated by entry direction 70 as it approaches and contacts hollow fibers 72, as defined by flow passage 12. As illustrated, membrane 38 comprises a plurality of hollow fibers 72. In some cases, the longitudinal axes of hollow fibers 72 are substantially parallel to entry direction 70 of exhaled fluid mixture 26, as shown in FIG. 8.

FIG. 8 exemplifies hollow fibers 72 that are spaced from one another and substantially parallel to the entry direction 70 of exhaled fluid mixture 26. As shown in FIG. 8, membrane 38 may be at least partially contained within membrane housing 40. In this case, exhaled fluid mixture 26 enters into hollow fibers 72 via one end of the hollow fibers. The portion of the exhaled fluid mixture that remains interior to the hollow fibers 72 exits the membrane 38 as modified fluid mixture 42. The components (or portion thereof) that selectively pass from the interior to the exterior of hollow fibers 72 pass through membrane 38 and out of flow passage 12. At least exhaled carbon dioxide 30 selectively exits hollow fibers 72. In some cases, exhaled oxygen 28 also selectively exits hollow fibers 72.

In an embodiment of this disclosure, a membrane comprises a plurality of hollow fibers spaced from one another and adaptable to be substantially perpendicular to an entry direction of exhaled fluid mixture when the exhaled fluid mixture initially contacts the plurality of hollow fibers.

Figure 9:
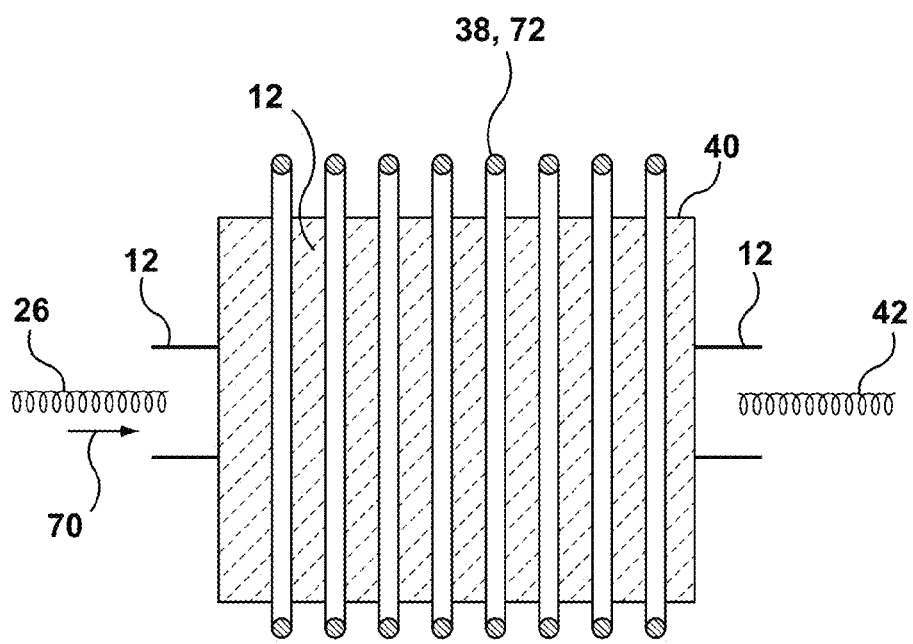
FIG. 9 is a side view of an alternative membrane.

Membrane 38, as shown in FIG. 9, may be used in an anesthetic circuit, such as anesthetic circuit 10 shown in FIG. 1, for example. FIG. 9 exemplifies membrane 38 comprising hollow fibers 72 spaced from one another and substantially perpendicular to the entry direction 70 of exhaled fluid mixture 26. As shown in FIG. 9, membrane 38 may be at least partially contained within membrane housing 40. As the exhaled fluid mixture 26 contacts the outer surface of a hollow fibers 72, at least exhaled carbon dioxide 30 selectively enters into hollow fibers 72. In some cases, exhaled oxygen 28 also selectively enters into hollow fibers 72. The components (or portion thereof) that enter into hollow fibers 72 then pass through membrane 38 out of the flow passage 12 via at least one end of the hollow fibers 72. The portion of the exhaled fluid mixture 26 that remains exterior to the hollow fibers 72 (i.e. remains in flow passage 12) exits housing 40 as modified fluid mixture 42. Typically, modified fluid mixture 42 has a lesser amount of any components (or portions thereof) lost through the ends of hollow fibers 72.

In an alternative embodiment, at least some of hollow fibers 72 are oriented at an angle other than perpendicular or parallel to entry direction 70 of the exhaled fluid mixture.

Figure 10:
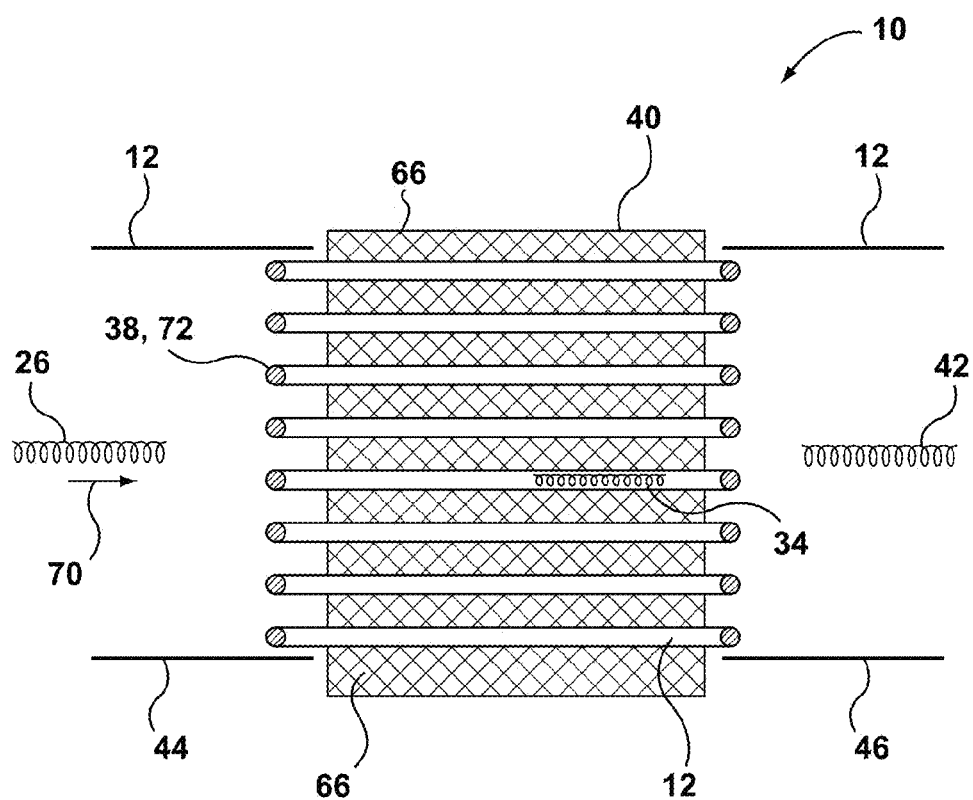
FIG. 10 is a side view of the membrane of FIG. 8 further comprising a carbon dioxide absorbing material.
Figure 11:
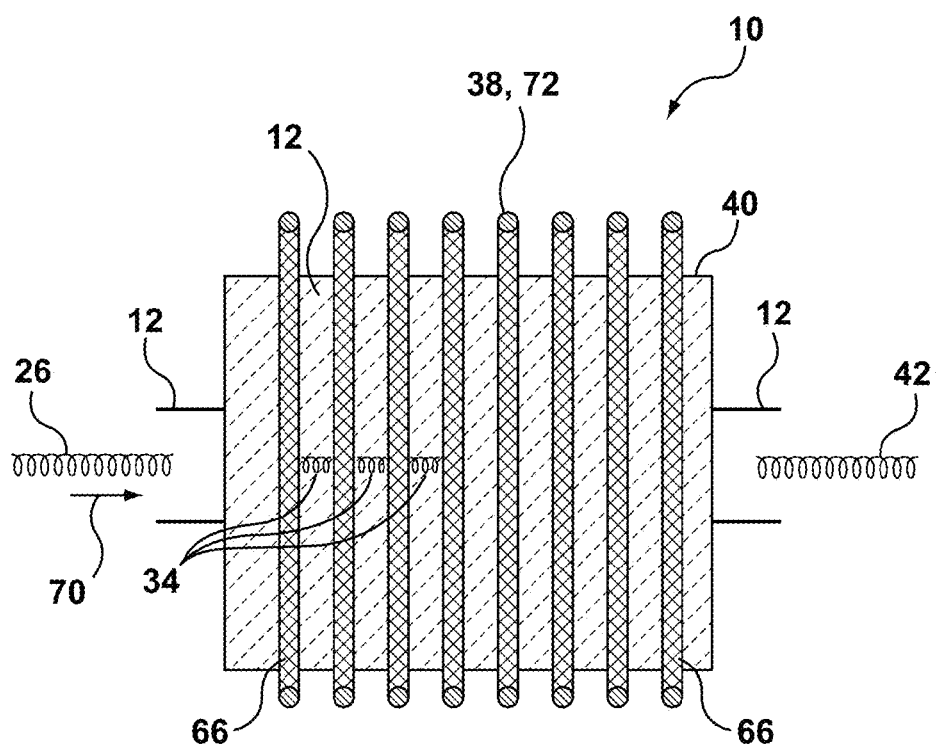
FIG. 11 is a side view of the membrane of FIG. 9 further comprising a carbon dioxide absorbing material.

In the embodiments illustrated in FIGS. 10 and 11, anesthetic circuit 10 comprises a carbon dioxide absorbing material 66. Carbon dioxide absorbing material 66 may comprise at least one of: soda lime, alkanolime, alkanolamine, amino compounds, alkali salts of amino acids, glycine, DL-alanine, beta-alanine, serine, threonine, isoleucine, DL-valine, piperazine-2-carboxilic acid, proline, arginine, gamma-aminobutyric acid, ornithine, potassium glycinate, potassium threonate, taurine, creatine and histidine. Carbon dioxide absorbing material 66 absorbs exhaled carbon dioxide 30 from flow passage 12 and decreases the amount of exhaled carbon dioxide 30 that is re-introduced to patient 20. As exemplified in FIGS. 10 and 11, carbon dioxide absorbing material 66 is located on a side of membrane 38 that is external to flow passage 12. Membrane 38 separates carbon dioxide absorbing material 66 from exhaled anesthetic agent 34 (which may be exhaled molecular anesthetic agent) retained in flow passage 12 to impede the exhaled anesthetic agent 34 from contacting the carbon dioxide absorbing material 66.

As shown in FIGS. 10 and 11, membrane 38 may separate exhaled anesthetic agent 34 in exhaled fluid mixture 26 from carbon dioxide absorbing material 66. As shown in FIG. 10, carbon dioxide absorbing material 66 may be outside of hollow fibers 72 and separated from flow passage 12 by the walls of the hollow fibers. As shown in FIG. 11, carbon dioxide absorbing material 66 may be inside the hollow fibers 72 and separated from flow passage 12 by the walls of the hollow fibers.

It is advantageous to have membrane 38 impede exhaled anesthetic agent 34 (which may be an exhaled molecular anesthetic agent) from chemically interacting with carbon dioxide absorbing material 66. When exhaled anesthetic agent 34 is sevoflurane and carbon dioxide absorbing material 66 is soda lime, for example, contact and interaction between exhaled anesthetic agent 34 and carbon dioxide absorbing material 66 can create harmful by-products, such as compound A, which may have harmful effects on patient 20, if inhaled in sufficient quantities. Since membrane 38 selectively allows more exhaled carbon dioxide 30 to pass therethrough than exhaled anesthetic agent 34 (which may be an exhaled molecular anesthetic agent), these harmful reactions are minimized, while still effectively absorbing and extracting the exhaled carbon dioxide 30 out of flow passage 12.

In some embodiments, membrane 38 comprises a dense membrane. In this case, membrane 38 is considered a dense membrane. In some cases, membrane 38 is entirely made of a dense membrane material. As will be understood by the skilled person, dense membranes comprise a solid material that is free of any pores or voids. A substance passes through a dense membrane by a process of solution and diffusion. The substance passes through membrane 38 by dissolving into membrane 38 and passing through to an opposite side thereof. In the case of a hollow fiber, the substance may pass through a wall of the hollow fiber. The dense membrane may be a dense, non-porous membrane comprising a unitary solid layer having a non-porous consistency therethrough. In some cases, membrane 38 is entirely made up of dense membrane material. In cases wherein the membrane 38 comprises a plurality of hollow fiber membranes, the wall of the membranes may be made up of a unitary solid layer.

In some embodiments, membrane 38 is a dense membrane made of polymethylpentene. More specifically, the unitary solid layer may be made of polymethylpentene. In some cases, the membrane 38 comprises a dense membrane made of polymeric silicone. More specifically, membrane 38 may comprise polydimethyl siloxane. Dense membranes rely on solution and diffusion as principles of travel through the membrane and also for selectivity. As discussed in more detail below, polymethylpentene membranes were found to have a selectivity preference to carbon dioxide and oxygen, as opposed to molecular anesthetics. Since polymeric silicone, and more specifically, polydimethyl siloxane, are dense membranes like a polymethylpentene dense membrane, a similar selectivity is predicted.

A polymethylpentene dense membrane may be used with a QUADROX-D™ oxygenator, for example. The QUADROX™ trademark is owned by MAQUET CARDIO-PULMONARY AG™. The QUADROX-D™ product is sold by MAQUET™, which is part of the GETINGE AB™ group of companies. To the best of the Applicant's knowledge, an oxygenator such as the QUADROX-D™ oxygenator has been used in on-pump cardiac surgeries. In some embodiments of the present invention, the QUADROX-D™ oxygenator is used as part of anesthetic circuit 10, as membrane housing 40 having membrane 38 therein (see FIG. 1, for example).

The QUADROX-D™ oxygenator has a membrane disposed within a membrane housing. The membrane housing for a QUADROX-D™ is made of polycarbonate. QUADROX-D™ has a blood flow rate of approximately 0.5-7 l/min. The total priming volume is 250 ml, while the effective surface area for fluid exchange is approximately 1.8 m². The effective surface area for heat exchange is approximately 0.6 m². The oxygenation fibers are made of polymethylpentene. The heat exchange fibers and potting material are made of polyurethane. The protective caps are made of polyethylene.

FIG. 12 exemplifies an oxygenator similar in its basic operation to a QUADROX-D™ oxygenator comprising a membrane housing 40 having a blood inlet 76 and a blood outlet 78. For on-pump cardiac surgeries, blood enters membrane housing 40 via blood inlet 76, passes through the membrane in the housing, and exits the membrane housing 40 via blood outlet 78 in a modified form. Typically, the modified blood exits with a higher oxygen concentration and a lower carbon dioxide concentration. In one embodiment, blood inlet 76 functions as housing inlet 44. As opposed to blood entering the housing inlet 44, exhaled fluid mixture 26 enters membrane housing 40 via housing inlet 44. In this embodiment, blood outlet 78 functions as housing outlet 46. As opposed to modified blood exiting the housing outlet 46, modified fluid mixture 42 exits the membrane housing 40 via housing outlet 46.

The oxygenator illustrated in FIG. 12 also comprises a sweep inlet 80 and a sweep outlet 82. A sweep fluid 84 enters membrane housing 40 via sweep inlet 80 and exits the membrane housing 40 via sweep outlet 82. Optionally, the sweep inlet 80, housing outlet 46, sweep outlet 82, and housing inlet 44 are staggered on four separate, orthogonal walls such that the flow of the sweep fluid 84 through membrane housing 40 is substantially orthogonal to the entry direction 70 of exhaled fluid mixture 26 into membrane housing 40. The sweep fluid 84 guides the exhaled fluid towards and into contact with the membrane within membrane housing 40. Sweep fluid 84 may be, for example, air or substantially pure oxygen.

In another embodiment, as exemplified in FIG. 13, the blood inlet 76 and the blood outlet 78 function as the inlet and outlet for the sweep fluid 84. In this embodiment, sweep inlet 80 and sweep outlet 82 function as housing inlet 44 and housing outlet 46, respectively. In the embodiment exemplified in FIG. 13, the oxygenator similar in its basic operation to QUADROX-D™ has been rotated by 90° relative to the oxygenator exemplified in FIG. 12. As exemplified in FIG. 13, sweep inlet 80 and sweep outlet 82 engage flow passage 12.

Exhaled fluid mixture 26 contacts the membrane in FIG. 13) within the membrane housing 40 such that exhaled fluid mixture 26 is converted to modified fluid mixture 42.

In some cases, the surface of membrane 38 within membrane housing 40 of an oxygenator, such as QUADROX-D™, for example, is treated with SAFELINE™ treatment. In some cases, the surface of membrane 38 may be treated with BIOLINE™ coating. In some cases, the surface of membrane 38 is not treated with the SAFELINE™ or BIOLINE™ treatment.

An example membrane 38 for use within an oxygenator, such as the QUADROX-D™ oxygenator, for example, is the OXYPLUS™ membrane. The OXYPLUS™ trademark is owned by MEMBRANA GMBH CORPORATION™. OXYPLUS™ is a polyhalocarbon membrane. OXYPLUS™ is a hydrophobic polyolefin membrane. More specifically, OXYPLUS™ is a polymethylpentene membrane. OXYPLUS™ is an asymmetric membrane having a porous support layer made of polymethylpentene and a dense layer also made of polymethylpentene. It will be appreciated that such a membrane is referred to in the art as a dense membrane, due to the presence of the dense outer layer. In turn, membrane 38 may be a membrane made up of only polymethylpentene. The dense layer may have a thickness of less than or equal to 1.5 micrometers, 1 micrometer or 0.5 micrometers. Due to the dense, non-porous nature of the dense layer, substances transfer through the dense layer by diffusion and solution, as is the conventional manner for a completely dense membrane or a dense layer.

OXYPLUS™ typically comprises hollow fibers. In this case, membrane 38 is an asymmetric membrane comprising hollow fibers 72 having at least one wall comprising a porous support layer and a dense layer. FIG. 14 shows dense layer 83 along the a portion of the outer diameter of an OXYPLUS™ hollow fiber 72, and a portion of porous support layer 85 extending inwardly from dense layer 83. Each hollow fiber 72 (a wall portion of which is shown in FIG. 14) may have an outer diameter of approximately 380 micrometers (+ or −10% or 20%) and an inner diameter of approximately 200 micrometers (+ or −10% or 20%). In some embodiments, multiple hollow fibers 72 may be cross wound with one another, to maintain a fixed position relative to one another.

Continuing to refer to FIG. 14, exhaled fluid mixture 26 may pass first through dense layer 83, then through porous support layer 85 and into the hollow fiber inner lumen 114. In this manner, the OXYPLUS™ hollow fiber membrane operates in the manner discussed with respect to FIG. 9. Alternatively, exhaled fluid mixture 26 may pass first through porous support layer 85, then though dense layer 83 and to the exterior area 116 of the hollow fiber. In this manner, the OXYPLUS™ hollow fiber membrane operates in the manner discussed with respect to FIG. 8.

FIG. 15 shows dense layer 83 and porous support layer 85, of an exemplary OXYPLUS™, magnified relative to FIG. 14.

OXYPLUS™ is produced using the ACCUREL™ process. The ACCUREL™ process is a thermally induced phase separation process, which is a Membrana GmbH™ process. Referring to FIG. 16, polymer 86 is substantially homogenously melt-mixed with solvent 88 in mixer 90 to form mix 92, while being heated by heat source 94. When producing OXYPLUS™ polymer 86 may be polymethylpentene. The solvent 88 may comprise natural seed oils, such as soy and castor, for example. The mix 92 passes through heat extruder 96. A nitrogen fluid source 98 may be used to add nitrogen to mix 92 within heat extruder 96. Mix 92 then passes through a temperature controlled air gap 100, until it reaches spinning chamber 102. In spinning chamber 102, hollow fibers 72 of the OXYPLUS™ membrane are formed by spinning and cooling hollow fibers 72. During cooling, phase separation is initiated leading to the formation of a porous skeleton structure consisting of solid polymer. In spinning chamber 102, the pores are still filled with oil. The created hollow fibers 72 are then passed to extraction chamber 106. In extraction chamber 106, the oil residues are removed from the pores using hot alcohol 108. The hollow fibers 72 are then passed to a drying stage 110 at which the hollow fibers 72 are dried to form the OXPLUS™ membrane. Spools may be used to guide the mix 92 and hollow fibers 72 through the process stages illustrated in FIG. 16. During the production process for OXYPLUS™, a dense layer 83 is created and disposed on porous support layer 85. Therefore, the OXYPLUS™ membrane comprises a porous support layer 85 surrounded by dense layer 83 (see FIGS. 14 and 15).

An alternative example membrane 38 is the ULTRAPHOBIC™ membrane produced by Membrana GmbH™. Like OXYPLUS™ ULTRAPHOBIC™ is a polyhalocarbon membrane. ULTRAPHOBIC™ is a hydrophobic polyolefin membrane. More specifically, ULTRAPHOBIC™ is a polymethylpentene membrane having a polymethylpentene porous support layer and a polymethylpentene dense layer.

FIG. 17 shows a hollow fiber 72 for the ULTRAPHOBIC™ membrane having a dense layer 83 and a porous support layer 85. FIG. 17 shows hollow fiber inner lumen 114 and hollow fiber exterior area 116. ULTRAPHOBIC™ operates in the same manner as outlined above for the OXYPLUS™ membrane (with reference to FIGS. 14-15).

The ULTRAPHOBIC™ membrane has a dense layer and a porous support layer. FIG. 18 shows dense layer 83 and porous support layer 85 for the ULTRAPHOBIC™ membrane.

Membrane 38 may comprise a glassy polymer. More specifically, membrane 38 may comprise at least one of cellulose acetate, polymide and polysulfone. Glassy polymers are diffusivity selective, meaning that they permeate polar molecules with higher solubility in the membrane material (such as carbon dioxide and oxygen gases, for example) faster than nonpolar molecules with lower solubility in the membrane material (such as sevoflurane, desflurane and isoflurane vapors, for example).

More specifically, membrane 38 may comprise a high free volume glassy polymer. More specifically, membrane 38 may comprise at least one of PTMSP [i.e. poly(1-trimethlsilyl-1-propyne) and polymethylpentene. As described in more detail below, polymethylpentene membranes were found to have a selectivity preference to carbon dioxide and oxygen, as opposed to molecular anesthetics such as sevoflurane, isoflurane and isoflurane anesthetics. PTMSP, like polymethypentene, is a high volume glassy polymer and is expected to exhibit an affinity for oxygen and carbon dioxide selectivity, as opposed to molecular anesthetic selectivity. These membranes tend to preferentially permeate materials with relatively high condensability/solubility levels (such as oxygen and carbon dioxide gas, for example). Notably, the permeation of nonpolar hydrocarbons is much lower than that of polar organic species. High free volume glassy polymers have the advantage that the permeability/flux is higher than for normal glassy polymers.

Membrane 38 may comprise a polymeric size selective membrane. These membranes function based on a molecular sieving mechanism. They allow molecules smaller than the pore sizes of the membrane (ex. oxygen and carbon dioxide gas) to pass through the membrane, while larger molecules (ex. sevoflurane, desflurane and isoflurane vapors) are substantially retained by the membrane.

Membrane 38 may comprise a polymer composite or a polymer mixed matrix membrane. Composite membranes have more than one layer of substances with different permeability/selectivity. One layer may be, for example, a high free volume layer. Mixed matrix membranes have other phases/substances immobilized in a polymer matrix. Composite membranes can be tailored to have the characteristics of normal and high free volume glassy polymers, or a size selective membrane, as discussed above, or a combination thereof. Membrane 38 may comprise a composite POLARIS™ membrane. POLARIS™ is a product offered by Membrane Technology and Research, Inc™.

Tests were conducted in which a QUADROX-D™ oxygenator was used in the set-up illustrated in FIG. 2. In this set-up, membrane 38 (within the QUADROX-D™ oxygenator) was the OXYPLUS™ membrane. Specifically, an OXYPLUS™ 90/200 membrane comprising hollow fibers 72 (see FIG. 9) having an outer diameter of 380 micrometers and a dense layer 83 having a thickness of less than 1 micrometer was used.

The results of one experiment are shown in Table 1. For this experiment, the oxygenator configuration illustrated in FIG. 13 was used. Sweep fluid 84 was oxygen. For test #1, anesthetic agent 34 was an exhaled molecular anesthetic agent and was tested separately as sevoflurane (SEVO) and isoflurane (ISO).

TABLE 1

Results of Experiment #1 (Test #1)

|  | flowrate [l/min] | $CO_2$ [%] | $O_2$ [%] | SEVO [%] | ISO [%] |
|---|---|---|---|---|---|
| Sweep Fluid 84 | 2 | 0 | 100 | 0 | 0 |
| Exhaled Fluid Mixture 26 | 6 | 4.8 | 93 | 0.92 | 0.75 |
| Modified Fluid Mixture 42 |  | 0.9 | 92 | 0.88 | 0.72 |
| Relative Change |  | −3.9 | −1 | −0.04 | −0.03 |

Experiment #2 (tests #2-4) were also conducted in which a QUADROX-D™ oxygenator was used in an anesthetic circuit 10 having one (FIG. 2), two, and three membrane(s) 38. When more than one membrane 38 is present, membranes 38 may be configured in series along flow passage 12, as shown in FIG. 5, for example. In these set-ups, membrane 38 (within the QUADROX-D™ oxygenator) was the OXYPLUS™ membrane. Specifically, an OXYPLUS™ 90/200 membrane having hollow fibers 72 with an outer diameter of 380 micrometers and a dense layer 83 having a thickness of less than 1 micrometer was used.

The results of tests #2-4 are shown in Table 2. For this group of tests, the oxygenator configuration illustrated in FIG. 12 was used. The sweep fluid 84 was air. Sweep fluid 84 had a flow rate of 30 l/min. Exhaled fluid mixture 26 had a flow rate of 7 l/min. For tests #2-4, exhaled anesthetic agent 34 was an exhaled molecular anesthetic agent, specifically, sevoflurane (SEVO).

TABLE 2

Results of Experiment #2 (Tests #2-4)

|  | Test #2 | Test #3 | Test #4 |
|---|---|---|---|
| Number of Membranes 38 | 1 | 2 | 3 |
| Exhaled Fluid Mixture 26 |  |  |  |
| $CO_2$ [%] | 4.8 | 4.8 | 4.8 |
| $O_2$ [%] | 93 | 93 | 93 |
| SEVO [%] | 1.6 | 1.6 | 1.6 |
| Modified Fluid Mixture 42 |  |  |  |
| $CO_2$ [%] | 1.2 | 0.3 | 0.1 |
| $O_2$ [%] | 86 | 63 | 48 |
| SEVO [%] | 2.1 | 2.9 | 3.4 |
| Relative Change |  |  |  |
| $CO_2$ [%] | −3.6 | −4.5 | −4.7 |
| $O_2$ [%] | −7 | −30 | −45 |
| SEVO [%] | 0.5 | 1.3 | 1.8 |

Tests #5-8 were also conducted in which a QUADROX-D™ oxygenator was used in an anesthetic circuit 10 having one (FIG. 2), two, three and four membrane(s) 38 (FIG. 5). In these set-ups, membrane 38 (within the QUADROX-D™ oxygenator) was the OXYPLUS™ membrane. Specifically, an OXYPLUS™ 90/200 membrane having hollow fibers 72 with an outer diameter of 380 micrometers and a dense layer 83 having a thickness of less than 1 micrometer was used.

The results of tests #5-8 are shown in Table 3. For this group of tests, the oxygenator configuration illustrated in FIG. 12 was used. The sweep fluid 84 was air. Sweep fluid 84 had a flow rate of 30 l/min. Exhaled fluid mixture 26 had a flow rate of 15 l/min.

TABLE 3

Results of Experiment #3 (Test #5-8)

|  | Test #5 | Test #6 | Test #7 | Test #8 |
|---|---|---|---|---|
| Number of Membranes 38 | 1 | 2 | 3 | 4 |
| Exhaled Fluid Mixture 26 $CO_2$ [%] | 4.8 | 4.8 | 4.8 | 4.8 |
| Modified Fluid Mixture 42 $CO_2$ [%] | 2.8 | 1.4 | 0.7 | 0.6 |
| Relative Change $CO_2$ [%] | −2 | −3.4 | −4.1 | −4.2 |

A fourth experiment was conducted in which an oxygenator was used in the set-up illustrated in FIG. 2. Membrane 38 was an OXYPLUS™ membrane.

For this experiment, membrane housing 40 resembled the configuration described above for FIG. 9. As the exhaled fluid mixture 26 contacted the outer surface of a hollow fiber 72, the exhaled oxygen 28 and exhaled carbon dioxide 30, selectively entered the hollow interior of at least one hollow fiber 72. The components (or portion thereof) that entered the interior of a hollow fiber 72 then passed through membrane 38 out of the flow passage 12 via at least one end of the hollow fibers 72. The portion of the exhaled fluid mixture 26 that remained exterior to the hollow fibers 72 passed around the membrane 38 as modified fluid mixture 42.

For the fourth experiment, sweep fluid 84 (see FIG. 13) passed through the interior hollow fibers 72 to measure the amount of exhaled oxygen 28, exhaled carbon dioxide 30 and exhaled molecular anesthetic agent 34 in modified fluid mixture 42 that passed into hollow fibers 72. The concentrations in the exhaled fluid mixture 26 were: 2% exhaled anesthetic agent 34 in oxygen and 4.8% exhaled carbon dioxide 30 in 94% exhaled oxygen 28. The flows were 0.8 L/min for sweep fluid 84 (see FIG. 13) and 2.0 L/min for the exhaled fluid mixture 26. The concentrations in the exiting sweep fluid stream were measured using a patient monitor and a quadruple mass spectrometer. The patient monitor measurements are reflected in volume percentages, and mass spectrometry measurements are reflected as Ion Currents in Amperes for the respective masses. By measuring the change between the original sweep fluid 84 that entered the inside of the hollow fibers from one end versus the modified sweep fluid that that exited from the other end of the hollow fibers (after the exhaled fluid passed through the membrane's hollow fiber walls and into the hollow fibers) it was possible to discern the amount of exhaled molecular anesthetic, oxygen and carbon dioxide that passed into the hollow fibers.

The results for experiment #4 are summarized in Table 4.

TABLE 4

Results of Experiment #4

|  |  | Ion Current [A] | | Percentage | |
|---|---|---|---|---|---|
| Mass |  | original | modified | original | modified |
| SEVO | Fluid Mixture |  |  |  |  |
|  | all membranes Sweep Fluid | 1.27E−09 | — | 2% | — |
|  | Ultraphobic | 6.12E−11 | 6.12E−11 | 0% | 0% |
|  | Oxyplus | 6.12E−11 | 1.09E−10 | 0% | 0.14% |
| ISO | Fluid Mixture |  |  |  |  |
|  | all membranes Sweep Fluid | 9.49E−10 | — | 2% | — |
|  | Ultraphobic | 6.72E−12 | 6.72E−12 | 0% | 0% |
|  | Oxyplus | 6.72E−12 | 7.00E−11 | 0% | 0.16% |
| DES | Fluid Mixture |  |  |  |  |
|  | all membranes Sweep Fluid | 1.06E−09 | — | 2% | — |
|  | Ultraphobic | 5.44E−12 | 5.44E−12 | 0% | 0% |
|  | Oxyplus | 5.44E−12 | 8.11E−11 | 0% | 0.15% |
| CO2 | Fluid Mixture |  |  |  |  |
|  | all membranes Sweep Fluid | 1.63E−09 | — | 4.80% | — |
|  | Ultraphobic | 4.31E−11 | 2.43E−10 | 0% | 0.70% |
|  | Oxyplus | 4.08E−11 | 7.73E−10 | 0% | 2.10% |

TABLE 4-continued

Results of Experiment #4

| | | Ion Current [A] | | Percentage | |
| --- | --- | --- | --- | --- | --- |
| | Mass | original | modified | original | modified |
| OXYGEN | Fluid Mixture | | | | |
| | all membranes Sweep Fluid | 4.00E-09 | — | 94% | — |
| | Ultraphobic | 9.36E-10 | 1.07E-09 | 21% | 23% |
| | Oxyplus | 9.45E-10 | 1.85E-09 | 21% | 41% |

FIG. 19 exemplifies a single hollow fiber 72 of the plurality of hollow fibers 72 shown in FIG. 9, for example. Exterior area 116 is separated from the inner lumen 114 of hollow fiber 72 by an outer wall 118. Outer wall 118 has a first side 120 that contacts exhaled fluid mixture 26 and permits at least a portion of exhaled carbon dioxide 30 to flow into hollow fiber 72. Exterior area 116 may be contained in membrane housing 40 (see membrane housing 40 in FIG. 1, for example). Outer wall 118 has a second side 122 that opposes first side 120. Modified fluid mixture 42 (with a reduced concentration of exhaled carbon dioxide 30) is provided after at least a portion of exhaled carbon dioxide 30 flows into hollow fiber 72. When an exhaled fluid mixture 26 arrives at the first side 120 of the hollow fiber 72, a portion of the exhaled carbon dioxide 30 travels through outer wall 118 into hollow fiber 72, and therefore the remaining fluid flows around outer wall 118 to second side 122 of hollow fiber 72 as modified fluid mixture 42, which has a lower concentration of exhaled carbon dioxide 30 than exhaled fluid mixture 26.

Hollow fiber 72 may permit a sweep fluid 84 to pass therethrough, to facilitate the transport of at least a portion of exhaled carbon dioxide 30 to travel though outer wall 118 into hollow fiber 72. Hollow fibers 72 may direct the exhaled carbon dioxide 30 out of the flow passage 12.

A sweep fluid 84 may enter the hollow fiber 72 at the sweep inlet 80 and may carry any permeates, like exhaled carbon dioxide 30, out of the hollow fiber 72 via sweep outlet 82. In some cases, membrane 38 is configured such that secondary oxygen in sweep fluid 84 passes through membrane 38 and into flow passage 12. Sweep fluid 84 may be substantially pure oxygen or air, for example.

It will be appreciated that when hollow fibers 72 are arranged substantially parallel to the entry direction 70 of exhaled fluid mixture 26 (as shown in FIG. 8), exhaled fluid mixture 26 may flow through inner lumen 114 of hollow fiber 72, sweep gas 84 flows around outer wall 118, and exhaled carbon dioxide 30 flows from inner lumen 114 to exterior area 116.

To optimize the amount of exhaled carbon dioxide transported through the membrane into (or out of) the hollow fibers, and therefore the amount of exhaled carbon dioxide removed from the exhaled fluid mixture per surface area, parameters of the membrane that may be altered include a lower thickness of the membrane, lower density of the membrane, changes in diameter of the hollow fiber, different polymerization of the membrane material resulting in less or more free volume, and/or a more rubbery or more glassy state of the membrane material. A shorter length of hollow fibers may limit the accumulation of exhaled carbon dioxide in the sweep fluid inside the hollow fiber and therefore maintain a higher partial pressure gradient for exhaled carbon dioxide and therefore better transport of exhaled carbon dioxide through the membrane.

In another embodiment of this disclosure, a membrane, as exemplified in FIG. 20, comprises a plurality of hollow fibers formed in at least one planar mat. The plurality of fibers in the first planar mat are spaced from and substantially parallel with one another.

As shown in FIG. 20, planar mat 124 comprises parallel hollow fibers 72 with a spacing 126 between each hollow fiber. In some embodiments, spacing 126 is equal throughout planar mat 124. The planar mat shown in FIG. 20 comprises warp thread 128 used to space hollow fibers 72 from each other. Warp thread 128 may be woven perpendicular to each hollow fiber 72. Warp thread 128, like hollow fibers 72, may be made of a polymeric material.

Altering the spacing of the membrane mat layers may introduce a more even flow pattern and evenly distributed carbon dioxide concentration and may, therefore, increase the average exhaled carbon dioxide transport from the exhaled fluid mixture through the membrane.

In one embodiment, membrane 38 may comprise planar mat 124, or a series of planar mats 124, stacked with each other. In some cases, the hollow fibers 72 of each stacked planar mat 124 may be aligned to provide a plurality of parallel or perpendicular hollow fibers 72, as shown in FIGS. 8 and 9, respectively. Alternatively, planar mats 124 may be stacked such that the orientations of the hollow fibers vary from one planar mat relative to another.

In an alternative embodiment, hollow fibers 72 may be formed in a planar mat 124 wherein the hollow fibers in the same planar mat 124 are arranged at different angles to one another. In some embodiments, at least some of hollow fibers 72 in a planar mat 124 are arranged so that they are not parallel or perpendicular to entry direction 70 of exhaled fluid mixture 26 (see FIGS. 8 and 9 for entry direction 70). In some embodiments, all of hollow fibers 72 are arranged at an angle other than 0° or 90° relative to entry direction 70.

In another embodiment of this disclosure, a membrane 38, as exemplified in FIG. 21a, comprises a plurality of hollow fibers 72 wound into a cylindrical roll 130 defining a hollow inner core 134 having an open end 150 to receive exhaled fluid mixture 26 therein. Cylindrical roll 130 may have a closed end 152, comprising a snap-fit cap or plug, for example. As exemplified in FIG. 21a, membrane 38 is configured to direct exhaled fluid mixture 26 radially outwardly from hollow inner core 134. As exhaled fluid mixture 26 travels radially outwardly, it contacts the plurality of hollow fibers 72 of membrane 38, to thereby convert exhaled fluid mixture 26 to modified fluid mixture 42.

FIG. 21b illustrates a cut-away view along line A-A in FIG. 21a. Although FIGS. 21a and 21b illustrate cylindrical roll 130 as a solid body for ease of illustration, it will be appreciated that the cylindrical roll 130 exemplified in FIGS. 21a and 21b is made up of a plurality of hollow fibers 72. In some embodiments, relatively long hollow fibers are wrapped or spun around a spool (in a "yarn-like" manner, for example), and cross-wound with one another. In other embodiments, a plurality of hollow fibers may be randomly arranged into a cylindrical roll 130.

In another embodiment of this disclosure, a membrane, exemplified in FIGS. 21c and 22, comprises a first planar mat rolled together in a cylindrical roll forming concentric layers of substantially parallel hollow fibers. Conversely, if the hollow fibers in the planar mat are angularly oriented to one another, the concentric layers of the hollow fibers are randomly arranged relative to one another. In a particular embodiment, rolled first planar mat defines a hollow inner core having a first open end to receive exhaled fluid and a closed second end.

Membrane 38 may comprise a rolled planar mat 124. FIGS. 21 and 22 exemplify single hollow fibers 72 or hollow fiber mats 124 (see FIG. 20) arranged as a cylindrical roll 130 with the hollow fibers 72 having a spacing between the fibers 126 and a layer spacing 132. The plurality of hollow fibers 72 in planar mat 124 may be spaced from and substantially parallel with one another. The planar mat 124 may be rolled together in a cylindrical roll 130 forming concentric layers of substantially parallel hollow fibers 72. Conversely, hollow fibers 72 may be angled relative to one another. In some embodiments, planar mat 124 defines a hollow inner core 134 along the longitudinal axis of cylindrical roll 130. As will be discussed in more detail later, in operation, exhaled fluid mixture 26 flows radially outwardly through wall thickness 136 to provide modified fluid mixture 42.

In another embodiment of this disclosure, a membrane has a portion of the plurality of hollow fibers formed in a second planar mat. In this embodiment, the plurality of hollow fibers in the second planar mat are spaced from and substantially parallel with one another. The first planar mat is overlapped with the second planar mat. The plurality of hollow fibers are formed in a first planar mat and a second planar mat. The overlapped first and second planar mats are rolled together in a cylindrical roll forming concentric layers of the hollow fibers. In a further embodiment of this disclosure, the first planar mat is overlapped with the second planar mat so that the hollow fibers of the first planar mat are oriented at an angle to the hollow fibers of the second planar mat to provide concentric layers of cross wound hollow fibers. The rolled first planar mat and second planar mat may define a hollow inner core having a first open end configured to receive the exhaled fluid mixture and a closed second end.

Membrane 38 may comprise a plurality of planar mats which overlap one another to form cross wound hollow fibers 72. The plurality of hollow fibers 72 may be formed in first planar mat 124 and second planar mat 140. To produce such a cross wound membrane, a first planar mat 124 (as shown in FIG. 19), is rolled onto temporary bobbin 138, as shown in FIG. 23. A second planar mat 140, which is similar to planar mat 124, is rolled onto temporary bobbin 142. As illustrated in FIG. 23, the plurality of hollow fibers 72 in the first planar mat 124 are spaced from and substantially parallel with each other. Similarly, the plurality of hollow fibers 72 is second planar mat 140 are spaced from and substantially parallel with each other. In some cases, the spacing 126 between all hollow fibers 72 in the same planar mat is substantially the same. Each of the first planar mat 124 and second planar mat 140 are unwound from their respective temporary bobbins 138 and 142 and each pulled into trapezoidal shapes defined between hollow fibers 72 and warp thread 128 to overlap the first planar mat 124 and the second planar mat 140 with one another as they are unwound (see FIG. 24). As shown in FIG. 24, the first planar mat 124 may be overlapped with the second planar mat 140 so that the hollow fibers 72 of first planar mat 124 are oriented at an angle 144 to hollow fibers 72 of second planar mat 140. In this manner, as shown in FIG. 25, a cross wound roll 146 is formed, and may be rolled onto temporary bobbin 148 for transport or storage. Once temporarily bobbin 148 is removed, a hollow inner core 134 (in the form of a void) is provided in cross wound roll 146. In turn, cross wound roll 146 is provided which may be used as membrane 38.

Alternatively, angle 144 in FIG. 24 may be zero, in which case all of the hollow fibers 72 of first planar mat 124 and second planar mat 140 are substantially parallel to one another. In this arrangement, membrane 38 comprises multiple rolled planar mats, but otherwise appears similar to cylindrical roll 130 shown in FIGS. 21 and 22.

FIG. 26 exemplifies flow separation apparatus 41 comprising membrane 38 in the form of cylindrical roll 130 of FIGS. 21 and 22 or cross wound roll 146 of FIG. 25 within exemplary membrane housing 40. In some embodiments, flow separation apparatus 41 is releasably connectable to an anesthetic circuit. In some cases, fluid separation apparatus 41 is in the form of a cartridge that is releasably connectable to flow path 12. As shown in FIG. 26, membrane housing 40 has housing inlet 44 and housing outlet 46 located concentrically relative to one another. The exhaled fluid mixture 26 enters housing 40 through housing inlet 44. As shown in FIG. 26, hollow inner core 134 of roll 130 or 146 has a first open end 150 configured to receive exhaled fluid mixture 26, and a closed second end 152. As exhaled fluid mixture 26 flows into hollow inner core 134, the fluid pressure in inner core 134 is increased. Closed second end 152 facilitates this increase in pressure, since exhaled fluid mixture 26 cannot escape hollow inner core 134 via closed second end 152. As pressure builds in hollow inner core 134 as exhaled fluid mixture 26 continues to flow into hollow inner core 134 (which becomes a high pressure region), exhaled fluid mixture 26 is forced radially outwardly towards a lower pressure region. This pressure differential radially between a first (inner) side of roll 130, 146 and a second (outer) side of roll 130, 146 causes outward radial fluid flow. In turn, exhaled fluid mixture 26 contacts outer wall 118 of at least some of hollow fibers 72 (see FIG. 19 for an example hollow fiber 72). As described above with reference to FIG. 19, at least a portion of exhaled carbon dioxide 30 is extracted from exhaled fluid mixture 26 into hollow fibers 72.

Sweep fluid 84 enters membrane housing 40 through sweep inlet 80. At the same time that exhaled fluid mixture 26 passes along the outer surfaces of hollow fibers 72, sweep fluid 84 passes through the inner lumen 114 (see FIG. 19) of hollow fibers 72, thereby extracting exhaled carbon dioxide 30 from exhaled fluid mixture 26. Sweep fluid 84, enriched with exhaled carbon dioxide 30, then exits membrane housing 40 via sweep outlet 82.

In some cases, exhaled fluid enters membrane housing 40 as exhaled fluid mixture 26 during patient inhalation, and exits membrane housing 40 as modified fluid mixture 42 via the same membrane housing inlet 44. In some cases, as detailed in FIG. 27, membrane housing inlet 44 and membrane housing outlet 46 are separate and concentric with one another.

Experiments were run using a cylindrical roll similar to that illustrated in FIG. 25. The cross wound roll was placed in a membrane housing (see membrane housing 40) as illustrated in FIG. 26.

Exhaled fluid mixture 26 entered the housing as a fluid comprising 93% oxygen, 4.8% carbon dioxide and 2.2% other partitions that leaked in from the air. Sweep fluid 84 entered the housing as 100% oxygen.

Exhaled fluid mixture 26 contacted hollow fibers 72 to extract exhaled carbon dioxide 30 from exhaled fluid mixture 26 to form modified fluid mixture 42. The data shows that modified fluid mixture 42 had a lower percentage of carbon dioxide than exhaled fluid mixture 26. Exhaled fluid mixture 26 passed around the exterior of the hollow fibers from hollow inner core 134 to an opposing, exterior side of hollow fibers 72 (i.e. membrane 38) to form modified fluid mixture 42. The extraction process was dependent on the flow rate (measured in liters per minute) of exhaled fluid mixture 26 when it contacted hollow fibers 72 and of sweep fluid 84 flowing though the inside of hollow fibers 72.

The relative concentration percentages (by volume) of carbon dioxide and oxygen in modified fluid mixture 42 after it was treated by membrane 38 are shown in Table 5 below. As shown in Table 5, when sweep fluid 84 flowed through hollow fibers 72, the relative amount of carbon dioxide in modified fluid mixture 42 generally decreased relative to the composition of exhaled fluid mixture 26.

Table 6 shows the relative concentration percentages (by volume) of carbon dioxide and oxygen in sweep fluid 84 after exhaled fluid mixture 26 was treated by membrane 38. As shown in Table 6, when exhaled fluid mixture 26 flowed around the exterior of hollow fibers 72, at least some of exhaled carbon dioxide 30 in exhaled fluid mixture 26 flowed into hollow fibers 72 and out of flow passage 12 (i.e. out of the modified fluid mixture 42 that flowed around hollow fibers 72).

Tables 5 and 6 show that hollow fibers 72 extracted exhaled carbon dioxide 30 from exhaled fluid mixture 26, to form modified fluid mixture 42.

TABLE 5

Modified Fluid Mixture Data for Experiment #5

| | | FLOW PER MINUTE OF EXHALED FLUID MIXTURE | | | | | | | | | | | | | | | | | | |
|---|---|---|---|---|---|---|---|---|---|---|---|---|---|---|---|---|---|---|---|---|
| | | 0 | | 0.303 | | 0.483 | | 0.742 | | 0.976 | | 2.004 | | 3.002 | | 3.966 | | 5.016 | | 5.979 | |
| | lpm | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ |
| FLOW PER | 0 | | | 92 | 4.7 | 93 | 4.7 | 93 | 4.8 | 93 | 4.8 | 93 | 4.8 | 93 | 4.8 | 93 | 4.8 | 93 | 4.8 | 93 | 4.8 |
| MINUTE | 0.303 | | | 96 | 1.2 | 98 | 3.6 | 96 | 2.9 | 94 | 3.4 | 93 | 4.2 | 93 | 4.3 | 93 | 4.5 | 93 | 4.6 | 93 | 4.6 |
| OF | 0.483 | | | 97 | 1.1 | 97 | 1.7 | 97 | 2.3 | 96 | 2.5 | 95 | 3.9 | 95 | 4.2 | 94 | 4.4 | 94 | 4.6 | 94 | 4.6 |
| OXYGEN | 0.742 | | | 98 | 0.9 | 98 | 1.3 | 97 | 1.7 | 96 | 2.2 | 95 | 3.4 | 95 | 3.9 | 94 | 4.2 | 94 | 4.3 | 94 | 4.4 |
| SWEEP | 0.976 | | | 98 | 0.5 | 98 | 1.2 | 98 | 1.4 | 97 | 2.1 | 96 | 3.1 | 95 | 3.9 | 95 | 4.1 | 94 | 4.3 | 94 | 4.3 |
| | 2.004 | | | 98 | 0.4 | 98 | 0.7 | 98 | 1 | 97 | 1.3 | 96 | 2.3 | 96 | 3 | 95 | 3.4 | 95 | 3.7 | 95 | 3.9 |
| | 3.002 | | | 98 | 0.4 | 98 | 0.6 | 98 | 0.8 | 98 | 1.1 | 97 | 1.9 | 96 | 2.6 | 96 | 3 | 95 | 3.4 | 95 | 3.7 |
| | 3.966 | | | 98 | 0.3 | 98 | 0.5 | 98 | 0.7 | 98 | 1 | 97 | 1.8 | 96 | 2.5 | 96 | 2.9 | 95 | 3.3 | 95 | 3.4 |
| | 5.016 | | | 98 | 0.3 | 98 | 0.5 | 99 | 0.6 | 98 | 0.9 | 97 | 1.6 | 96 | 2.3 | 96 | 2.7 | 96 | 3.1 | 95 | 3.3 |
| | 5.979 | | | 98 | 0.3 | 98 | 0.4 | 98 | 0.6 | 98 | 0.9 | 97 | 1.6 | 96 | 2.2 | 96 | 2.6 | 96 | 3.1 | 95 | 3.3 |
| | 6.968 | | | 98 | 0.3 | 98 | 0.4 | 98 | 0.6 | 98 | 0.8 | 97 | 1.5 | 96 | 2.1 | 96 | 2.6 | 96 | 3 | 96 | 3.2 |
| | 8.019 | | | 98 | 0.3 | 98 | 0.4 | 98 | 0.6 | 98 | 0.8 | 97 | 1.5 | 97 | 2.1 | 96 | 2.5 | 96 | 2.9 | 96 | 3.2 |
| | 9.05 | | | 98 | 0.3 | 98 | 0.3 | 98 | 0.6 | 98 | 0.8 | 97 | 1.4 | 96 | 2 | 96 | 2.4 | 96 | 2.8 | 95 | 3.1 |
| | 9.99 | | | 98 | 0.3 | 98 | 0.3 | 98 | 0.6 | 98 | 0.8 | 97 | 1.4 | 98 | 2 | 97 | 2.4 | 97 | 2.7 | 96 | 3 |
| | 11.05 | | | 96 | 0.3 | 98 | 0.3 | 98 | 0.5 | 97 | 0.8 | 97 | 1.4 | 96 | 2 | 97 | 2.4 | 95 | 2.8 | 96 | 2.9 |
| | 12.02 | | | 98 | 0.2 | 98 | 0.3 | 98 | 0.5 | 98 | 0.7 | 97 | 1.4 | 98 | 1.9 | 97 | 2.4 | 96 | 2.7 | 96 | 3 |
| | 13 | | | 97 | 0.2 | 97 | 0.3 | 98 | 0.5 | 97 | 0.7 | 97 | 1.4 | 96 | 1.9 | 97 | 2.4 | 96 | 2.8 | 96 | 2.9 |
| | 14.06 | | | 98 | 0.2 | 97 | 0.3 | 98 | 0.5 | 97 | 0.7 | 97 | 1.3 | 98 | 1.9 | 97 | 2.3 | 96 | 2.7 | 96 | 2.9 |
| | 15.04 | | | 97 | 0.2 | 98 | 0.3 | 98 | 0.5 | 97 | 0.7 | 97 | 1.3 | 96 | 1.9 | 97 | 2.3 | 95 | 2.7 | 96 | 2.9 |
| | 20 | | | 99 | 0.2 | 99 | 0.3 | 99 | 0.5 | 98 | 0.7 | 98 | 1.3 | 97 | 1.8 | 97 | 2.2 | 96 | 2.6 | 96 | 2.8 |
| | 25 | | | 99 | 0.2 | 99 | 0.3 | 99 | 0.5 | 98 | 0.7 | 98 | 1.2 | 97 | 1.8 | 97 | 2.2 | 96 | 2.5 | 96 | 2.8 |
| | 96 | | | 99 | 0.2 | 99 | 0.4 | 98 | 0.6 | 98 | 0.8 | 98 | 1.3 | 97 | 1.8 | 96 | 2.2 | 96 | 2.5 | 96 | 2.8 |

| | | FLOW PER MINUTE OF EXHALED FLUID MIXTURE | | | | | | | | | | | | | | | | |
|---|---|---|---|---|---|---|---|---|---|---|---|---|---|---|---|---|---|---|
| | | 6.968 | | 8.019 | | 9.05 | | 9.99 | | 11.05 | | 12.02 | | 13 | | 14.06 | | 15.04 | |
| | lpm | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ |
| FLOW PER | 0 | 93 | 4.8 | 93 | 4.8 | 93 | 4.8 | 93 | 4.8 | 93 | 4.8 | 93 | 4.8 | 93 | 4.8 | 93 | 4.8 | 93 | 4.8 |
| MINUTE | 0.303 | 93 | 4.7 | 93 | 4.7 | 94 | 4.7 | 94 | 4.7 | 94 | 4.7 | 94 | 4.7 | 94 | 4.7 | 94 | 4.7 | 94 | 4.7 |
| OF | 0.483 | 94 | 4.6 | 94 | 4.7 | 94 | 4.6 | 94 | 4.6 | 93 | 4.7 | 94 | 4.6 | 93 | 4.8 | 94 | 4.7 | 93 | 4.8 |
| OXYGEN | 0.742 | 94 | 4.5 | 94 | 4.5 | 94 | 4.4 | 94 | 4.5 | 94 | 4.5 | 94 | 4.5 | 94 | 4.6 | 94 | 4.4 | 94 | 4.6 |
| SWEEP | 0.976 | 94 | 4.4 | 94 | 4.5 | 94 | 4.3 | 94 | 4.4 | 93 | 4.6 | 94 | 4.4 | 93 | 4.6 | 94 | 4.5 | 94 | 4.7 |
| | 2.004 | 95 | 4 | 94 | 4.1 | 95 | 4 | 95 | 4.1 | 95 | 4.2 | 94 | 4.2 | 94 | 4.3 | 94 | 4.3 | 94 | 4.3 |
| | 3.002 | 95 | 3.8 | 95 | 3.9 | 95 | 3.8 | 95 | 3.9 | 94 | 4.1 | 95 | 4.1 | 94 | 4.2 | 94 | 4.2 | 94 | 4.4 |
| | 3.966 | 95 | 3.6 | 95 | 3.8 | 95 | 3.8 | 95 | 3.8 | 95 | 3.9 | 95 | 4 | 94 | 4 | 95 | 4.1 | 94 | 4.1 |
| | 5.016 | 95 | 3.5 | 95 | 3.7 | 95 | 3.7 | 95 | 3.8 | 94 | 4 | 95 | 3.9 | 93 | 4 | 95 | 4 | 94 | 4.2 |
| | 5.979 | 95 | 3.5 | 95 | 3.6 | 95 | 3.6 | 95 | 3.7 | 95 | 3.8 | 94 | 3.9 | 95 | 3.9 | 95 | 4 | 95 | 4 |
| | 6.968 | 95 | 3.4 | 95 | 3.6 | 95 | 3.6 | 95 | 3.7 | 95 | 3.9 | 95 | 3.9 | 95 | 4 | 95 | 4 | 94 | 4.2 |
| | 8.019 | 95 | 3.4 | 95 | 3.5 | 95 | 3.5 | 95 | 3.6 | 95 | 3.7 | 95 | 3.8 | 95 | 3.9 | 95 | 3.9 | 95 | 4 |
| | 9.05 | 95 | 3.3 | 95 | 3.5 | 95 | 3.5 | 95 | 3.6 | 95 | 3.9 | 95 | 3.8 | 95 | 4 | 95 | 3.9 | 94 | 4.1 |
| | 9.99 | 96 | 3.2 | 95 | 3.3 | 95 | 3.5 | 95 | 3.6 | 95 | 3.7 | 95 | 3.8 | 95 | 3.8 | 95 | 3.9 | 95 | 4 |
| | 11.05 | 95 | 3.2 | 96 | 3.3 | 94 | 3.6 | 95 | 3.6 | 94 | 3.8 | 95 | 3.8 | 94 | 3.9 | 95 | 3.9 | 94 | 4.1 |
| | 12.02 | 96 | 3.1 | 96 | 3.3 | 95 | 3.4 | 95 | 3.5 | 95 | 3.7 | 95 | 3.8 | 95 | 3.8 | 95 | 3.9 | 95 | 3.9 |
| | 13 | 95 | 3.2 | 95 | 3.3 | 95 | 3.6 | 95 | 3.5 | 95 | 3.8 | 95 | 3.7 | 94 | 3.9 | 95 | 3.9 | 94 | 4.1 |
| | 14.06 | 96 | 3.1 | 95 | 3.2 | 95 | 3.4 | 95 | 3.5 | 95 | 3.6 | 95 | 3.8 | 95 | 3.8 | 95 | 3.8 | 95 | 3.9 |
| | 15.04 | 95 | 3.1 | 95 | 3.2 | 95 | 3.6 | 95 | 3.5 | 94 | 3.8 | 95 | 3.7 | 94 | 3.9 | 95 | 3.8 | 94 | 4.1 |
| | 20 | 96 | 3 | 95 | 3.2 | 95 | 3.4 | 95 | 3.5 | 95 | 3.6 | 95 | 3.7 | 95 | 3.7 | 95 | 3.8 | 95 | 3.8 |
| | 25 | 96 | 3 | 96 | 3.2 | 95 | 3.4 | 95 | 3.5 | 95 | 3.6 | 95 | 3.6 | 95 | 3.7 | 95 | 3.8 | 95 | 3.8 |
| | 96 | 95 | 3 | 96 | 3.1 | 95 | 3.3 | 95 | 3.4 | 95 | 3.5 | 95 | 3.6 | 95 | 3.7 | 95 | 3.8 | 95 | 3.8 |

TABLE 6

Sweep Fluid Data for Experiment #6

| | | \multicolumn{20}{c}{FLOW PER MINUTE OF EXHALED FLUID MIXTURE} |
|---|---|---|

| | | 0 | | 0.303 | | 0.483 | | 0.742 | | 0.976 | | 2.004 | | 3.002 | | 3.966 | | 5.016 | | 5.979 | |
|---|---|---|---|---|---|---|---|---|---|---|---|---|---|---|---|---|---|---|---|---|---|
| | lpm | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ |
| FLOW PER | 0 | | | | | | | | | | | | | | | | | | | | |
| MINUTE | 0.303 | | | 93 | 2.8 | 93 | 3.6 | 92 | 4.2 | 92 | 4.5 | 92 | 4.8 | 93 | 4.3 | 90 | 4.8 | 91 | 4.8 | 91 | 4.8 |
| OF | 0.483 | | | 94 | 1.9 | 94 | 2.8 | 94 | 3.7 | 93 | 3.9 | 92 | 4.6 | 93 | 4.8 | 93 | 4.8 | 92 | 4.8 | 93 | 4.8 |
| OXYGEN | 0.742 | | | 95 | 1.9 | 95 | 2.4 | 94 | 2.8 | 94 | 3.4 | 93 | 4.2 | 93 | 4.5 | 93 | 4.5 | 93 | 4.6 | 93 | 4.6 |
| SWEEP | 0.976 | | | 95 | 1.6 | 96 | 2 | 95 | 2.3 | 94 | 2.9 | 94 | 3.6 | 93 | 4.1 | 93 | 4.2 | 93 | 4.3 | 93 | 4.4 |
| | 2.004 | | | 97 | 0.7 | 96 | 1 | 96 | 1.3 | 95 | 1.7 | 95 | 2.4 | 94 | 2.8 | 94 | 3 | 94 | 3.1 | 94 | 3.2 |
| | 3.002 | | | 96 | 0.5 | 96 | 0.7 | 96 | 0.9 | 96 | 1.2 | 95 | 1.8 | 95 | 2.1 | 95 | 2.3 | 95 | 2.4 | 95 | 2.5 |
| | 3.966 | | | 97 | 0.4 | 96 | 0.5 | 96 | 0.7 | 96 | 0.9 | 96 | 1.4 | 96 | 1.7 | 95 | 1.9 | 95 | 2 | 95 | 2 |
| | 5.016 | | | 97 | 0.3 | 97 | 0.4 | 97 | 0.6 | 96 | 0.8 | 96 | 1.2 | 96 | 1.4 | 96 | 1.5 | 95 | 1.7 | 96 | 1.7 |
| | 5.979 | | | 97 | 0.2 | 97 | 0.3 | 97 | 0.5 | 96 | 0.6 | 96 | 1 | 96 | 1.2 | 96 | 1.3 | 96 | 1.4 | 96 | 1.5 |
| | 6.968 | | | 97 | 0.2 | 97 | 0.3 | 97 | 0.4 | 96 | 0.6 | 96 | 0.9 | 96 | 1.1 | 96 | 1.2 | 96 | 1.3 | 96 | 1.3 |
| | 8.019 | | | 97 | 0.2 | 97 | 0.3 | 97 | 0.4 | 97 | 0.5 | 97 | 0.8 | 96 | 1 | 96 | 1.1 | 96 | 1.2 | 96 | 1.2 |
| | 9.05 | | | 97 | 0.2 | 96 | 0.2 | 96 | 0.3 | 96 | 0.4 | 95 | 0.7 | 95 | 0.9 | 95 | 1 | 95 | 1 | 95 | 1.1 |
| | 9.99 | | | 96 | 0.1 | 96 | 0.2 | 96 | 0.3 | 96 | 0.4 | 96 | 0.7 | 97 | 0.8 | 97 | 0.9 | 97 | 1 | 97 | 1 |
| | 11.05 | | | 97 | 0.1 | 97 | 0.2 | 97 | 0.3 | 96 | 0.4 | 96 | 0.6 | 95 | 0.8 | 97 | 0.9 | 95 | 0.9 | 97 | 1 |
| | 12.02 | | | 97 | 0 | 96 | 0.2 | 96 | 0.3 | 96 | 0.3 | 96 | 0.6 | 97 | 0.7 | 97 | 0.8 | 97 | 0.9 | 97 | 0.9 |
| | 13 | | | 97 | 0 | 97 | 0.1 | 96 | 0.2 | 96 | 0.3 | 96 | 0.6 | 96 | 0.7 | 98 | 0.8 | 96 | 0.8 | 97 | 0.9 |
| | 14.06 | | | 97 | 0 | 97 | 0.1 | 96 | 0.2 | 97 | 0.3 | 96 | 0.5 | 98 | 0.7 | 98 | 0.7 | 97 | 0.8 | 98 | 0.8 |
| | 15.04 | | | 97 | 0 | 97 | 0.1 | 97 | 0.2 | 96 | 0.3 | 96 | 0.5 | 96 | 0.6 | 98 | 0.7 | 96 | 0.7 | 98 | 0.8 |
| | 20 | | | 99 | 0 | 98 | 0.1 | 99 | 0.2 | 98 | 0.2 | 98 | 0.4 | 98 | 0.5 | 98 | 0.5 | 98 | 0.6 | 98 | 0.6 |
| | 25 | | | 99 | 0 | 99 | 0 | 98 | 0.1 | 99 | 0.2 | 98 | 0.3 | 98 | 0.4 | 98 | 0.4 | 98 | 0.5 | 98 | 0.5 |
| | 96 | | | 99 | 0 | 99 | 0 | 99 | 0.1 | 98 | 0.2 | 98 | 0.3 | 98 | 0.3 | 98 | 0.4 | 98 | 0.4 | 98 | 0.4 |

| | | \multicolumn{18}{c}{FLOW PER MINUTE OF EXHALED FLUID MIXTURE} |
|---|---|---|

| | | 6.968 | | 8.019 | | 9.05 | | 9.99 | | 11.05 | | 12.02 | | 13 | | 14.06 | | 15.04 | |
|---|---|---|---|---|---|---|---|---|---|---|---|---|---|---|---|---|---|---|---|
| | lpm | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ | $O_2$ | $CO_2$ |
| FLOW PER | 0 | | | | | | | | | | | | | | | | | | |
| MINUTE | 0.303 | 91 | 4.8 | 91 | 4.8 | 93 | 4.8 | 93 | 4.8 | 93 | 4.8 | 93 | 4.8 | 93 | 4.8 | 93 | 4.8 | 93 | 4.8 |
| OF | 0.483 | 92 | 4.8 | 93 | 4.8 | 93 | 4.8 | 93 | 4.7 | 91 | 4.8 | 93 | 4.7 | 91 | 4.9 | 94 | 4.8 | 91 | 4.8 |
| OXYGEN | 0.742 | 92 | 4.6 | 93 | 4.6 | 93 | 4.6 | 93 | 4.6 | 93 | 4.6 | 93 | 4.6 | 93 | 4.6 | 93 | 4.4 | 93 | 4.6 |
| SWEEP | 0.976 | 93 | 4.3 | 93 | 4.4 | 94 | 4.3 | 93 | 4.4 | 92 | 4.4 | 93 | 4.4 | 91 | 4.4 | 93 | 4.4 | 91 | 4.4 |
| | 2.004 | 94 | 3.2 | 94 | 3.3 | 94 | 3.4 | 94 | 3.4 | 94 | 3.4 | 94 | 3.6 | 94 | 3.5 | 94 | 3.5 | 94 | 3.5 |
| | 3.002 | 94 | 2.6 | 94 | 2.6 | 95 | 2.7 | 95 | 2.7 | 94 | 2.7 | 95 | 2.8 | 94 | 2.7 | 95 | 2.8 | 93 | 2.8 |
| | 3.966 | 95 | 2.1 | 95 | 2.1 | 95 | 2.3 | 96 | 2.3 | 95 | 2.3 | 95 | 2.8 | 95 | 2.3 | 96 | 2.4 | 95 | 2.4 |
| | 5.016 | 95 | 1.8 | 95 | 1.8 | 96 | 1.9 | 96 | 1.6 | 94 | 1.9 | 96 | 2 | 94 | 1.9 | 96 | 2 | 94 | 2 |
| | 5.979 | 95 | 1.6 | 96 | 1.6 | 96 | 1.7 | 96 | 1.7 | 96 | 1.7 | 96 | 1.9 | 96 | 1.8 | 96 | 1.8 | 96 | 1.8 |
| | 6.968 | 96 | 1.4 | 96 | 1.4 | 96 | 1.5 | 96 | 1.5 | 95 | 1.5 | 96 | 1.7 | 95 | 1.5 | 96 | 1.6 | 94 | 1.5 |
| | 8.019 | 96 | 1.2 | 96 | 1.3 | 97 | 1.3 | 97 | 1.4 | 97 | 1.4 | 97 | 1.4 | 96 | 1.4 | 96 | 1.4 | 96 | 1.4 |
| | 9.05 | 95 | 1.1 | 95 | 1.2 | 97 | 1.2 | 97 | 1.2 | 95 | 1.2 | 97 | 1.2 | 95 | 1.2 | 96 | 1.3 | 95 | 1.3 |
| | 9.99 | 97 | 1.1 | 97 | 1.1 | 97 | 1.1 | 96 | 1.2 | 97 | 1.2 | 97 | 1.2 | 97 | 1.2 | 96 | 1.2 | 96 | 1.2 |
| | 11.05 | 95 | 1 | 97 | 1 | 95 | 1 | 97 | 1.1 | 95 | 1 | 97 | 1 | 95 | 1.1 | 97 | 1.1 | 95 | 1 |
| | 12.02 | 97 | 0.9 | 97 | 0.1 | 97 | 1 | 97 | 1 | 97 | 1 | 97 | 1 | 97 | 1 | 97 | 1 | 97 | 1 |
| | 13 | 95 | 0.9 | 97 | 0.9 | 95 | 0.9 | 97 | 0.9 | 95 | 0.9 | 97 | 1 | 95 | 0.9 | 97 | 1 | 95 | 0.9 |
| | 14.06 | 97 | 0.8 | 98 | 0.9 | 97 | 0.9 | 97 | 0.9 | 97 | 0.9 | 97 | 0.9 | 97 | 0.9 | 96 | 0.9 | 96 | 0.9 |
| | 15.04 | 95 | 0.7 | 97 | 0.8 | 95 | 0.8 | 97 | 0.8 | 95 | 0.8 | 97 | 0.9 | 95 | 8 | 96 | 0.9 | 95 | 0.8 |
| | 20 | 97 | 0.6 | 97 | 0.6 | 97 | 0.7 | 97 | 0.7 | 97 | 0.7 | 97 | 0.7 | 97 | 0.7 | 96 | 0.7 | 98 | 0.7 |
| | 25 | 97 | 0.5 | 97 | 0.5 | 97 | 0.6 | 97 | 0.6 | 97 | 0.6 | 97 | 0.6 | 96 | 0.6 | 96 | 0.6 | 97 | 0.6 |
| | 96 | 98 | 0.5 | 98 | 0.5 | 98 | 0.5 | 98 | 0.5 | 98 | 0.5 | 98 | 0.5 | 98 | 0.5 | 97 | 0.5 | 97 | 0.5 |

In another embodiment of this disclosure, a membrane comprises a plurality of hollow fibers formed in planar discs vertically stacked upon one another. In some embodiments, the hollow fibers in each planar disc may be spaced from one another and oriented substantially parallel to one another in a corresponding disc direction. In some particular embodiments, the corresponding disc direction for a first disc is different than the corresponding disc direction for any other disc stacked directly adjacent to the first disc. The corresponding disc direction for all of the stacked discs may be substantially the same.

In a further embodiment shown in FIGS. 28 and 29, membrane 38 comprises a plurality of hollow fibers 72 formed in planar discs 154 stacked upon one another. The planar discs may be cut from planar mats similar to the planar mat discussed with reference to FIG. 20. As illustrated in FIGS. 28 and 29, each planar mat may be cut to define a mat having a rounded perimeter. In some embodiments, planar discs 154 have a circular shape. In other embodiments, planar discs 154 have an elliptical shape. Planar discs 154 may be stacked with a defined vertical disc spacing distance 156 between each disk. In some embodiments, vertical spacing distance 156 is zero, and the stacked planar discs 154 are in direct contact with one another. In some cases, the spacing 126 between all hollow fibers 72 in the same planar disc 154 is equal.

As exemplified in FIGS. 28 and 29, hollow fibers 72 in each planar disc are spaced from one another and oriented substantially parallel to one another in a corresponding disc direction. In some embodiments, as shown in FIG. 28, the corresponding direction of a first of planar discs 154 is different than the corresponding disc direction for any other planar disc directly adjacent to the first of planar discs 154. In other words, there may be an angle 157 between the parallel hollow fibers 72 of one planar disc 154 and the hollow fibers 72 of another planar disc 154 stacked adjacent to one another.

Alternatively, the corresponding disc directions for all of the stacked planar discs 154 may be substantially the same, in which case all of the hollow fibers 72 are substantially in parallel.

Hollow fiber discs 154 may be stacked to result in a membrane 38 in the form of stacked cylinder 158, as shown in FIG. 30. In some cases, stacked cylinder 158 contains approximately 175 to 225 planar disks 154. Each planar disk 154 may be glued to any planar disc directly above or below it. The glue may be placed on each planar disc 154 in a radial manner, so as to define a gas impermeable glue line 160 that defines a cylindrical channel 162 located radially inwardly of glue line 160. Cylindrical channel 162 may be configured to receive exhaled fluid mixture 26.

FIG. 31 illustrates an example membrane housing 40 for housing stacked cylinder 158, as discussed above with reference to FIG. 30. Stacked cylinder 158 may be glued to either end cap of the housing 40 via glue line 160 to form a fluid separation apparatus 41. As illustrated, membrane housing 40 has sweep inlet 80, sweep outlet 82, membrane housing inlet 44 and a membrane housing outlet 46. The space between the outer wall of membrane housing 40 and stacked cylinder 158 may be divided into two symmetrical compartments by two baffles 164. Sweep inlet 80 and sweep inlet 82 may be each located in a respective one of the two symmetrical volumes created by baffles 164. In the embodiment illustrated in FIG. 31, membrane outlet 46 is at the same end of membrane housing 40 as sweep inlet 80 and sweep outlet 82, between the sweep inlet and sweep outlet.

FIG. 32 shows a cut-away view through fluid separation apparatus 41 comprising a membrane housing 40. In some embodiments, fluid separation apparatus 41 is releasably connectable to an anesthetic circuit. In some cases, fluid separation apparatus 41 is in the form of a cartridge that is releasably connectable to flow path 12. Exhaled fluid mixture 26 enters membrane housing 40 via membrane housing inlet 44. As the exhaled fluid mixture 26 is forced through cylindrical channel 162 of stacked cylinder 158, at least some of exhaled carbon dioxide 30 flows into inner lumen 114 (see FIG. 19) of at least some of hollow fibers 72. The resulting modified fluid mixture 42 that flows past at least some of hollow fibers 72 has a reduced concentration of exhaled carbon dioxide 30. Unlike as shown in FIG. 31, FIG. 32 exemplifies housing outlet 46 at the same end of membrane housing 40 as membrane housing inlet 44.

Sweep fluid 84 enters membrane housing 40 through sweep inlet 80. At the same time that exhaled fluid mixture 26 passes though cylindrical channel 162 of stacked cylinder 158 and around at least some of hollow fibers 72 of stacked cylinder 158, exhaled carbon dioxide 30 is transported through outer wall 118 (see FIG. 19) of hollow fibers 72, and out of flow passage 12 via hollow fibers 72. Sweep fluid 84, enriched with exhaled carbon dioxide 30, then exits membrane housing 40 via sweep outlet 82.

In another embodiment of this disclosure, a membrane, exemplified in FIG. 33, is located in an elongate channel having a longitudinal centerline. The elongate channel is elongated about the longitudinal centerline. In some embodiments, the plurality of hollow fibers are arranged substantially perpendicular to the longitudinal centerline of the channel. In some embodiments, the elongate channel has a rounded cross-section in a plane perpendicular to the longitudinal centerline. In some embodiments, the elongate channel has a cross-section in a plane perpendicular to the longitudinal centerline and having a cross-sectional area of approximately 300 mm$^2$ to 20,000 mm$^2$. The longitudinal centerline may be curved.

FIG. 33 exemplifies a membrane that may be used as membrane 38. As exemplified, the plurality of hollow fibers 72 of membrane 38 is located in membrane housing 40 to form a fluid separation apparatus 41. Membrane housing 40 is an elongate channel 166 having a longitudinal centerline 168. Elongate channel 166 is elongated about longitudinal centerline 168.

As illustrated in FIGS. 34*a* and 34*b*, the plurality of hollow fibers 72 may be arranged substantially perpendicular to longitudinal centerline 168. Alternatively, hollow fibers 72 may be oriented at an angle other than 90° or 0° relative to longitudinal centerline 168. In these cases, exhaled fluid mixture 26 flows around hollow fibers 72, to remove exhaled carbon dioxide 30 from exhaled fluid mixture 26.

As illustrated in FIG. 35, elongate channel 166 may have a substantially rectangular cross-section in a plane perpendicular to the longitudinal centerline 168. Alternatively, elongate channel 166 may have a rounded cross-section in a plane perpendicular to longitudinal centerline 168. In some cases, elongate channel 166 may have a circular, oval, or elliptical cross-section. In other cases, elongate channel 166 may have curved edges.

Elongate channel 166 may have a cross-sectional area (in a plane perpendicular to longitudinal centerline 168) of approximately 300 mm$^2$ to 20,000 mm$^2$.

FIGS. 33, 34 and 35 show housing inlet 44 and housing outlet 46 at opposite ends of elongate channel 166. In these embodiments, exhaled fluid mixture 26/modified fluid mixture 42 flow once past membrane 38. In an alternative embodiment, housing inlet 44 and housing outlet 46 are located at the same end of elongated channel 166, to facilitate bi-directional (double) fluid flow across hollow fibers 72 of membrane 38.

In some cases, elongate channel 166 has a curved longitudinal centerline 168. FIG. 36 exemplifies a fluid separation apparatus 41 comprising a continuous elongate channel 166 disposed in membrane housing 40 and arranged in a spiral pattern. As exemplified in FIG. 36, membrane housing 40 has a membrane housing inlet 44. In operation, exhaled fluid mixture 26 enters housing 40 at membrane housing inlet 44 and travels in a direction parallel to longitudinal centerline 168 of channel 166. As exhaled fluid mixture 26 passes over hollow fibers 72 (shown in FIGS. 34 and 35), exhaled carbon dioxide 30 is extracted to provide modified fluid mixture 42. During this flow, valve 170 is in an open position. Once exhalation is finished, valve 170 closes and external fluid enters elongate channel 166 via injection port 172 (which may be near valve 170) to force the modified fluid mixture 42 to change direction and flow back towards membrane housing inlet 44 (which now functions to allow modified fluid mixture 42 to exit membrane housing 40). When modified fluid mixture 42 moves towards membrane housing inlet 44 after it passes by hollow fibers 72 for a second time, it further reduces the exhaled carbon dioxide concentration in modified fluid mixture 42. The forward and reverse fluid flow increases the contact time between the fluid mixture and the hollow fiber membranes, thereby increasing the efficiency of the exhaled carbon dioxide extraction (per inhalation/exhalation cycle). In this case, the elongate channel 116, in conjunction with injection port 172, may act as the flow generator to promote fluid movement through elongate channel 116 and, in some cases through other portions of flow passage 12 (see flow passage 12 in FIG. 1, for example).

In another embodiment of this disclosure, a membrane, exemplified in FIG. 37, is located in a housing and at least one hollow fiber of the membrane has a corresponding shape and orientation that is different than the corresponding shape and orientation of another hollow fiber. In a more specific embodiment, each hollow fiber has a corresponding shape and orientation that is different than a corresponding shape and orientation of all other hollow fibers in the housing.

FIG. 37 illustrates a further embodiment for fluid separation apparatus 41 comprising membrane 38 and membrane housing 40, wherein membrane 38 comprises a plurality of hollow fibers 72 in membrane housing 40. In this embodiment, at least one hollow fiber 72 has a corresponding shape and orientation that is different than a corresponding shape and orientation of another hollow fiber. As illustrated, each hollow fiber has a corresponding shape and orientation that is different than a corresponding shape and orientation of all other hollow fibers in membrane housing 40. Each hollow fiber 72 may have a curved shape and angular orientation relative to membrane housing 40 that is different than the curved shape and angular orientation of all other hollow fibers 72 in the membrane housing 40. In other words, hollow membranes 72 may be randomly packed (randomly oriented) into membrane housing 40 in a "spaghetti noodle-like" manner. The amount of hollow fibers 72 used per volume of space within membrane housing 40 defines the resistance for the exhaled fluid mixture 26 passing through from membrane housing inlet 44 to membrane housing outlet 46. As illustrated, a sweep fluid 84 travels through inner lumen 114 in hollow fibers 72 (see FIG. 19) to facilitate the removal of exhaled carbon dioxide from exhaled fluid mixture 26 introduced into membrane housing 40.

Each of the embodiments of membrane 38 described above may be located in a membrane housing 40 within an anesthetic circuit 10 having a membrane housing inlet 44 and a membrane housing outlet 46. As illustrated in FIGS. 1, 1a, 2, 3a, 4, 5, 6 and 7, for example, exhaled anesthetic fluid 26 enters membrane housing 40 via membrane housing inlet 44, flows once through membrane 38, then exits membrane housing 40 via membrane housing outlet 46 as modified fluid mixture 42. FIGS. 26 and 32, for example, show membrane housing inlet 44 and membrane housing outlet 46 located at the same end of the membrane housing 40. The embodiments shown in FIGS. 26 and 32 are applicable to anesthetic circuits 10 similar to those illustrated in FIGS. 1, 2, 3a, 4, 5, 6 and 7, for example, when slightly modified. For example, FIG. 38 illustrates the anesthetic circuit of FIG. 1, slightly modified to have housing outlet inlet 44 and housing outlet 46 on the same side of membrane housing 40.

Anesthetic circuit 10, as shown in FIG. 1, for example has exit outlet 22 and entry inlet 36. As exemplified in FIG. 1, entry inlet 36 and exit outlet 22 may be different openings in flow passage 12. Alternatively, as shown in FIG. 3b, for example, has one fluid port 24 in flow passage 12.

A further embodiment comprises a method for anesthetic treatment of a patient. With reference to FIG. 1, the method comprises introducing an external anesthetic agent 16 towards and into a patient via flow passage 12. External anesthetic agent 16 may be stored in anesthetic machine 18 or another external source. This anesthetic agent is delivered to patient 20, through flow passage 12. After the external anesthetic agent 16 is inhaled by patient 20, the external anesthetic agent 16 travels to the patient's lungs. The patient's lungs produce an exhaled fluid mixture 26, which is expelled from the airway of patient 20 as he/she exhales. Exhaled fluid mixture 26 is then directed away from and out of patient 20 into flow passage 12. Exhaled fluid mixture 26 from the patient 20 comprises exhaled oxygen 28, exhaled carbon dioxide 30 and exhaled anesthetic agent 34. Exhaled fluid mixture 26 is advanced through flow passage 12 towards and into contact with membrane 38 comprising a plurality of hollow fibers in fluid communication with the flow passage. More of exhaled carbon dioxide 30 than exhaled anesthetic agent 34 is transferred out of the flow passage after exhaled fluid mixture 26 contacts membrane 38 to leave modified fluid mixture 42 in flow passage 12. Modified fluid mixture 42 has a lower concentration of exhaled carbon dioxide 30 than exhaled fluid mixture 26. Modified fluid mixture 42 is advanced through flow passage 12 toward patient 20 to provide at least modified fluid mixture 42 to patient 20. Exhaled anesthetic agent 34 may be an exhaled molecular anesthetic agent.

In some embodiments, the method for anesthetic treatment of a patient includes transferring exhaled oxygen 28 through membrane 38 after exhaled fluid mixture 26 contacts membrane 38 to leave modified fluid mixture 42 in flow passage 12. In this particular embodiment, membrane 38 has an exhaled oxygen-to-exhaled anesthetic agent selectivity of greater than 1. External anesthetic agent 16 may comprise a molecular anesthetic agent, exhaled anesthetic agent 34 may be an exhaled molecular anesthetic agent, and the plurality of hollow fibers 72 may be made at least partially of polymeric material.

Exhaled anesthetic agent 34 is at least partially retained in flow passage 12 after exhaled fluid mixture 26 contacts the membrane 38. In some cases, substantially all (or substantial amounts) of the exhaled anesthetic agent 34 (which may be exhaled molecular anesthetic agent) is retained in the flow passage 12 after exhaled fluid mixture 26 contacts the membrane 38.

Referring to FIG. 7, a secondary oxygen 65 located external to flow passage 12 may pass through membrane 38 and into flow passage 12. Secondary oxygen 65 comprises any oxygen that is external to flow passage 12, prior to operation and use of membrane 38. The external oxygen may be located on a side of membrane 38 that is external to flow passage 12. External oxygen may include, for example, oxygen naturally found in atmospheric air, or a source of oxygen located outside of flow passage 12 that is in fluid communication with membrane 38. In this scenario, the external oxygen serves to increase the total oxygen concentration in flow passage 12.

Referring to FIG. 1, external fluid, which may be stored in external fluid source 52, is introduced into flow passage 12 through fluid inlet 50. In some cases, the external fluid that enters fluid inlet 50 may be enriched by oxygen from an external oxygen source 56 (see FIG. 2).

Optionally, membrane 38 is pervious to exhaled oxygen 28 such that membrane 38 has an exhaled oxygen-to-exhaled anesthetic agent selectivity of at least 2, 3, 4, 5, 10, 50, 100 or 250. In this case, exhaled anesthetic 34 may be an exhaled molecular anesthetic.

In some aspects of a method of the invention, membrane 38 is pervious to exhaled carbon dioxide 30 such that membrane 38 has an exhaled carbon dioxide-to-exhaled anesthetic agent selectivity of greater than 1. Optionally membrane 38 has a carbon dioxide-to-molecular anesthetic agent selectivity of at 2, 3, 4, 5, 10, 50, 100 or 250. In these cases, exhaled anesthetic 34 may be an exhaled molecular anesthetic agent.

For some implementations of the method of anesthetic treatment, membrane 38 may be inert with respect to exhaled carbon dioxide 30.

In some cases, the membrane is fully operable, as outlined herein, at all humidity values ranging from 0% to 100%, including humidity values ranging from 0% to 100% within any fluid adjacent to membrane 38 (see FIG. 1).

In another embodiment of the present disclosure, a fluid separation apparatus 41 is provided. Fluid separation apparatus 41 is fluidly connectable to an anesthetic circuit (such as anesthetic circuit 10 shown in FIG. 1, for example). As previously discussed, anesthetic circuit 10 has flow passage 12 for transporting exhaled fluid mixture 26 containing at least exhaled anesthetic agent 34 and exhaled carbon dioxide 30 through flow passage 12. In some embodiments, fluid separation apparatus 41 is releasably connectable with flow passage 12 of anesthetic circuit 10. In some embodiments, fluid separation apparatus 41 is a cartridge releasably connectable with flow passage 12 of anesthetic circuit 10.

FIG. 39 illustrates a perspective view of an exemplary fluid separation apparatus 41. As illustrated in FIG. 39, fluid separation apparatus 41 has a membrane housing 40. As exemplified, membrane housing 40 has membrane housing inlet 44 for receiving exhaled fluid mixture 26 therein and a membrane housing outlet 46 for expelling modified fluid mixture 42 from the interior of membrane housing 40. As shown in FIG. 39, housing inlet 44 and housing outlet 46 may be concentric with one another. Housing outlet 46 may radially surround housing inlet 44.

FIG. 40 shows a side view of the fluid separation apparatus of FIG. 39. As shown in FIG. 40, membrane housing 40 may have a sweep inlet 80 and a sweep outlet 82. Sweep inlet 80 and sweep outlet 82 may be located at opposing ends of membrane housing 40, as illustrated in FIG. 40.

FIG. 41 shows a bottom plan view of the fluid separation apparatus of FIGS. 39 and 40.

FIG. 42 shows a top plan view of the fluid separation apparatus of FIGS. 39 to 41.

FIG. 43 shows a cut-away view along line A-A in FIG. 42. As shown in FIG. 43, fluid separation apparatus 41 comprises membrane housing 40 and membrane 38 disposed therein. As exemplified in FIG. 43, membrane 38 is in the form of cylindrical roll 130, as shown in FIGS. 21a, 21b, 21c and FIG. 22, or cross wound roll 146, shown in FIG. 25, for example. In one embodiment, as exemplified in FIG. 21a, membrane 38 comprises a plurality of hollow fibers 72 wound into a cylindrical roll 130 defining a hollow inner core 134 having an open end 150 to receive exhaled fluid mixture 26 therein. It will be appreciated that although membrane 38 is shown as a solid body, for ease of illustration, membrane 38 comprises a plurality of hollow fibers 72.

Continuing to refer to FIG. 43, membrane housing 40 may comprise an inner shaft 174 inserted into hollow inner core 134. Inner shaft 174 may have apertures 175 therein to direct exhaled fluid mixture 26 through apertures 175 and into membrane 38.

Referring now to FIG. 44, fluid separation apparatus 41 is configured to receive exhaled fluid mixture 26 via housing inlet 44. As shown in FIG. 44, exhaled fluid mixture 26 may flow into hollow inner core 134. The fluid pressure in inner core 134 is increased as flow continues. Closed second end 152 facilitates this increase in pressure, since exhaled fluid mixture 26 cannot escape hollow inner core 134 via closed second end 152. Closed second end 152 may be a plug or snug-fit cap, for example. Alternatively, closed second end 152 may be integrally formed in membrane housing 40. As pressure builds in hollow inner core 134 as exhaled fluid mixture 26 continues to flow into hollow inner core 134, exhaled fluid mixture 26 is forced radially outwardly towards a lower pressure region. This pressure differential radially between a first (inner) side of membrane 38 and a second (outer) side of membrane 38 causes outward radial fluid flow. As will be described below, exhaled fluid mixture 26 is modified as it flows radially from a first side of membrane 38 to a second side of membrane 38, resulting in modified fluid mixture 42 at the second side of membrane 38. Modified fluid mixture 42 may exit fluid separation apparatus 41 via housing outlet 46. FIG. 44 shows an exemplary exhaled fluid mixture 26 and modified fluid mixture 42 flow direction through fluid separation apparatus 41. In this and other embodiments, it will be appreciated that the fluid may alternatively flow in an opposite direction, whereby exhaled fluid mixture 26 enters membrane housing 40 via membrane housing outlet 46 and modified fluid mixture 42 exits membrane housing 40 via membrane housing inlet 44.

The fluid separation apparatus of FIGS. 43 and 44 may be configured to receive sweep fluid 84 therein, as shown in FIG. 45.

FIG. 46 provides a detailed view from Detail A of FIG. 45, specifically, of an exemplary group of hollow fibers 72 within membrane 38. As shown, at the same time that exhaled fluid mixture 26 (comprising exhaled carbon dioxide 30 and exhaled anesthetic gas 34) passes along the outer surfaces of hollow fibers 72, sweep fluid 84 passes through the inner lumen 114 of hollow fibers 72, thereby extracting exhaled carbon dioxide 30 from exhaled fluid mixture 26. Sweep fluid 84, enriched with exhaled carbon dioxide 30, then exits membrane housing 40 via sweep outlet 82. As illustrated in FIG. 46, exhaled anesthetic gas 34 may pass around hollow fibers 72 such that more exhaled carbon dioxide 30 enters hollow fibers 72 than exhaled anesthetic gas 34. Exhaled fluid mixture 26 is modified as it flows radially from a first side 120 of the outer wall of each hollow fiber 72 to a second side 122 of the outer wall of each hollow fiber 72, resulting in modified fluid mixture 42 at the second side 122 of the outer wall of each hollow fiber 72.

Returning to FIG. 45, sweep fluid 84 flows from sweep inlet 80 to sweep outlet 82. In this embodiment, sweep fluid 84 travels once through membrane 38, in a substantially linear manner. In this and in all other embodiments of the present disclosure, it will be appreciated that sweep fluid 84 may alternatively travel in the opposite direction, flowing from sweep outlet 82 to sweep inlet 80.

FIGS. 47 and 48 show detailed views from FIG. 45 near sweep outlet 82 and sweep inlet 80, respectively. FIGS. 47 and 48 show the simultaneous flow of exhaled fluid mixture 26, modified fluid mixture 42 and sweep fluid 84.

An alternative embodiment of a fluid separation apparatus 41 is shown in FIG. 49. Unlike the fluid separation apparatus 41 illustrated in FIGS. 39 to 48, sweep inlet 80 and sweep outlet 82 are located at the same end of membrane housing 40. Sweep inlet 80 and sweep outlet 82 are located at the opposite end of membrane housing from membrane housing inlet 44 and membrane housing outlet 46. As shown, sweep inlet 80 and sweep outlet 82 may be adjacent to one another.

FIGS. 50 and 51 show plan side views of fluid separation apparatus 41 of FIG. 49.

FIG. 52 shows a top view of fluid separation apparatus 41 of FIGS. 49 to 51.

FIG. 53 shows a cut-away side view along line A-A in FIG. 52. FIG. 53 shows the flow of exhaled fluid mixture 26 from membrane housing inlet 44, through membrane 38; and modified fluid mixture 42 out of membrane housing outlet 46 in a similar manner to that illustrated for the fluid separation apparatus of FIG. 44. In alternative embodiments, exhaled fluid mixture 26/modified fluid mixture 42 may flow in the opposite direction to that shown in FIG. 53.

FIG. 54 exemplifies a flow path of sweep fluid 84 through the fluid separation apparatus of FIGS. 49 to 53. Membrane housing 40 is configured to direct sweep gas 84 received from sweep inlet 80 through a first portion 176 of the plurality of hollow fibers 72 in a first sweep direction and subsequently through a second portion 178 of the plurality of hollow fibers 72 in a second sweep direction substantially opposite to the first sweep direction before sweep gas 84 exits membrane housing 40 via sweep outlet 82. In some cases, first portion 176 of the plurality of hollow fibers 72 is radially outward of second portion 178 of the plurality of hollow fibers 72. In operation, sweep fluid 84 may enter membrane housing 40 via sweep inlet 80. Dividing wall 180 may be configured to direct sweep fluid 84 through membrane 38. Once sweep fluid 84 emerges from membrane 38, it enters headspace 182. Headspace wall 184 directs sweep fluid 84 back into membrane 38, passing through the membrane for a second time. In some cases, headspace wall 184 causes sweep fluid 84 to turn approximately 180 degrees and emerge from membrane 38 in a direction substantially opposite to the direction at which sweep fluid 84 reenters membrane 38. In this manner, sweep fluid 84 passes through membrane 38 at least twice.

By recirculating sweep fluid 84 through membrane 38, less sweep fluid is required to run the system. This can result in cost and energy savings. The recirculation also makes the extraction of exhaled carbon dioxide from exhaled fluid mixture more efficient. For exhaled carbon dioxide 30 to travel through membrane 38 into sweep fluid 84, the partial pressure and concentration of carbon dioxide in sweep fluid 84 has to be lower than in exhaled fluid mixture 26. In an embodiment such as that shown in FIG. 54, sweep flow 84 flows through a smaller number of hollow fibers 72 in a first portion 176 of the plurality of hollow fibers 72 than it does as it flows in a subsequent direction through the second portion 178 of hollow fibers 72. Meanwhile, the smallest amount of exhaled carbon dioxide 30 remains to be removed from exhaled fluid mixture 26 in the area of the first portion 176 of hollow fibers 72. This area has a high flow of pure sweep fluid 84 and therefore a partial pressure difference. Sweep fluid 84 containing a relatively small amount of exhaled carbon dioxide 30 as it exits the first portion 176 of hollow fibers 72 can then flow through the rest of the fibers to remove additional carbon dioxide from exhaled fluid mixture 26 with higher exhaled carbon dioxide 30 levels. In this way, a concentration difference is maintained.

Although FIG. 54 illustrates a double-flow of sweep fluid through membrane 38, it will be appreciated that in some embodiments, sweep fluid 84 may flow through membrane 38 more than twice. In these embodiments, a concentration difference of carbon dioxide is also maintained, in the manner described above, such that sweep fluid 84 has the lowest concentration of carbon dioxide as it flows through a first portion 176 of hollow fibers 72 and then has a higher concentration of carbon dioxide as it flows through subsequent portions of hollows fibers 72.

FIG. 55 shows a detailed view of FIG. 54 in the vicinity of headspace 182. FIG. 56 shows a detailed view of FIG. 54 in the vicinity of sweep inlet 80 and sweep outlet 82. Both FIGS. 55 and 56 show the simultaneous flow of exhaled fluid mixture 26, modified fluid mixture 42 and sweep fluid 84.

Another alternative embodiment of fluid separation apparatus 41 is shown in FIG. 57. As shown, sweep inlet 80 and sweep outlet 82 are located at the same end of membrane housing 40 as each other, and at the same end of membrane housing 40 as membrane housing inlet 44 and membrane housing outlet 46. Fluid separation apparatus 41 of FIG. 57 operates in a similar manner to the fluid separation apparatus shown in FIGS. 49 to 56; however, the sweep fluid 84 follows a different path.

FIG. 58 shows a front view of fluid separation apparatus 41 of FIG. 57. FIG. 59 shows a top view of fluid separation apparatus 41 of FIGS. 57 and 58.

FIG. 60 shows a cut-away side view along line A-A in FIG. 59, showing the flow of exhaled fluid mixture 26 and modified fluid mixture 42 through fluid separation apparatus 41.

FIG. 61 shows a top view of fluid separation apparatus 41 of FIGS. 57 to 59, showing the flow of sweep fluid 84 through fluid separation apparatus 41. The flow path of sweep fluid 84 is also illustrated in FIG. 62, which shows a cut-away side view along line B-B in FIG. 59. The flow path is substantially the same as that shown in FIG. 54 except that sweep gas 84 is received from sweep inlet 80 at an opposing end of membrane housing 40 (as compared to FIG. 54). In other words, sweep gas 84 flows through a first portion 176 of the plurality of hollow fibers 72 and subsequently through a second portion 178 of the plurality of hollow fibers 72 in substantially opposite directions to those shown in FIG. 54.

FIG. 63 shows a detailed view of FIG. 60 near the end of membrane housing 40 proximate membrane housing inlet 44 and membrane housing outlet 46. FIG. 64 shows a detailed view of FIG. 60 near the end of membrane housing 40 opposite membrane housing inlet 44 and membrane housing outlet 46. Both figures show the simultaneous flow of exhaled fluid mixture 26, modified fluid mixture 42 and sweep fluid 84.

In some embodiments, sweep fluid 84 comprises at least nitrogen gas, and membrane 38 is at least partially impervious to the nitrogen gas and pervious to the exhaled carbon dioxide fluid such that the membrane has a carbon dioxide-to-nitrogen gas selectivity of greater than 1. In some embodiments, a nitrogen selective polymer membrane may allow sweep fluid 84 to be air, which is less expensive than pure oxygen. Such membranes are known in the art. Examples of nitrogen selective polymer membranes include those from PARKER HANNIFIN CORPORATION™. When air is used in sweep gas 84, a nitrogen selective membrane may substantially prevent the nitrogen abundant in air to be retained by the membrane so as to not flood the flow path with nitrogen, which could be harmful to the patient.

FIGS. 65 and 66 show exemplary inner shafts 174 for membrane housing 40. Inner shaft 174 may be inserted into hollow inner core 134 (see FIG. 43, for example) of membrane 38. Inner shaft 174 may have a plurality of apertures 175 therein to direct exhaled fluid mixture 26 through apertures 175 and into membrane 38. In some cases, apertures 175 located further away from membrane housing inlet 44—and closer to the closed end 152 of membrane housing 40—are generally smaller than apertures 175 located closer to membrane housing inlet 44. Smaller apertures 175 in the area of closed end 152 act to minimize the impact of the high pressure area therein, thereby resulting in more evenly distributed pressure and flow along inner core 134.

As illustrated in FIGS. 65 and 66, inner shaft 174 has a first end 186 and a second end 187. In some embodiments, first end 186 may be located in membrane housing 40 with first end 186 closer to membrane housing inlet 44 than second end 187. Studies showed that this arrangement facilitated more even flow distribution of exhaled fluid mixture 26 into membrane 38 than an arrangement wherein inner shaft 174 has apertures 175 of equal size.

The following data, presented herein as Experiment #7, were collected in a ~35 kg pig (landrace, male).

The anaesthetic circuit used in Experiment #7 was set to deliver 12×0.55 L of gas per minute resulting in 6.6 Lpm total volume delivered to the pig.

The first data set was recorded with a fresh gas flow of 2 Lpm (50% oxygen in air) and the fluid separation apparatus was supplied with pure oxygen as sweep gas (Table 7). For corresponding measurements taken from the vicinity of the sweep inlet and sweep outlet of the fluid separation apparatus, see Table 8.

The second data set was recorded with a fresh gas flow of 4 Lpm (50% oxygen in air) and the fluid separation apparatus was supplied with pure oxygen as sweep gas (Table 9). For corresponding measurements taken from the vicinity of the sweep inlet and sweep outlet, see Table 10.

Tables 7 and 9 show the inspired fraction (Fi [Vol %]) of oxygen, $CO_2$, sevoflurane ($FiO_2$, $FiCO_2$, FiSevo) at the absorber outlet, and the end tidal fraction (et [Vol %]) of oxygen, $CO_2$, sevoflurane ($etO_2$, $etCO_2$, etSevo) in the exhaled fluid mixture.

Tables 8 and 10 show the sweep flow V [Lpm] in and out of the fluid separation apparatus ($V_{IN}$, $V_{out}$), the concentration c [Vol %] of oxygen, $CO_2$ and sevoflurane going in ($c_{IN}(O_2)$, $c_{IN}(CO_2)$, $c_{IN}(Sevo)$) and the concentration of oxygen, $CO_2$ and sevoflurane going out ($c_{OUT}(O_2)$, $c_{OUT}(CO_2)$, $c_{OUT}(Sevo)$).

The pure oxygen entering the sweep inlet had a higher concentration of oxygen than the fluid mixture entering the fluid separation apparatus, therefore some oxygen travels from the sweep gas into the exhaled fluid mixture causing a higher concentration of oxygen in the modified fluid mixture than in the exhaled fluid mixture entering the fluid separation apparatus. This is reflected in the reduced oxygen concentration in the sweep fluid leaving the fluid separation apparatus as compared to the pure oxygen entering it.

The pure oxygen entering the sweep inlet contains a lower concentration of carbon dioxide than the exhaled fluid mixture entering the fluid separation apparatus, therefore some carbon dioxide travels from the exhaled fluid mixture into the sweep fluid leaving a lower concentration of carbon dioxide in the modified fluid mixture than in the exhaled fluid mixture entering the fluid separation apparatus. This is reflected in the increased carbon dioxide concentration in the sweep fluid leaving the fluid separation apparatus as compared to the pure oxygen (containing no carbon dioxide) entering it.

Although the sevoflurane concentration inside the anesthesia loop was higher than the concentration of sevoflurane in the sweep fluid entering the fluid separation apparatus, the sweep fluid mixture did not contain detectable levels of sevoflurane after passing through the fluid separation apparatus.

While the present invention as herein shown and described in detail is fully capable of attaining the above-described objects of the invention, it is to be understood that it is the presently preferred embodiments of the present invention and thus, is representative of the subject matter which is broadly contemplated by the present invention, that the scope of the present invention fully encompasses other embodiments which may become obvious to those skilled in the art, and that the scope of the claims should not be limited by the preferred embodiments set forth in the examples, but should be given the broadest interpretation consistent with the description as a whole. Moreover, it is not necessary for a device or method to address each and every problem sought to be solved by the present invention, for it is to be encompassed by the present claims.

The invention claimed is:

1. An anesthetic circuit for treating a patient, comprising:
a flow passage;
an anesthetic agent inlet in fluid communication with the flow passage for introducing an external anesthetic agent into the flow passage;

TABLE 7

Concentrations Fi/et [Vol %] inside the anaesthesia loop
(Calibrated Datex Ohmeda patient monitor)

| $FiO_2$ | $etO_2$ | $FiCO_2$ | $etCO_2$ | FiSevo | etSevo |
|---|---|---|---|---|---|
| 83% | 77% | 0.4% | 5.1% | 2.3% | 2.3% |

TABLE 8

Flow V [Lpm] and concentrations c [Vol %] of the sweep gas flow
in and out of the absorber

| $V_{IN}$ | $V_{out}$ | $c_{IN}(O_2)$ | $c_{OUT}(O_2)$ | $c_{IN}(CO_2)$ | $c_{OUT}(CO_2)$ | $c_{IN}(Sevo)$ | $c_{OUT}(Sevo)$ |
|---|---|---|---|---|---|---|---|
| 20.1 Lpm | 18.9 Lpm | 100% | 63% | 0% | 0.3% | 0% | 0% |

TABLE 9

Concentrations Fi/et [Vol %] inside the anaesthesia loop
(Calibrated Datex Ohmeda patient monitor)

| $FiO_2$ | $etO_2$ | $FiCO_2$ | $etCO_2$ | FiSevo | etSevo |
|---|---|---|---|---|---|
| 76% | 71% | 0.3% | 5.3% | 2.6% | 2.6% |

TABLE 10

Flow V [Lpm] and concentrations c [Vol %] of the sweep gas flow
in and out of the absorber

| $V_{IN}$ | $V_{out}$ | $c_{IN}(O_2)$ | $c_{OUT}(O_2)$ | $c_{IN}(CO_2)$ | $c_{OUT}(CO_2)$ | $c_{IN}(Sevo)$ | $c_{OUT}(Sevo)$ |
|---|---|---|---|---|---|---|---|
| 20.11 Lpm | 18.7 Lpm | 100% | 90% | 0% | 0.3% | 0% | 0% | at least one fluid port in fluid communication with the flow passage for providing at least the external anesthetic agent to the patient, wherein the at least one fluid port is configured to receive an exhaled fluid mixture from the patient, the exhaled fluid mixture comprising an exhaled oxygen, an exhaled carbon dioxide and an exhaled anesthetic agent, the flow passage being in fluid communication with the at least one fluid port for receiving the exhaled fluid mixture from the at least one fluid port;

a membrane comprising a plurality of hollow fibers, the membrane being in fluid communication with the flow passage, configured to receive the exhaled fluid mixture from the at least one fluid port, and at least partially impervious to the exhaled anesthetic agent to at least partially retain the exhaled anesthetic agent in the flow passage after the exhaled fluid mixture contacts the membrane, wherein the membrane is pervious to the exhaled carbon dioxide such that the membrane has an exhaled carbon dioxide-to-exhaled anesthetic agent selectivity of greater than 1, the membrane comprises the plurality of hollow fibers wound into a roll defining a hollow inner core having an open end to receive the exhaled fluid mixture therein, the exhaled fluid mixture contacts the membrane wherein the membrane separates a portion of the exhaled carbon dioxide from the exhaled fluid mixture to leave a modified fluid mixture in the flow passage having a lower amount of the exhaled carbon dioxide than the exhaled fluid mixture, and the at least one fluid port is configured to receive the modified fluid mixture from the membrane and provide at least the modified fluid mixture to the patient; and a fluid inlet for introducing an external fluid into the flow passage to be added to the modified fluid mixture provided to the patient.

2. The anesthetic circuit of claim 1 wherein the exhaled anesthetic agent is an exhaled molecular anesthetic agent;

the membrane comprises at least one polymeric material;

the membrane is pervious to the exhaled oxygen such that the membrane has an exhaled oxygen-to-exhaled molecular anesthetic agent selectivity of greater than 1.

3. The anesthetic circuit of claim 1 wherein a carbon dioxide absorbing material is located on a side of the membrane that is external to the flow passage, wherein the membrane separates the carbon dioxide absorbing material from the exhaled anesthetic agent retained in the flow passage to impede the exhaled anesthetic agent from contacting the carbon dioxide absorbing material.

4. The anesthetic circuit of claim 1 wherein the membrane is pervious to a metabolic product including acetaldehyde, acetone, ethane, ethylene, hydrogen, isoprene, methane, methylamine or pentane; and the membrane is configured to, upon contact with the exhaled fluid mixture, leave the modified fluid mixture in the flow passage with a lower amount of the metabolic product than the exhaled fluid mixture.

5. The anesthetic circuit of claim 1 wherein the at least one fluid port comprises:

an exit outlet in fluid communication with the flow passage for providing at least the external anesthetic agent to the patient; and an entry inlet separate from the exit outlet for receiving the exhaled fluid mixture from the patient, the flow passage being in fluid communication with the entry inlet for receiving the exhaled fluid mixture from the entry inlet, and wherein the exit outlet is configured to receive the modified fluid mixture from the membrane and provide the modified fluid mixture to the patient.

6. The anesthetic circuit of claim 1 wherein the at least one fluid port includes only one fluid port, and wherein the one fluid port is in fluid communication with the flow passage for providing at least the external anesthetic agent to the patient, the one fluid port is configured to receive the exhaled fluid mixture from the patient, the flow passage being in fluid communication with the one fluid port for receiving the exhaled fluid mixture from the one fluid port, and the one fluid port is configured to receive the modified fluid mixture from the membrane and provide the modified fluid mixture to the patient.

7. The anesthetic circuit of claim 1 wherein each hollow fiber has an outer wall having a first side that contacts the exhaled fluid mixture and permits at least a portion of the exhaled carbon dioxide to flow into the hollow fiber, and an opposing second side at which the modified fluid mixture is provided after at least a portion of the exhaled carbon dioxide flows into the hollow fiber, the hollow fibers permit a sweep fluid to pass therethrough to facilitate the transport of at least a portion of the exhaled carbon dioxide into the hollow fibers, and the hollow fibers direct the exhaled carbon dioxide out of the flow passage.

8. The anesthetic circuit of claim 1 wherein the plurality of hollow fibers are spaced from one another and are arranged substantially perpendicular to a flow direction of the exhaled fluid mixture when the exhaled fluid mixture initially contacts the plurality of hollow fibers.

9. The anesthetic circuit of claim 1 wherein the plurality of hollow fibers are formed in at least a first planar mat, the plurality of hollow fibers in the first planar mat are spaced from and substantially parallel with one another, the first planar mat is rolled together into the roll forming concentric layers of substantially parallel hollow fibers, and the first planar mat defines the hollow inner core having the open end to receive the exhaled fluid mixture and a closed end.

10. The anesthetic circuit of claim 9 wherein the plurality of hollow fibers are formed in the first planar mat and a second planar mat, the plurality of hollow fibers in the second planar mat are spaced from and substantially parallel with one another, the first planar mat is overlapped with the second planar mat, the overlapped first and second planar mats are rolled together in a cylindrical roll forming concentric layers of the hollow fibers, the first planar mat is overlapped with the second planar mat so that the hollow fibers of the first planar mat are oriented at an angle to the hollow fibers of the second planar mat to provide concentric layers of cross wound hollow fibers, and the rolled first planar mat and second planar mat define the hollow inner core having the open end to receive the exhaled fluid mixture therein.

11. A fluid separation apparatus fluidly connectable to an anesthetic circuit, the anesthetic circuit having a flow passage for transporting an exhaled fluid mixture containing at least exhaled anesthetic agent and exhaled carbon dioxide through the flow passage, the fluid separation apparatus comprises:
a membrane having a plurality of hollow fibers, wherein
the membrane is at least partially impervious to the exhaled anesthetic agent to at least partially retain the exhaled anesthetic agent in the flow passage after the exhaled fluid mixture contacts the membrane,
the membrane is more pervious to the exhaled carbon dioxide than the exhaled anesthetic agent such that the membrane has an exhaled carbon dioxide-to-exhaled anesthetic agent selectivity of greater than 1, and
the membrane comprises the plurality of hollow fibers wound into a roll defining a hollow inner core having an open end to receive the exhaled fluid mixture; and
a membrane housing containing the membrane therein, wherein
the housing is configured to receive the exhaled fluid mixture via a housing inlet,
the membrane housing directs the exhaled fluid mixture into contact with the membrane, to provide a modified fluid mixture having a lower amount of the exhaled carbon dioxide than the exhaled fluid mixture,
the membrane housing directs the modified fluid mixture out of the membrane housing via a housing outlet,
at least one of the plurality of hollow fibers permits a sweep fluid to pass therethrough to facilitate the transport of at least a portion of the exhaled carbon dioxide into the at least one hollow fiber, and
the membrane housing has at least one sweep inlet to receive the sweep fluid therethrough and at least one sweep outlet to expel the sweep fluid from the membrane housing.

12. The fluid separation apparatus of claim 11 wherein
the membrane housing is configured to direct the sweep fluid received from the sweep inlet through a first portion of the plurality of hollow fibers in a first sweep direction and subsequently through a second portion of the plurality of hollow fibers in a second sweep direction substantially opposite to the first sweep direction before the sweep fluid exists the housing via the sweep outlet, and
the first portion of the plurality of hollow fibers is radially outward of the second portion of the plurality of hollow fibers.

13. The fluid separation apparatus of claim 11 wherein
the sweep fluid comprises at least nitrogen gas, the membrane is at least partially impervious to the nitrogen gas and pervious to the exhaled carbon dioxide fluid such that the membrane has an exhaled carbon dioxide-to-nitrogen gas selectivity of greater than 1.

14. The fluid separation apparatus of claim 11 wherein
the membrane housing comprises an inner shaft inserted into the hollow inner core of the membrane,
the inner shaft has a plurality of apertures therein to direct the exhaled fluid mixture through the apertures and into the membrane, and
the apertures located further away from the membrane housing inlet are smaller than the apertures located closer to the membrane housing inlet.

15. A method for anesthetic treatment of a patient, comprising:
introducing an external anesthetic agent towards and into the patient via a flow passage;
directing an exhaled fluid mixture comprising an exhaled oxygen, an exhaled carbon dioxide and an exhaled anesthetic agent away from and out of the patient into the flow passage;
advancing the exhaled fluid mixture through the flow passage towards and into contact with a membrane comprising a plurality of hollow fibers in fluid communication with the flow passage, wherein
the membrane comprises the plurality of hollow fibers wound into a roll defining a hollow inner core having an open end to receive the exhaled fluid mixture therein;
transferring more of the exhaled carbon dioxide than the exhaled anesthetic agent from the exhaled fluid mixture through the membrane and out of the flow passage after the exhaled fluid mixture contacts the membrane to leave a modified fluid mixture in the flow passage, wherein the modified fluid mixture has a lower concentration of the exhaled carbon dioxide than the exhaled fluid mixture; and
advancing the modified fluid mixture through the flow passage toward the patient to provide at least the modified fluid mixture to the patient.

16. An anesthetic circuit for treating a patient, comprising:
a flow passage;
an anesthetic agent inlet in fluid communication with the flow passage for introducing an external anesthetic agent into the flow passage;
at least one fluid port in fluid communication with the flow passage for providing at least the external anesthetic agent to the patient, wherein
the at least one fluid port is configured to receive an exhaled fluid mixture from the patient, the exhaled fluid mixture comprising an exhaled oxygen, an exhaled carbon dioxide and an exhaled anesthetic agent, the flow passage being in fluid communication with the at least one fluid port for receiving the exhaled fluid mixture from the at least one fluid port;
a membrane comprising a plurality of hollow fibers, the membrane being in fluid communication with the flow passage, configured to receive the exhaled fluid mixture from the at least one fluid port, and at least partially impervious to the exhaled anesthetic agent to at least partially retain the exhaled anesthetic agent in the flow passage after the exhaled fluid mixture contacts the membrane, wherein
the membrane is pervious to the exhaled carbon dioxide such that the membrane has an exhaled carbon dioxide-to-exhaled anesthetic agent selectivity of greater than 1,
the membrane is pervious to the exhaled oxygen such that the membrane has an exhaled oxygen-to-exhaled volatile molecular anesthetic agent selectivity of greater than 1,
the exhaled fluid mixture contacts the membrane wherein the membrane separates a portion of the exhaled carbon dioxide from the exhaled fluid mixture to leave a modified fluid mixture in the flow passage having a lower amount of the exhaled carbon dioxide than the exhaled fluid mixture, and
the at least one fluid port is configured to receive the modified fluid mixture from the membrane and provide at least the modified fluid mixture to the patient; and a fluid inlet for introducing an external fluid into the flow passage to be added to the modified fluid mixture provided to the patient.

17. The anesthetic circuit of claim 16 wherein the plurality of hollow fibers are formed in planar discs stacked upon one another, and the hollow fibers in each planar disc are spaced from one another and oriented substantially parallel to one another in a corresponding disc direction.

18. The anesthetic circuit of claim 16 wherein the plurality of hollow fibers of the membrane are located in an elongate channel having a longitudinal centerline.

19. The anesthetic circuit of claim 18 wherein the plurality of hollow fibers are arranged substantially perpendicular to the longitudinal centerline of the elongate channel.

20. The anesthetic circuit of claim 18 wherein the longitudinal centerline is curved.

21. The anesthetic circuit of claim 16 wherein the plurality of hollow fibers of the membrane are located in a membrane housing, the hollow fibers are randomly packed into the membrane housing, the exhaled fluid mixture enters the housing via a housing inlet, the membrane housing directs the exhaled fluid mixture into contact with the membrane to provide the modified fluid mixture, and the membrane directs the modified fluid mixture out of the membrane housing via a housing outlet.

* * * * *